US010071945B2

(12) United States Patent
Neckers et al.

(10) Patent No.: US 10,071,945 B2
(45) Date of Patent: Sep. 11, 2018

(54) NUCLEAR RECEPTOR MODULATORS AND THEIR USE FOR THE TREATMENT AND PREVENTION OF CANCER

(75) Inventors: Jane B. Neckers, Bethesda, MD (US); Yeong Sang Kim, Gaithersburg, MD (US); Sunmin Lee, Boyds, MD (US); Vineet Kumar, Rockville, MD (US); Sanjay V. Malhotra, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 612 days.

(21) Appl. No.: 14/126,178

(22) PCT Filed: Jun. 15, 2012

(86) PCT No.: PCT/US2012/042753
§ 371 (c)(1),
(2), (4) Date: Feb. 7, 2014

(87) PCT Pub. No.: WO2012/174436
PCT Pub. Date: Dec. 20, 2012

(65) Prior Publication Data
US 2014/0171503 A1    Jun. 19, 2014

Related U.S. Application Data

(60) Provisional application No. 61/497,129, filed on Jun. 15, 2011.

(51) Int. Cl.
*A61K 31/12* (2006.01)
*A61K 31/275* (2006.01)
(Continued)

(52) U.S. Cl.
CPC ........... *C07C 49/796* (2013.01); *A61K 31/12* (2013.01); *A61K 31/275* (2013.01); *A61K 45/06* (2013.01);
(Continued)

(58) Field of Classification Search
CPC ...... A61K 31/12; A61K 31/275; A61K 45/06; C07C 49/796; C07C 205/45; C07C 255/56
See application file for complete search history.

(56) References Cited

U.S. PATENT DOCUMENTS 6,046,212 A    4/2000  Zwaagstra et al.
6,071,957 A    6/2000  Miller et al.
(Continued)

FOREIGN PATENT DOCUMENTS

WO    WO 98/15524 A1    4/1998
WO    WO 99/00114 A2    1/1999
(Continued)

OTHER PUBLICATIONS

Prescott, B. International Journal of Clinical Pharmacology and Biopharmacy (1975), 11 (4), 332-5 (Abstract only).*
(Continued)

*Primary Examiner* — Sahar Javanmard
(74) *Attorney, Agent, or Firm* — Leydig, Voit & Mayer, Ltd.

(57) ABSTRACT

Disclosed are compounds which are nuclear receptor modulators that can act as antagonists to the androgen receptor, for example, a compound of Formula I: wherein $R_1$ to $R_5$ and $X_1$ to $X_5$ are as described herein, as well as pharmaceutically acceptable salts, solvates, and stereoisomers thereof. Pharmaceutical compositions comprising such compounds, as well as methods of use, and treatment for cancers, including
(Continued)

prostate cancers, other nuclear receptor mediated cancers, and other conditions, are also disclosed.

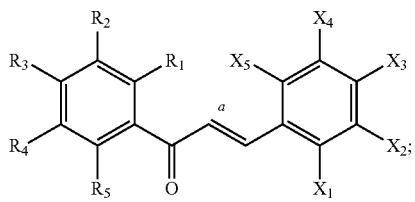

I

17 Claims, 20 Drawing Sheets

Specification includes a Sequence Listing.

(51) Int. Cl.
| | |
|---|---|
| A61K 45/06 | (2006.01) |
| C07C 49/796 | (2006.01) |
| C07C 255/56 | (2006.01) |
| C07C 205/45 | (2006.01) |
| C07C 49/80 | (2006.01) |
| C07C 49/813 | (2006.01) |
| C07C 49/84 | (2006.01) |

(52) U.S. Cl.
CPC ............ *C07C 49/80* (2013.01); *C07C 49/813* (2013.01); *C07C 49/84* (2013.01); *C07C 205/45* (2013.01); *C07C 255/56* (2013.01)

(56) References Cited

U.S. PATENT DOCUMENTS

| | | | |
|---|---|---|---|
| 6,767,916 B2 | 7/2004 | Bombardelli et al. | |
| 7,361,774 B2 | 4/2008 | Ohnogi et al. | |
| 7,498,357 B2 | 3/2009 | Ohnogi et al. | |
| 7,572,831 B2 * | 8/2009 | Kim ...................... | A61K 31/12 514/545 |
| 2004/0176471 A1 | 9/2004 | Lin et al. | |
| 2007/0149466 A1 | 6/2007 | Milburn et al. | |
| 2009/0036519 A1 | 2/2009 | Mae et al. | |

FOREIGN PATENT DOCUMENTS

| | | |
|---|---|---|
| WO | WO 00/51959 A1 | 9/2000 |
| WO | WO 01/46110 A2 | 6/2001 |
| WO | WO 03/097576 A2 | 11/2003 |
| WO | WO 2004/031165 A1 | 4/2004 |
| WO | WO 2006/112330 A1 | 10/2006 |
| WO | WO 2012/116362 A2 | 8/2012 |

OTHER PUBLICATIONS

Batts, W. Journal of Medicinal Chemistry, 1993, vol. 36, No. 10. pp. 1434-1442.*
Lokeshware et al., Annals New York Academy of Sciences, Feb. vol. 878, Issue 1, Feb. 6, 2006.*
Gerwick, W. in Food Factors for Cancer Prevention, p. 343-347.*
Tang, et al., Int. J. Cancer: 127, 1758-1768 (2010) VC 2010 UICC.*
UCLA Chem Tutorials—"Stereochemistry Tutorials: Assigning R/S and E/Z". http://www.chem.ucla.edu/harding/tutorials/steroechem/rsez.pdf. (public dated Oct. 2011 http://www.chem.ucla.edu/harding/tutorials/.*
Trakoontivakorn, G. et al., J. Agric. Food Chem. 2001, 49, 3046-3050.*
Bellmunt, J. and William, K. Oh, Ther Adv Med Oncol (2010) 2(3): 189-207.*
Bonkhoff, H. et al, Prostate, Sep. 15, 2001, 48(4): 285-91.*
European Patent Office: Supplementary European Search Report in European Patent Application No. 12800764.8 (dated Sep. 29, 2014).
Kumar et al., "Novel Chalcone Derivatives as Potent Nrf2 Activators in Mice and Human Lung Epithelial Cells," *Journal of medicinal Chemistry*, 54(12), 4147-4159 (May 3, 2011).
Liu et al., "Antiproliferative activity of chalcones with basic functionalities," *Bioorganic Y& Medicinal Chemistry*, 15(22), 7021-7034 (Sep. 26, 2007).
Parmar et al., "Anti-invasive Activity of Alkaloids and Polyphenolics in Vitro," *Bioorganic & Medicinal Chemistry*, 5(8), 1609-1619 (Jan. 1, 1997).
International Search Report in corresponding International Patent Application No. PCT/US2012/042753, dated Sep. 12, 2012.
Written Opinion in corresponding International Patent Application No. PCT/US2012/042753, dated Sep. 12, 2012.
International Preliminary Report on Patentability in corresponding International Patent Application No. PCT/US2012/042753, dated Jan. 3, 2014.
ANTO, Ruby John, et al., "Anticancer and antioxidant activity of synthetic chalcones and related compounds," *Cancer Letters*, vol. 97, No. 1, pp. 33-37 (Oct. 20, 1995).
Boumendjel, Ahcéne, et al., "Antimitotic and Antiproliferative Activities of Chalcones: Forward Structure-Activity Relationship," *Journal of Medicinal Chemistry*, vol. 51, No. 7, pp. 2307-2310 (Apr. 10, 2008).
De Leon, Johanny Tonos, et al., "Targeting the regulation of androgen receptor signaling by the heat shock protein 90 cochaperone FKBP52 in prostate cancer cells," *Proceedings of the National Ac:ademy of Sciences*, vol. 108, No. 29, pp. 11878-11883 (Jul. 19, 2011).
Doré, Jean-Christophe, et al., "Recherches en Chimiothérapie Antitumorale-IX: Activité Cytotoxique Sur Cellules Tumorales en Culture de Chalcones Substituées et de Composés Apparentés," *Journal de pharmacie de Beigique*, vol. 29, No. 4, pp. 341-351 (1974).
Henmi, Kayo, et al., "Methoxy- and Fluoro-chalcone Derivatives Arrest Cell Cycle Progression and Induce Apoptosis in Human Melanoma Cell A375," *Biological & Pharmaceutical Bulletin*, vol. 32, No. 6, pp. 1109-1113 (Jun. 2009).
Kim, Yeong Sang, et al., "Methoxychalcone Inhibitors of Androgen Receptor Translocation and Function," *Bioorganic & Medicinal Chemistry Letters*, vol. 22, No. 5, pp. 21-5-2109 (Mar. 1, 2012) (published author manuscript).
Krivtsov, Andrei V., et al., "H3K79 Methylation Profiles Define Murine and Human MLL-AF4 Leukemias," *Cancer Cell*, vol. 14, pp. 355-368 (Nov. 4, 2008) (with 9 pgs. supplemental data).
LeBlanc, Regan, et al., "Synthesis and cytotoxicity of epoxide and pyrazole analogs of the combretastatins," *Bioorganic & Medicinal Chemistry*, vol. 13, No. 21, pp. 6025-6034 (Nov. 2005).
Pati, Hari N., et al., "1,3-Diaryl-2-propenones and 2-Benzylidene-1,3-indandiones: A Quest for Compounds Displaying Greater Toxicity to Neoplasms than Normal Cells," *Archiv der Pharmazie (Weinheim)*, vol. 343, No. 9, pp. 535-541 (Sep. 2010) (published author manuscript).
Tran, Chris, et al., "Development of a Second-Generation Antiandrogen for Treatment of Advanced Prostate Cancer," *Science*, vol. 324, No. 5928, pp. 787-790 (May 8, 2009) (published author manuscript).
Ullah, Ahsan, et al., "Combinatorial Synthesis, Lead Identification, and Antitumor Study of a Chalcone-Based Positional-Scanning Library," *Chemistry & Biodiversity*, vol. 4, No. 2, pp. 203-214 (2007).
Wang, Qianberi, et al., "Androgen Receptor Regulates a Distinct Transcription Program in Androgen-independent Prostate Cancer," *Cell*, vol. 138, pp. 245-256 (Jul. 24, 2009).
Yano, Akihiro, et al., "Inhibition of Hsp90 activates osteoclast c-Src signaling and promotes growth of prostate carcinoma cells in bone," *Proceedings of the National Academy of Sciences*, vol. 105, No. 40, pp. 15541-15546 (Oct. 7, 2008).
U.S. Appl. No. 14/000,816, filed Dec. 10, 2013.

(56) References Cited

OTHER PUBLICATIONS

Alimirah et al. "DU-145 and PC-3 human prostate cancer cell lines express androgen receptor: Implications for the androgen receptor functions and regulation," *FEBS Letters*, 580: 2294-2300 (2006).
Antonarakis et al. "AR-V7 and Resistance to Enzalutamide and Abiraterone in Prostate Cancer," *New England Journal of Medicine*, 371(11) 1028-1038 (Sep. 11, 2014), published online Sep. 3, 2014.
Hoffman-Censits et al. "A Novel Antiadrogen for Patients with Castrate-Resistant Prostate Cancer," *Clin Cancer Res*, 19(6): 1335-1339 (Mar. 15, 2013), published online Jan. 8, 2013.
Liao et al. "Androgen Stimulates Matrix Metalloproteinase-2 Expression in Human Prostate Cancer," *Endocrinology*, 144(5):1656-1663 (May 2003).
Rathkopf et al. "Androgen Receptor Antagonists in Castration-Resistant Prostate Cancer," *Cancer J.—Author Manuscript*, published in final form as *Cancer J.* 19(1): 43-49 (2013).
Abdel-Aziz, M. et al., "Synthesis and screening of anti-cancer,antioxidant, and anti-inflammatory activities of novel galloyl pyrazoline derivatives" Pharmaceutical Biology 47(9): 854-863 (2009).
Batovska et al., "Examination of growth inhibitory properties of synthetic chalcones for which antibacterial activity was predicted" European Journal of Medicinal Chemistry 44: 2211-2218 (2009).
CAS Registry No. 175205-29-5, STN Entry date: Apr. 17, 1996, 1 page.
CAS Registry No. 633301-04-9, STN Entry date: Jan. 2, 2004, 1 page.
CAS Registry No. 727369-98-4, STN Entry date: Aug. 16, 2004, 1 page.
CAS Registry No. 849185-86-0, STN Entry date: Apr. 26, 2005, 1 page.
CAS Registry No. 850085-27-7, STN Entry date: May 9, 2005, 1 page.
CAS Registry No. 940741-40-2, STN Entry date: Jul. 2, 2007, 1 page.
CAS Registry No. 949257-25-4, STN Entry date: Oct. 5, 2007, 1 page.
CAS Registry No. 949689-36-5, STN Entry date: Oct. 9, 2007, 1 page.
CAS Registry No. 949752-03-8, STN Entry date: Oct. 9, 2007, 1 page.
CAS Registry No. 1003719-67-2, STN Entry date: Feb. 15, 2008, 1 page.
CAS Registry No. 1010260-51-1, STN Entry date: Mar. 26, 2008, 1 page.
CAS Registry No. 1014280-14-8, STN Entry date: Apr. 13, 2008, 1 page.
CAS Registry No. 1017098-16-6, STN Entry date: Apr. 24, 2008, 1 page.
CAS Registry No. 1030751-70-2, STN Entry date: Jun. 26, 2008, 1 page.
CAS Registry No. 1031152-45-0, STN Entry date: Jun. 27, 2008, 1 page.
CAS Registry No. 1090435-25-8, STN Entry date: Dec. 26, 2008, 1 page.
CAS Registry No. 1095826-44-0, STN Entry date: Jan. 26, 2009, 1 page.
CAS Registry No. 1223867-82-0, STN Entry date: May 16, 2010, 1 page.
CAS Registry No. 1287238-86-1, STN Entry date: Apr. 28, 2011 1 page.
CAS Registry No. 1287253-92-2, STN Entry date: Apr. 28, 2011, 1 page.
CAS Registry No. 1287265-56-8, STN Entry date: Apr. 28, 2011, 1 page.
CAS Registry No. 1287383-43-0, STN Entry date: Apr. 29, 2011, 1 page.
IP Australia: Examination Report in Australian Patent Application No. 2012271403 (dated Mar. 6, 2017) 11 pages.
Liu et al., "Antimalarial Alkoxylated and Hydroxylated Chalones: Structure-Activity Relationship Analysis" Journal of Medicinal Chemistry, 44(25): 4443-4452 (2001).
Hsu et al., "Chalcone inhibits the proliferation of human breast cancer cell by blocking cell cycle progression and inducing apoptosis" *Food and Chemical Toxicology, 44*: 704-713, 2006.
Liu et al., "Functionalized chalcones as selective inhibitors of P-glycoprotein and breast cancer resistance protein" *Bioorganic & Medicinal Chemistry, 16*: 171-180, 2008.
Szliszka et al., "Chalcones and dihydrochalcones augment TRAIL-mediated apoptosis in prostate cancer cells" *Molecules, 15*: 5336-5353, 2010.
European Patent Office, Extended European Search Report, Patent Application No. 17211083.5, dated May 4, 2018, 9 pages.

\* cited by examiner

Concentration-dependent inhibition of R1881-induced PSA and TMPRSS2 expression by hits C-11 and C-12 (LNCaP, 20 hr)

PCA Mapping (59.6%)

C86 at 5uM in LNCaP, 20h treatment

SEQUENCE LISTING

<160> NUMBER OF SEQ ID NOS: 8

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
agtccctgcc ctttgtacac a                                    21

<210> SEQ ID NO 2
<211> LENGTH: 19
<212> TYPE: DNA
<213> ORGANISM: Artificial Sequence
<220> FEATURE:
<223> OTHER INFORMATION: Synthetic

<400> SEQUENCE: 2
cgatccgagg gcctcacta                                       19

<210> SEQ ID NO 3
<211> LENGTH: 22
<212> TYPE: DNA
<213> ORGANISM: Artificial Sequence
<220> FEATURE:
<223> OTHER INFORMATION: Synthetic

<400> SEQUENCE: 3
gcagcattga accagaggag tt                                   22

<210> SEQ ID NO 4
<211> LENGTH: 23
<212> TYPE: DNA
<213> ORGANISM: Artificial Sequence
<220> FEATURE:
<223> OTHER INFORMATION: Synthetic

<400> SEQUENCE: 4
cacgtcattg gaaataacat gga                                  23

<210> SEQ ID NO 5
<211> LENGTH: 23
<212> TYPE: DNA
<213> ORGANISM: Artificial Sequence
<220> FEATURE:
<223> OTHER INFORMATION: Synthetic

<400> SEQUENCE: 5
agcctctgac tttcaacgac cta                                  23

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
tgttctggct gcagcatcat                                      20

<210> SEQ ID NO 7
<211> LENGTH: 22
<212> TYPE: DNA
<213> ORGANISM: Artificial Sequence

```
<220> FEATURE:
<223> OTHER INFORMATION: Synthetic

<400> SEQUENCE: 7
aggaaaagtg gtctgccctg ta                                      22

<210> SEQ ID NO 8
<211> LENGTH: 27
<212> TYPE: DNA
<213> ORGANISM: Artificial Sequence
<220> FEATURE:
<223> OTHER INFORMATION: Synthetic

<400> SEQUENCE: 8
actatcaatg ttgggttctc ctagaag                                 27
```

NUCLEAR RECEPTOR MODULATORS AND THEIR USE FOR THE TREATMENT AND PREVENTION OF CANCER

CROSS-REFERENCE TO A RELATED APPLICATION

This application is a U.S. National Phase of International Patent Application No. PCT/US2012/042753, filed Jun. 15, 2012, which claims the benefit of U.S. Provisional Patent Application No. 61/497,129, filed Jun. 15, 2011, the disclosure of each are incorporated by reference.

STATEMENT REGARDING FEDERALLY SPONSORED RESEARCH OR DEVELOPMENT

This invention was made with Government support under project number ZIC SC 006743 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 1,866 Byte ASCII (Text) file named "715697ST25.TXT," created on Nov. 25, 2013.

BACKGROUND OF THE INVENTION

In the United States there will be at least an estimated 217,000 new cases of prostate cancer, and over 32,000 deaths as a result of prostate cancer this year. Treatment of advanced prostate cancer is limited by the development of resistance to antiandrogen therapy. Androgen receptors (AR), as well as other sex steroid binding receptors, such as the estrogen receptor (ER) and progesterone receptor (PR) have been previously classified as type I nuclear receptors. Castrate-resistant prostate cancer (CRPC) is commonly associated with increased AR gene expression, which can occur through AR gene amplification or other mechanisms. Elevated AR expression is necessary and sufficient to confer resistance to antiandrogen therapy in mouse xenograft models. In addition, first generation AR antagonists such as bicalutamide (also called Casodex®) or flutamide demonstrate agonist properties in cells engineered to express higher AR amounts. The partial agonism of these compounds is a potential liability, best illustrated clinically by the antiandrogen withdrawal response in which serum concentrations of prostate specific antigen (PSA) decline in patients after discontinuation of either of these AR antagonists. Collectively, these findings implicate increased AR expression as a molecular cause of drug resistance and suggest that second generation antiandrogens and nuclear receptor modulators might be identified by their ability to retain antagonism in cells expressing excess AR.

In view of the foregoing, there currently exists an unmet need for therapy for cancer, particularly prostate cancer, and more particularly, advanced castrate-resistant prostate cancer.

BRIEF SUMMARY OF THE INVENTION

In an embodiment, the present invention provides a compound having the following Formula I:

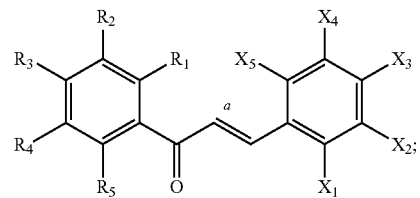

wherein $R_1$ to $R_5$ are the same or different and are each selected from the group consisting of H, $C_1$-$C_6$ alkyl, $C_2$-$C_6$ alkenyl, $C_2$-$C_6$ alkynyl, $C_1$-$C_6$ hydroxyalkyl, $C_1$-$C_6$ alkoxy, $C_1$-$C_6$ alkoxy $C_1$-$C_6$ alkyl, $C_1$-$C_6$ alkylamino, di-$C_1$-$C_6$ alkylamino, $C_1$-$C_6$ dialkylamino $C_1$-$C_6$ alkyl, $C_1$-$C_6$ thioalkyl, $C_2$-$C_6$ thioalkenyl, $C_2$-$C_6$ thioalkynyl, $C_6$-$C_{22}$ aryloxy, $C_2$-$C_6$ acyloxy, $C_2$-$C_6$ thioacyl, $C_1$-$C_6$ amido, and $C_1$-$C_6$ sulphonamido; wherein $X_1$ to $X_5$ are the same or different and are each selected from the group consisting of H and electron withdrawing groups; and wherein bond "a" can be either in the E or Z form; or a pharmaceutically acceptable salt, solvate, or stereoisomer thereof with the proviso that $R_1$ to $R_5$ and $X_1$ to $X_5$ cannot all be H simultaneously; and when only one of $R_1$ to $R_5$ is methoxy and the others of $R_1$ to $R_5$ are H, and four of $X_1$ to $X_5$ are H, then the remaining one of $X_1$ to $X_5$ cannot be an electron withdrawing group which is either $NO_2$, CN or $CF_3$.

In accordance with an embodiment, the present invention provides pharmaceutical composition comprising a compound, salt, solvate, or stereoisomer of any one of the compounds of Formula I, as set forth above, and a pharmaceutically acceptable carrier.

In accordance with another embodiment, the present invention provides pharmaceutical composition comprising a compound, salt, solvate, or stereoisomer of any one of the compounds of Formula I, as set forth above, and at least one or more other antiandrogen compounds, and a pharmaceutically acceptable carrier.

In accordance with another embodiment, the present invention provides pharmaceutical composition comprising a compound, salt, solvate, or stereoisomer of any one of the compounds of Formula I, as set forth above, and at least one or more other anticancer compounds, and a pharmaceutically acceptable carrier.

In a further embodiment, the present invention provides a method of treating or preventing cancer in a subject comprising administering to the subject an effective amount of a compound, salt, solvate, or stereoisomer of any one of the compounds of Formula I, as set forth above.

In another embodiment, the present invention provides a method of inhibiting AR activation in a subject, comprising administering to the subject an effective amount of a compound, salt, solvate, or stereoisomer of any one of the compounds of Formula I, as set forth above.

In an embodiment, the present invention also provides a method of inducing AR degradation in a prostate cancer cell of a subject, comprising administering to the subject an effective amount of a compound, salt, solvate, or stereoisomer of any one of the compounds of Formula I, as set forth above.

In accordance with an embodiment, the present invention provides a method of treatment of cancer in a subject comprising administering an effective amount of a compound of Formula I:

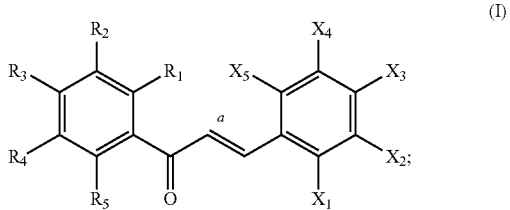

(I)

wherein $R_1$ to $R_5$ are the same or different and are each selected from the group consisting of H, $C_1$-$C_6$ alkyl, $C_2$-$C_6$ alkenyl, $C_2$-$C_6$ alkynyl, $C_1$-$C_6$ hydroxyalkyl, $C_1$-$C_6$ alkoxy, $C_1$-$C_6$ alkoxy $C_1$-$C_6$ alkyl, $C_1$-$C_6$ alkylamino, di-$C_1$-$C_6$ alkylamino, $C_1$-$C_6$ dialkylamino $C_1$-$C_6$ alkyl, $C_1$-$C_6$ thioalkyl, $C_2$-$C_6$ thioalkenyl, $C_2$-$C_6$ thioalkynyl, $C_6$-$C_{22}$ aryloxy, $C_2$-$C_6$ acyloxy, $C_2$-$C_6$ thioacyl, $C_1$-$C_6$ amido, and $C_1$-$C_6$ sulphonamido; wherein $X_1$ to $X_5$ are the same or different and are each selected from the group consisting of H and electron withdrawing groups; and wherein bond "a" can be either in the E or Z form; or a pharmaceutically acceptable salt, solvate, or stereoisomer thereof.

Compounds of the invention advantageously inhibit cancer by more than one mechanism. For example, compounds of the invention target Hsp40 and affect the regulation of the androgen receptor pathway indirectly, i.e. unlike all currently approved antiandrogens or the antiandrogen MDV3100, these compounds do not bind to the androgen receptor, and thus, when the androgen receptor is mutated, as frequently occurs in advanced prostate cancer, these compounds are still efficacious. In addition, compounds of the invention also inhibit expression of genes in the androgen-independent, androgen receptor-dependent pathway of advanced, castrate-resistant prostate cancer, as exemplified by their inhibition of UBE2C. This pathway is not inhibited by currently approved antiandrogens or MDV3100.

BRIEF DESCRIPTION OF THE SEVERAL VIEWS OF THE DRAWING(S)

FIG. 1 is a schematic illustration of the structure of the AR. The AR consists of three major domains, NTD, DBD, and LBD, which is the binding site for androgen and androgen receptor antagonists, such as bicalutamide. Three AR+ human prostate cancer cell lines, LAPC-4, LNCaP and 22Rv1 were used in this study. While LAPC-4 cells have wild-type AR, LNCaP and 22Rv1 cells have mutant AR. LNCaP cells have a point mutation in the LBD (T877A), and 22Rv1 cells also have a point mutation in the LBD (H874Y). In addition to the H874Y point mutation, 22Rv1 cells have a truncated AR allele lacking the LBD.

FIG. 2 depicts the chemical structures for flutamide, nilutamide and bicalutamide, which are FDA approved for the treatment of prostate cancer. MDV3100 is an antiandrogen compound in phase III development for castrate-resistant prostate cancer.

FIG. 3 is a graph showing the inhibition of PSA mRNA expression. Based on initial the structural analysis, 11 compounds were selected and tested in LNCaP cells to determine whether those compounds inhibited PSA mRNA expression, as assayed by real time RT-PCR. As shown in the graph, a hit was identified that inhibited over 90% PSA mRNA expression in LNCaP cells at 10 µM after 20 hours of treatment.

FIG. 4 shows a graph depicting a dose-dependent PSA mRNA inhibition study with the initial hit compound, and bicalutamide. The $IC_{50}$ of PSA mRNA inhibition of the initial hit compound and bicalutamide was 1.7 µM and 0.3 µM, respectively. Twenty six compounds were then designed and screened based on the initial hit.

FIG. 5 is PSA mRNA inhibition data on the 26 additional compounds that were tested at 2.5 µM, and 6 compounds were identified that were more potent than the original hit compound.

FIG. 6 shows the results of testing of AR target gene expression in the presence of the synthetic androgen R1881. As shown in the graph, the AR target genes PSA and TMPRSS2 were induced about 500-fold, and 30-fold, respectively, by R1881, when compared with the DMSO control. This mRNA induction was blocked by Compound 11 or Compound 12 in a dose-dependent manner. Although Compound 12 was more active at high concentrations, it showed weak agonistic effect at 1 µM, which is not desirable.

FIG. 7 is a graph showing the results of an AR translocation experiment. LNCaP cells were incubated on cover slips in phenol red free RPMI 1640 with 10% charcoal stripped FBS and 1% antimycotic-antibiotic solution for three days. Cells were treated with DMSO, bicalutamide (10 µM) or Compound 11 for three hours, followed by treatment with 1 nM R1881 for three hours. Cells were washed with PBS, fixed with 0.4% paraformaldehyde for 30 min at 37° C., washed with PBS, permeabilized with 0.4% Triton X-100 for 10 min, and then stained with anti-AR antibody (1:100 dilution, Santa Cruz Biotechnology, Santa Cruz, Calif.) for 1 hour at room temperature. After washing with PBS, cells were stained with FITC-labeled goat anti-rabbit IgG (1:200 dilution, BD Biosciences, San Jose, Calif.) for 1 hour at room temperature. After washing with PBS, cells were incubated for 10 min with Hoechst 33342 for nuclear staining, washed, and the dried cover slips were mounted on glass slides with SlowFade Gold anti-fade reagent (Invitrogen). Fluorescence images were obtained using a Leica® DM IRB fluorescence microscope, and nuclear-to-cytoplasmic AR ratios were measured using OpenLab® (Perkin Elmer, Waltham, Mass.) software. Compound 11 was markedly more active than bicalutamide in inhibiting R1881-induced AR translocation to the nucleus.

FIG. 8 is a graph depicting the PSA mRNA level of a series on compounds. The graph identifies a series of small molecules that inhibit more than 50% PSA expression at 1 µM. Among them, Compound 32, Compound 49, and Compound 103 showed the highest activity, inhibiting over 75% PSA mRNA expression at 1 µM.

FIG. 9 is a graph showing the dose dependent effects on PSA and TMPRSS2 mRNA levels in LNCaP cells treated with Compound 49 and Compound 103. Both compounds inhibited PSA mRNA expression 50% at 500 nM. This activity was very similar to that of bicalutamide, which had an $IC_{50}$ of 300 nM. No agonistic effects were observed.

FIG. 10 shows PSA and TMPRSS2 mRNA expression in the presence of R1881, a synthetic androgen. LNCaP cells were incubated for 3 days in phenol red-free RPMI 1640 supplemented with 10% charcoal-stripped FBS and 1% antimycotic-antibiotic solution, and then cells were treated for 20 hours. The concentration of R1881 was 0.5 nM, and that of the corresponding compounds was 10, 5 or 1 µM, respectively. Compound 49 inhibited PSA mRNA expression 80% in the presence of R1881 at 5 µM. This activity was similar to bicalutamide.

FIG. 11 shows the concentration-dependent inhibition of LNCaP cell growth by Compound 49. LNCaP cells were incubated with Compound 49 for 3 days. Viable cell number was determined by Trypan blue staining and counting in a hemocytometer. The IC$_{50}$ value of Compound 49 was 3 µM.

FIG. 12 is a graph showing that Compound 49 and Compound 103 inhibited PSA and TMPRSS2 mRNA, but were not effective at inhibiting UBE2C in LNCaP cells. In contrast, Compound 86 inhibited expression of all three AR target genes.

FIG. 13 is a graph showing that Compound 49 inhibited PSA mRNA expression 80% compared to control, however it completely failed to inhibit UBE2C mRNA expression in human prostate cancer cell line 22Rv1. Compound 86 inhibited expression of all three AR target genes effectively. No inhibition was observed with bicalutamide.

FIG. 14 is a graph illustrating that PSA mRNA expression in human prostate cancer cells 22Rv1 were insensitive to 20 hours of exposure to antiandrogen compound MDV3100, even at 10 but the cells were sensitive to Compound 86 at 5 µM.

FIG. 15 is a western blot showing the association of Compound 86 with Hsp40 protein in 22Rv1 cell lysates. Briefly, 22Rv1 cell lysate was incubated with biotinylated compounds (300 µM) overnight at 4° C. with gentle rotation, followed by addition of NeutrAvidin agarose beads, and incubation for 2 hours at 4° C. Beads were washed and associated proteins were recovered by boiling with SDS sample buffer, and western blot was performed with anti-Hsp40 antibody. Lane (a) is biotinylated dimethoxyphenol (negative control), lane (b) is biotinylated Compound 86, and lane (c) is 22Rv1 cell lysate (positive control).

Figure 19A:
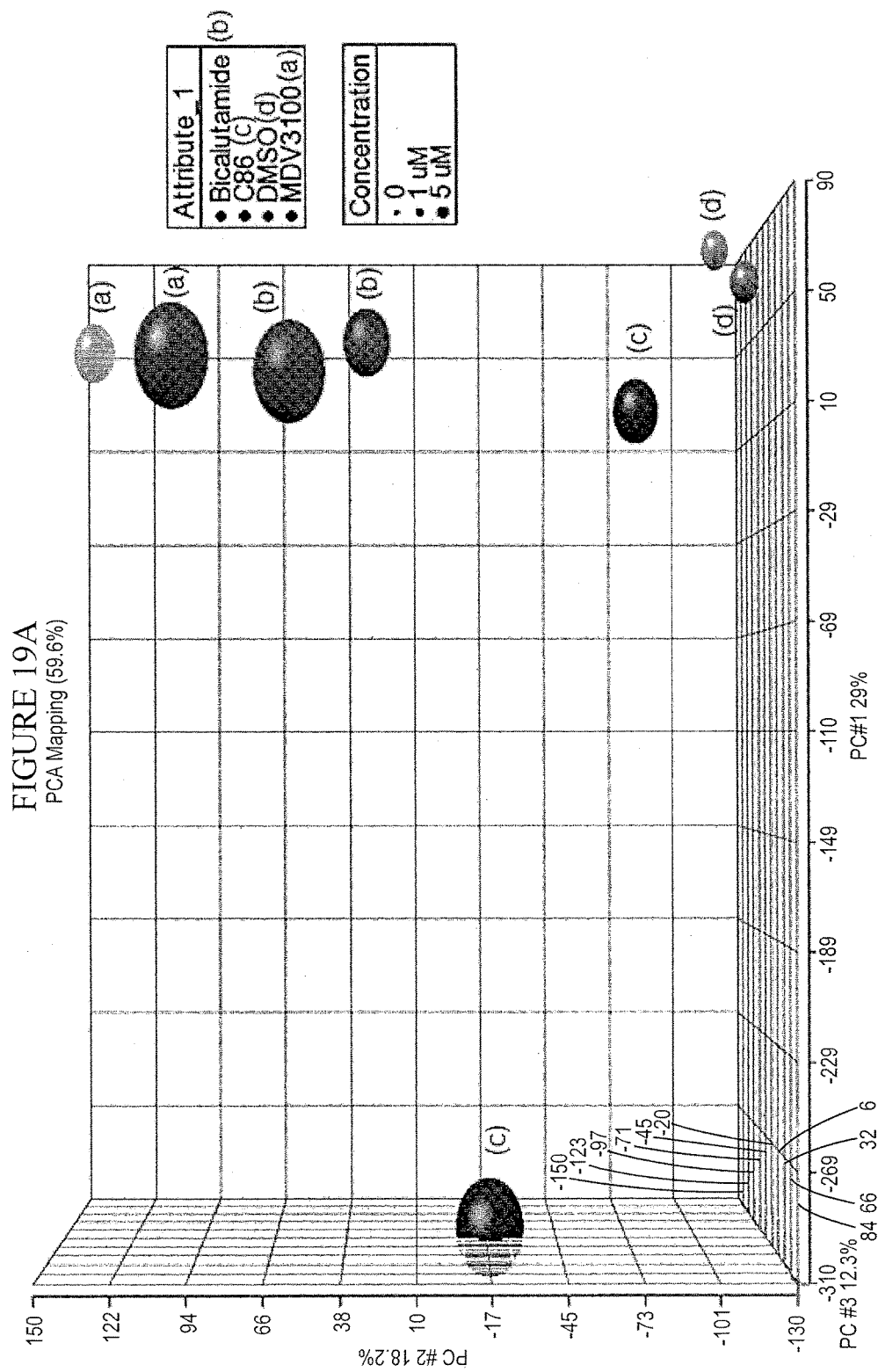
Figure 19B:
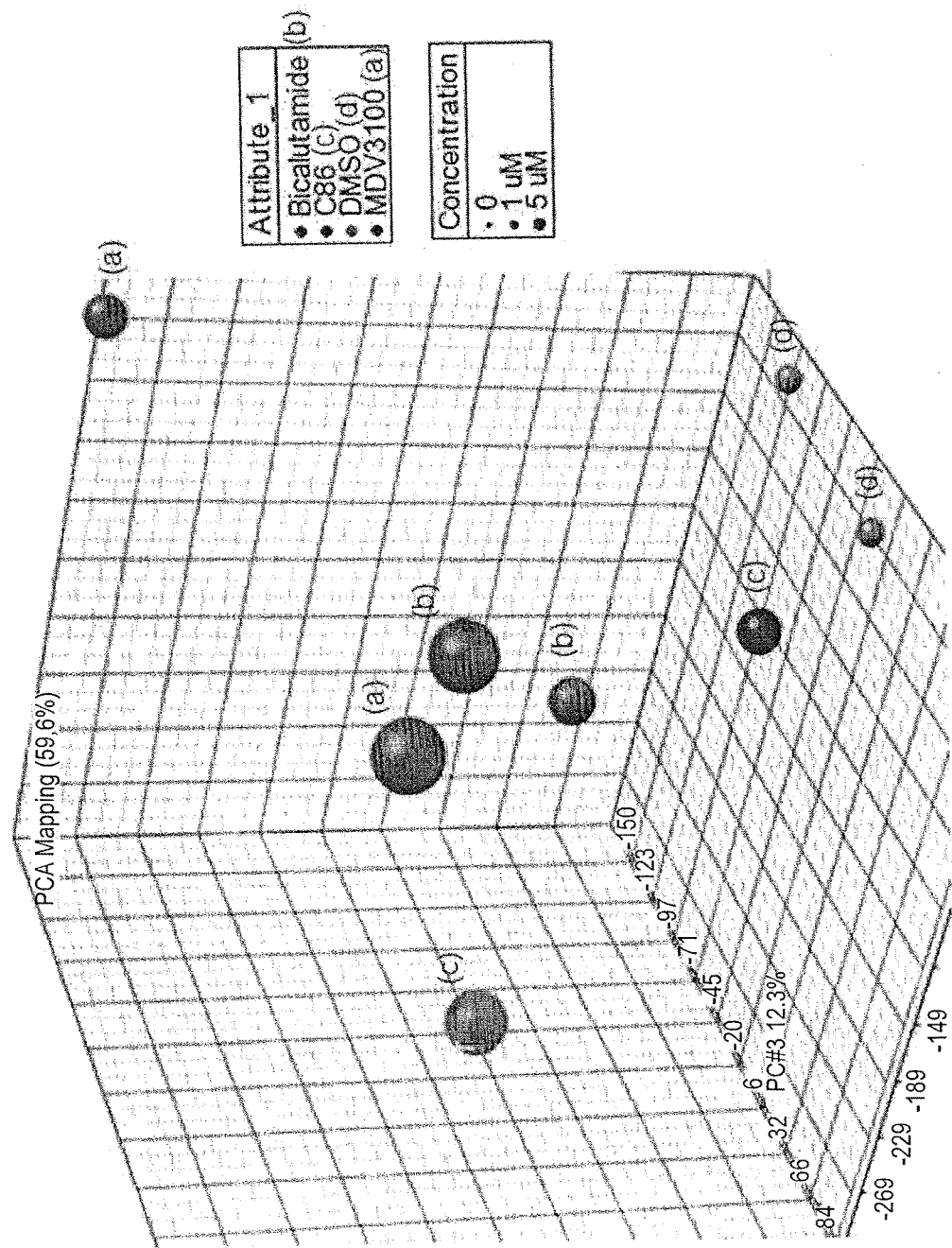

FIG. 19 depicts a principal component analysis (PCA) of the microarray results comparing the genome-wide effects on transcription of DMSO, bicalutamide, MDV3100 and Compound 86. The PCA in FIG. 19A shows that Compound 86 has a distinctive transcriptional response when compared to DMSO, bicalutamide or MDV3100. FIG. 19B depicts a different view in 3-dimensional space again reinforcing the differences between Compound 86 versus DMSO, bicalutamide and MDV3100. This visual assessment is consistent with our data showing that Compound 86 and not DMSO, bicalutamide, or MDV3100, can inhibit the androgen-independent, androgen receptor-dependent transcriptional program of castrate-resistant prostate cancer.

Figure 20:
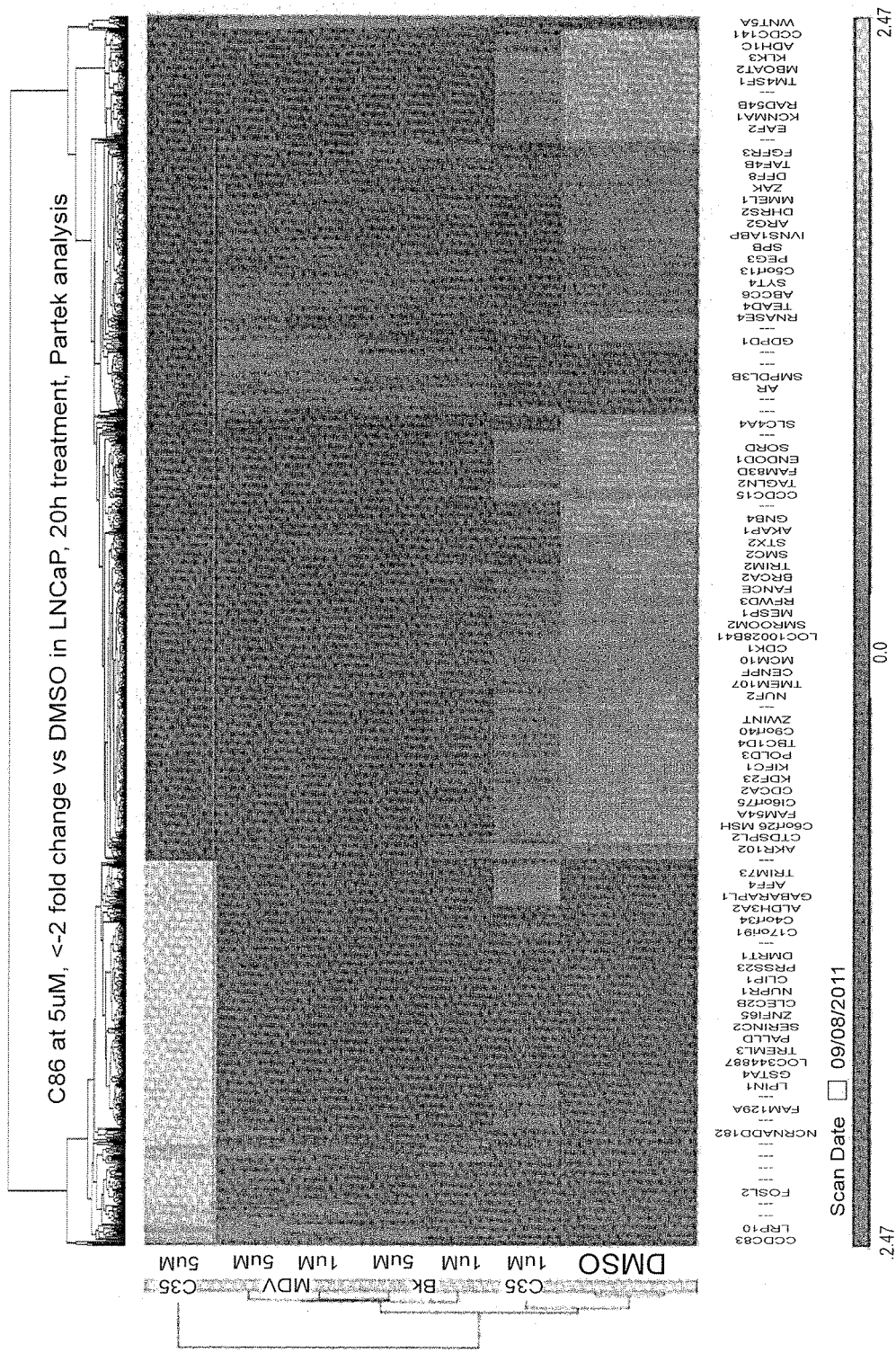

FIG. 20 depicts the hierarchical clustering of genes that showed a greater than 2-fold difference between Compound 86 and DMSO control.

Figure 21:
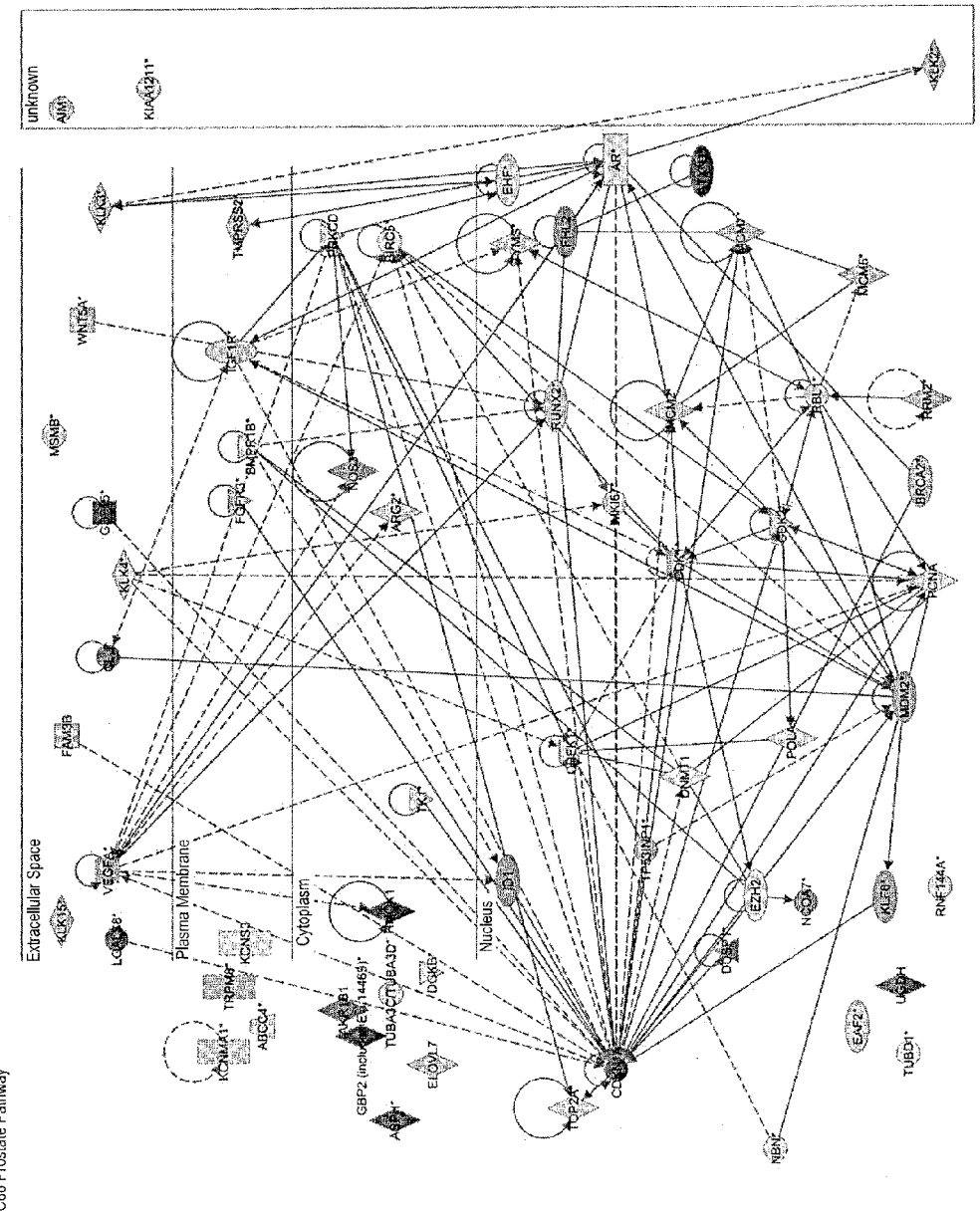

FIG. 21 depicts an Ingenuity Pathway Analysis of the prostate pathway of genes significantly regulated by Compound 86 in LNCaP human prostate carcinoma cells.

DETAILED DESCRIPTION OF THE INVENTION

In accordance with an embodiment, the present invention provides compounds of Formula I, for treating or preventing cancers, such as prostate cancer, and castrate resistant prostate cancer.

In an embodiment, the present invention provides a compound of Formula I:

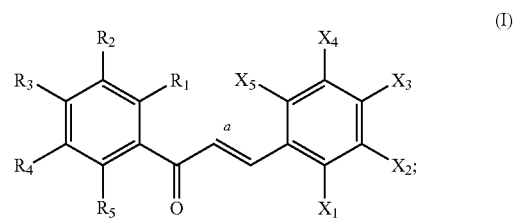

wherein $R_1$ to $R_5$ are the same or different and are each selected from the group consisting of H, $C_1$-$C_6$ alkyl, $C_2$-$C_6$ alkenyl, $C_2$-$C_6$ alkynyl, $C_1$-$C_6$ hydroxyalkyl, $C_1$-$C_6$ alkoxy, $C_1$-$C_6$ alkoxy $C_1$-$C_6$ alkyl, $C_1$-$C_6$ alkylamino, di-$C_1$-$C_6$ alkylamino, $C_1$-$C_6$ dialkylamino $C_1$-$C_6$ alkyl, $C_1$-$C_6$ thioalkyl, $C_2$-$C_6$ thioalkenyl, $C_2$-$C_6$ thioalkynyl, $C_6$-$C_{22}$ aryloxy, $C_2$-$C_6$ acyloxy, $C_2$-$C_6$ thioacyl, $C_1$-$C_6$ amido, and $C_1$-$C_6$ sulphonamido; wherein $X_1$ to $X_5$ are the same or different and are each selected from the group consisting of H and electron withdrawing groups; and wherein bond "a" can be in either the E or Z form, or a pharmaceutically acceptable salt thereof, with the proviso that $R_1$ to $R_5$ and $X_1$ to $X_5$ cannot all be H simultaneously; and when only one of $R_1$ to $R_5$ is methoxy and the others of $R_1$ to $R_5$ are H, and four of $X_1$ to $X_5$ are H, then the remaining one of $X_1$ to $X_5$ cannot be an electron withdrawing group which is either $NO_2$, CN or $CF_3$.

In accordance with an embodiment, the present invention provides a compound of formula I, as set forth above, wherein the electron withdrawing group is selected from the group consisting of $N_3$, CN, $NO_2$, CHO, NCS, SCN, F, Cl, Br, I, $OCF_3$, $SO_3H$, $B(OH)_2$, $PO(OH)_2$, $PO(OH)(OR")$, $PO(OR")_2$, $SO_2NHOH$, $SO_2NH_2$, $CONH_2$, $CONHOH$, SR", SOR", $SO_2R"$, $SO_2NHR"$, $SO_2N(R")R"$, $SO_2NHCON(R")$ R", COOR", COR", CONHR", CON(R")R", $CONHSO_2N$ (R")R", NHCOR", N(R")COR", $NHSO_2R"$. $N(R")SO_2R"$, $NH_2R"^+$, $NHR"_2^+$, $NR"_3^+$, wherein R" is H or $C_1$-$C_6$ alkyl, and $CY_3$, wherein Y is F, Cl, or Br.

In accordance with another embodiment, the present invention provides a compound of formula I, as set forth above, wherein $X_1$ is $CF_3$, $X_2$ is H, and $X_3$ is selected from the group consisting of H, $NO_2$, CN and $CF_3$.

In accordance with an embodiment, the present invention provides a compound of formula I, as set forth above, wherein $X_1$ is $CF_3$, $X_2$ is H, and $X_3$ is H.

In accordance with an embodiment, the present invention provides a compound of formula I, as set forth above, wherein $X_1$ is $CF_3$, $X_2$ is H, and $X_3$ is $NO_2$.

In accordance with an embodiment, the present invention provides a compound of formula I, as set forth above, wherein $X_1$ is $CF_3$, $X_2$ is H, and $X_3$ is CN.

In accordance with an embodiment, the present invention provides a compound of formula I, as set forth above, wherein $X_1$ is $CF_3$, $X_2$ is H, and $X_3$ is $CF_3$.

In accordance with another embodiment, the present invention provides a compound of formula I, as set forth above, wherein $X_1$ is $NO_2$, $X_2$ is H, and $X_3$ is selected from the group consisting of H, $NO_2$, CN and $CF_3$.

In accordance with an embodiment, the present invention provides a compound of formula I, as set forth above, wherein $X_1$ is $NO_2$, $X_2$ is H, and $X_3$ is H.

In accordance with a further embodiment, the present invention provides a compound of formula I, as set forth above, wherein $X_1$ is $NO_2$, $X_2$ is H, and $X_3$ is $NO_2$.

In accordance with an embodiment, the present invention provides a compound of formula I, as set forth above, wherein $X_1$ is $NO_2$, $X_2$ is H, and $X_3$ is CN.

In accordance with an embodiment, the present invention provides a compound of formula I, as set forth above, wherein $X_1$ is $NO_2$, $X_2$ is H, and $X_3$ is $CF_3$.

In accordance with another embodiment, the present invention provides a compound of formula I, as set forth above, wherein $X_1$ is H, $X_2$ is H, and $X_3$ is selected from the group consisting of H, $NO_2$, CN and $CF_3$.

In accordance with an embodiment, the present invention provides a compound of formula I, as set forth above, wherein $X_1$ is H, $X_2$ is H, and $X_3$ is H.

In accordance with an embodiment, the present invention provides a compound of formula I, as set forth above, wherein $X_1$ is H, $X_2$ is H, and $X_3$ is $NO_2$.

In accordance with a further embodiment, the present invention provides a compound of formula I, as set forth above, wherein $X_1$ is H, $X_2$ is H, and $X_3$ is CN.

In accordance with an embodiment, the present invention provides a compound of formula I, as set forth above, wherein $X_1$ is H, $X_2$ is H, and $X_3$ is $CF_3$.

In accordance with another embodiment, the present invention provides a compound of formula I, as set forth above, wherein $X_1$ is H, $X_2$ is selected from the group consisting of H, $NO_2$, CN and $CF_3$, and $X_3$ is H.

In accordance with an embodiment, the present invention provides a compound of formula I, as set forth above, wherein $X_1$-$X_3$ are each H.

In accordance with an embodiment, the present invention provides a compound of formula I, as set forth above, wherein $X_1$ and $X_3$ are each H, and $X_2$ is $NO_2$.

In accordance with an embodiment, the present invention provides a compound of formula I, as set forth above, wherein $X_1$ and $X_3$ are each H, and $X_2$ is CN.

In accordance with a further embodiment, the present invention provides a compound of formula I, as set forth above, wherein $X_1$ and $X_3$ are each H, and $X_2$ is $CF_3$.

In accordance with another embodiment, the present invention provides a compound of formula I, as set forth above, wherein $R_1$ to $R_5$ are the same or different and are each selected from the group consisting of H, and OMe; wherein $X_1$ is selected from the group consisting of H, $NO_2$ and $CF_3$; and wherein $X_2$ and $X_3$ are the same or different and are each selected from the group consisting of H, $NO_2$, $CF_3$ and CN.

In accordance with another embodiment, the present invention provides a compound of formula I, as set forth above, wherein $X_1$ is $CF_3$, $X_2$ and $X_3$ are each H, and $R_1$ to $R_5$ are each selected from the group consisting of H and OMe.

In accordance with an embodiment, the present invention provides a compound of formula I, as set forth above, wherein $X_1$ is $CF_3$, $X_2$ and $X_3$ are each H, $R_1$ is OMe, and $R_2$ to $R_5$ are each H.

In accordance with an embodiment, the present invention provides a compound of formula I, as set forth above, wherein $X_1$ is $CF_3$, $X_2$ and $X_3$ are each H, $R_1$ and $R_5$ are each OMe, and $R_2$, $R_3$ and $R_4$ are each H.

In accordance with an embodiment, the present invention provides a compound of formula I, as set forth above, wherein $X_1$ is $CF_3$, $X_2$ and $X_3$ are each H, wherein $R_1$, $R_3$ and $R_5$ are each H, and $R_2$ and $R_4$ are each OMe.

In accordance with a further embodiment, the present invention provides a compound of formula I, as set forth above, wherein $X_1$ is $CF_3$, $X_2$ and $X_3$ are each H, wherein $R_1$, $R_3$ and $R_5$ are each OMe, and $R_2$ and $R_4$ are each H.

In accordance with a further embodiment, the present invention provides a compound of formula I, as set forth above, wherein $X_1$ is $CF_3$, $X_2$ and $X_3$ are each H, wherein $R_2$ and $R_4$ are each OMe, and $R_1$, $R_3$, and $R_5$ are each H.

In accordance with another embodiment, the present invention provides a compound of formula I, as set forth above, wherein $X_1$ and $X_3$ are each H, $X_2$ is CN, $R_1$, $R_2$, $R_3$, and $R_5$ are each selected from the group consisting of H and OMe, and $R_4$ is H.

In accordance with an embodiment, the present invention provides a compound of formula I, as set forth above, wherein $X_1$ and $X_3$ are each H, $X_2$ is CN, $R_1$ and $R_5$ are each OMe, and $R_2$-$R_4$ are each H.

In accordance with an embodiment, the present invention provides a compound of formula I, as set forth above, wherein $X_1$ and $X_3$ are each H, $X_2$ is CN, $R_1$ to $R_3$ are each OMe, and $R_4$ and $R_5$ are each H.

In accordance with an embodiment, the present invention provides a compound of formula I, as set forth above, wherein $X_1$ and $X_3$ are each H, $X_2$ is CN, $R_1$ is OMe, and $R_2$ to $R_5$ are each H.

In accordance with another embodiment, the present invention provides a compound of formula I, as set forth above, wherein $X_1$ and $X_3$ are each $NO_2$, $X_2$ is H, $R_1$ to $R_5$ are each selected from the group consisting of H and OMe.

In accordance with an embodiment, the present invention provides a compound of formula I, as set forth above, wherein $X_1$ and $X_3$ are each $NO_2$, $X_2$ is H, $R_1$ to $R_3$ are each selected from the group consisting of H and OMe, and $R_4$ and $R_5$ are both H.

In accordance with an embodiment, the present invention provides a compound of formula I, as set forth above, wherein $X_1$ and $X_3$ are each $NO_2$, $X_2$ is H, $R_1$ to $R_3$ are each OMe, and $R_4$ and $R_5$ are each H.

In accordance with a further embodiment, the present invention provides a compound of formula I, as set forth above, wherein $X_1$ and $X_3$ are each $NO_2$, $X_2$ is H, $R_1$, $R_2$, $R_4$, and $R_5$ are each H, and $R_3$ is OMe.

In accordance with an embodiment, the present invention provides a compound of formula I, as set forth above, wherein $X_1$ and $X_3$ are each $NO_2$, $X_2$ is H, $R_1$, $R_3$, $R_4$, and $R_5$ are each H, and $R_2$ is OMe.

In accordance with an embodiment, the present invention provides a compound of formula I, as set forth above, wherein $X_1$ and $X_3$ are each $NO_2$, $X_2$ is H, $R_1$ and $R_2$ are each OMe, and $R_3$, $R_4$, and $R_5$ are each H.

In accordance with an embodiment, the present invention provides a compound of formula I, as set forth above, wherein $X_1$ and $X_3$ are each $NO_2$, $X_2$ is H, $R_1$, $R_4$, and $R_5$ are each H, and $R_2$ and $R_3$ are each OMe.

In accordance with an embodiment, the present invention provides a compound of formula I, as set forth above, wherein $X_1$ and $X_3$ are each $NO_2$, $X_2$ is H, $R_1$ is OMe, and $R_2$ to $R_5$ are each H.

In accordance with an embodiment, the present invention provides a compound of formula I, as set forth above, wherein $X_1$ and $X_3$ are each $NO_2$, $X_2$ is H, $R_1$ and $R_4$ are each OMe, and $R_2$, $R_3$ and $R_5$ are each H.

In accordance with an embodiment, the present invention provides a compound of formula I, as set forth above, wherein $X_1$ and $X_3$ are each $NO_2$, $X_2$ is H, $R_2$ and $R_4$ are each OMe, and $R_1$ $R_3$ and $R_5$ are each H.

In accordance with an embodiment, the present invention provides a compound of formula I, as set forth above, wherein $X_1$ and $X_3$ are each $NO_2$, $X_2$ is H, $R_1$, $R_3$ and $R_5$ are each OMe, and $R_2$ and $R_4$ are each H.

In accordance with an embodiment, the present invention provides a compound of formula I, as set forth above, wherein $X_1$ and $X_3$ are each $NO_2$, $X_2$ is H, $R_1$ and $R_5$ are each OMe, and $R_2$, $R_3$, and $R_4$ are each H.

In accordance with another embodiment, the present invention provides a compound of formula I, as set forth above, wherein $X_1$ and $X_3$ are each H, $X_2$ is $CF_3$, and $R_1$ to $R_5$ are each selected from the group consisting of H and OMe.

In accordance with an embodiment, the present invention provides a compound of formula I, as set forth above, wherein $X_1$ and $X_3$ are each H, $X_2$ is $CF_3$, $R_1$ is OMe, and $R_2$ to $R_5$ are each H.

In accordance with an embodiment, the present invention provides a compound of formula I, as set forth above, wherein $X_1$ and $X_3$ are each H, $X_2$ is $CF_3$, $R_2$ is OMe, and $R_1$, $R_3$ to $R_5$ are each H.

In accordance with an embodiment, the present invention provides a compound of formula I, as set forth above, wherein $X_1$ and $X_3$ are each H, $X_2$ is $CF_3$, $R_1$ to $R_3$ are each OMe, and $R_4$ and $R_5$ are each H.

In accordance with an embodiment, the present invention provides a compound of formula I, as set forth above, wherein $X_1$ and $X_3$ are each H, $X_2$ is $CF_3$, $R_2$ and $R_4$ are each OMe, and $R_1$, $R_3$ and $R_5$ are each H.

In accordance with an embodiment, the present invention provides a compound of formula I, as set forth above, wherein $X_1$ and $X_3$ are each H, $X_2$ is $CF_3$, $R_1$ and $R_5$ are each OMe, and $R_2$, $R_3$ and $R_4$ are each H.

In accordance with another embodiment, the present invention provides a compound of formula I, as set forth above, wherein $X_1$ and $X_2$ are each H, $X_3$ is $CF_3$, $R_1$, $R_3$-$R_5$ are each H, and $R_2$ is OMe.

In accordance with an embodiment, the present invention provides a compound of formula I, as set forth above, wherein $X_1$ and $X_2$ are each H, $X_3$ is $CF_3$, $R_1$ and $R_5$ are each OMe, $R_2$ and $R_4$ are each H, and $R_3$ is selected from the group consisting of H and OMe.

In accordance with an embodiment, the present invention provides a compound of formula I, as set forth above, wherein $X_1$ and $X_2$ are each H, $X_3$ is $CF_3$, $R_1$ and $R_5$ are each OMe, $R_2$, $R_3$ and $R_4$ are each H.

In accordance with an embodiment, the present invention provides a compound of formula I, as set forth above, wherein $X_1$ and $X_2$ are each H, $X_3$ is $CF_3$, $R_1$, $R_3$ and $R_5$ are each OMe, and $R_2$, and $R_4$ are each H.

In accordance with another embodiment, the present invention provides a compound of formula I, as set forth above, wherein $X_1$ is $NO_2$, $X_2$ and $X_3$ are each H, $R_1$, $R_2$, $R_4$, and $R_5$ are each selected from the group consisting of H and OMe, and $R_3$ is H.

In accordance with an embodiment, the present invention provides a compound of formula I, as set forth above, wherein $X_1$ is $NO_2$, $X_2$ and $X_3$ are each H, $R_1$, $R_3$, and $R_5$ are each H, and $R_2$ and $R_4$ are each OMe.

In accordance with an embodiment, the present invention provides a compound of formula I, as set forth above, wherein $X_1$ is $NO_2$, $X_2$ and $X_3$ are each H, $R_1$ and $R_4$ are each OMe, and $R_2$, $R_3$, and $R_5$ are each H.

In accordance with an embodiment, the present invention provides a compound of formula I, as set forth above, wherein $X_1$ is $NO_2$, $X_2$ and $X_3$ are each H, $R_1$ and $R_5$ are each OMe, and $R_2$, $R_3$, and $R_4$ are each H.

In accordance with another embodiment, the present invention provides a compound of formula I, as set forth above, wherein $X_1$ and $X_3$ are each H, $X_2$ is $NO_2$, $R_1$, $R_3$, and $R_5$ are each H, and $R_2$ and $R_4$ are each OMe.

In accordance with another embodiment, the present invention provides a compound of formula I, as set forth above, wherein $X_1$ and $X_3$ are each H, $X_2$ is $NO_2$, $R_1$ and $R_5$ are each OMe, and $R_2$, $R_3$, and $R_4$ are each H.

In accordance with another embodiment, the present invention provides a compound of formula I, as set forth above, wherein $X_1$ and $X_2$ are each H, $X_3$ is $NO_2$, $R_1$, $R_3$, and $R_5$ are each H, and $R_2$ and $R_4$ are each OMe.

In another embodiment, the present invention provides the compound, salt, solvate, or stereoisomer of one or more compounds of Formula I, as set forth above, wherein the compound is one of the following:

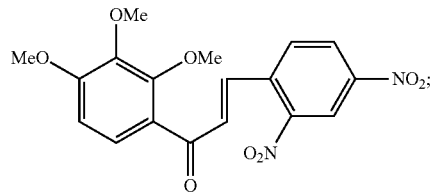

Compound 14

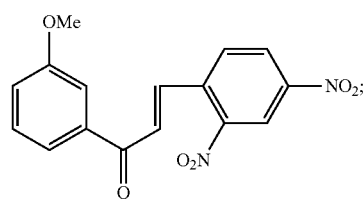

Compound 15

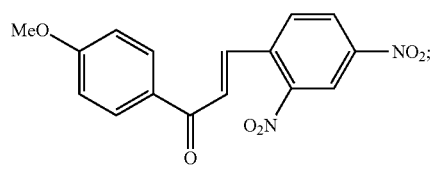

Compound 16

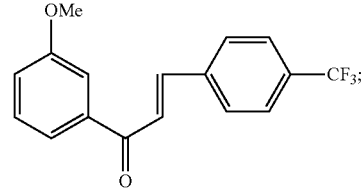

Compound 17

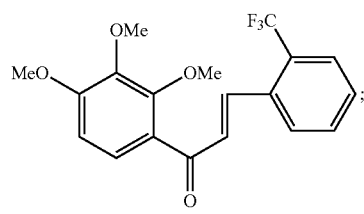

Compound 24

Compound 27
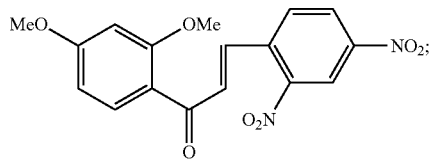
Compound 28
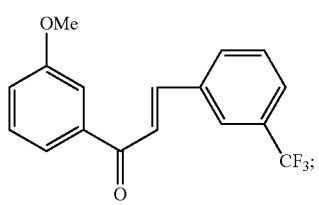
Compound 29
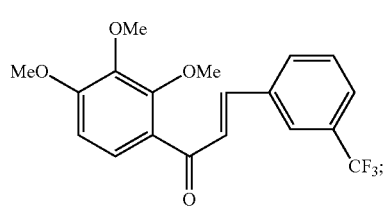
Compound 33
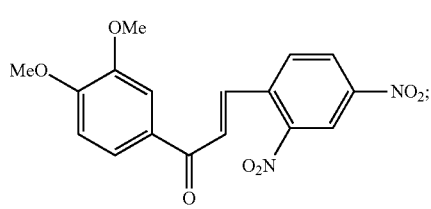
Compound 37
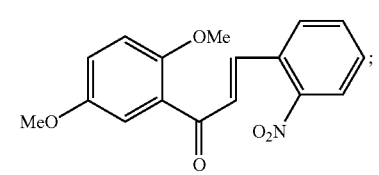
Compound 43
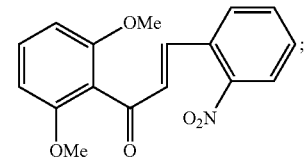
Compound 44
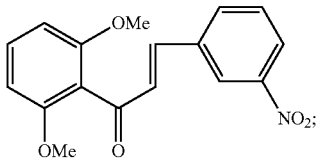
Compound 46
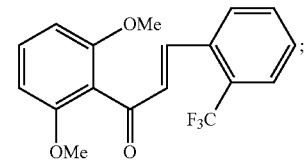
Compound 47
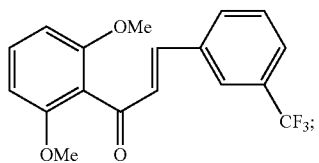
Compound 52
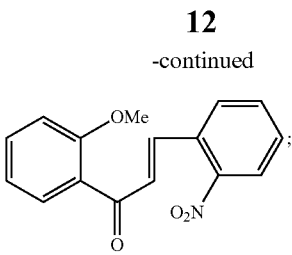
Compound 53
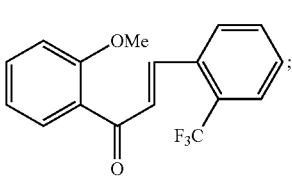
Compound 54
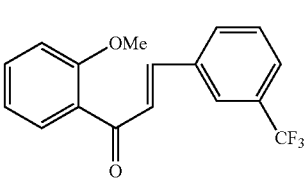
Compound 55
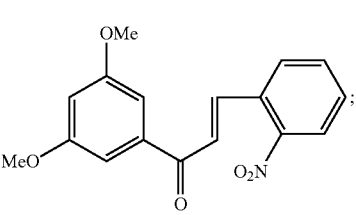
Compound 56
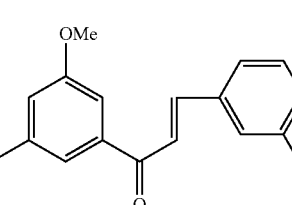
Compound 57
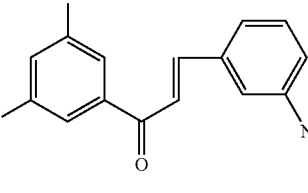
Compound 58
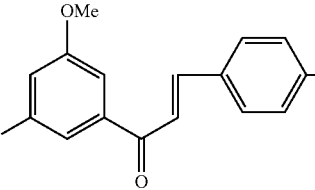
Compound 59
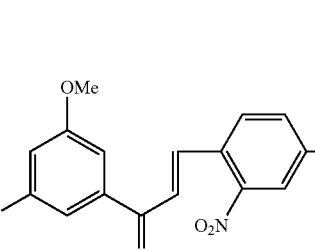

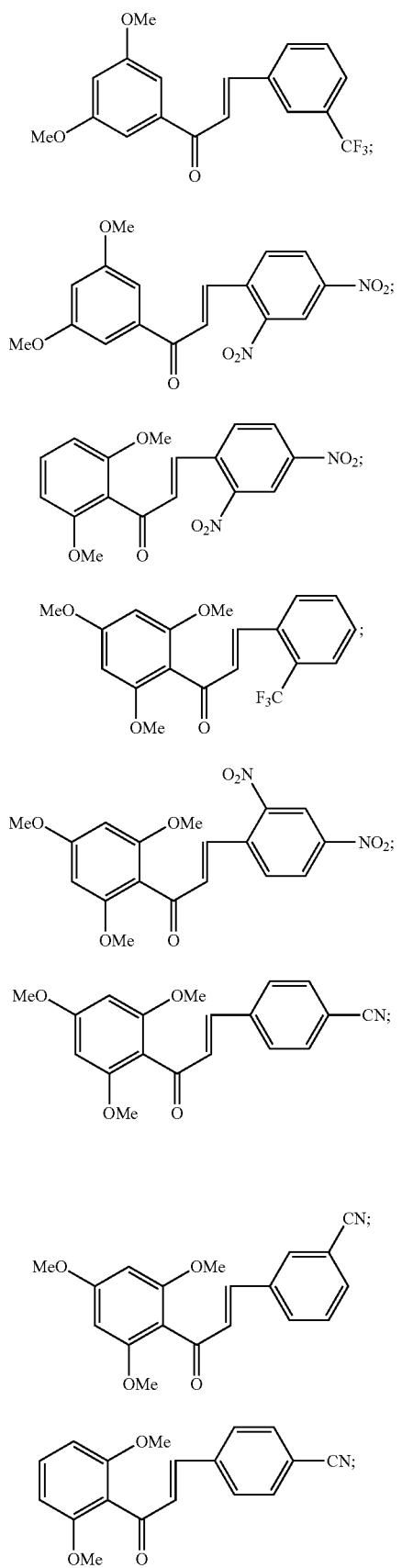

Compound 60

Compound 61

Compound 62

Compound 88

Compound 93

Compound 94

Compound 99

Compound 102

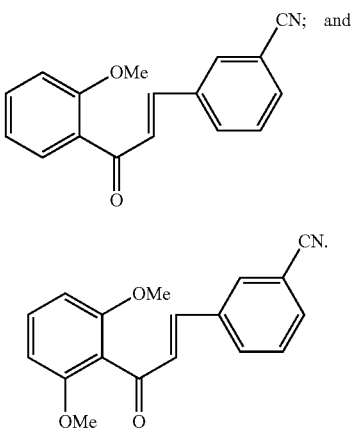

Compound 110

Compound 115

In a further embodiment, the present invention provides a pharmaceutical composition comprising a compound, salt, solvate, or stereoisomer of any one of the compounds of Formula I, as set forth above, and a pharmaceutically acceptable carrier.

In another embodiment, the present invention provides a pharmaceutical composition comprising a compound, salt, solvate, or stereoisomer of any one of the compounds of Formula I, as set forth above, and at least one or more other antiandrogen compounds, and a pharmaceutically acceptable carrier.

In another embodiment, the present invention provides a pharmaceutical composition comprising a compound, salt, solvate, or stereoisomer of any one of the compounds of Formula I, as set forth above, and at least one or more other anticancer compounds, and a pharmaceutically acceptable carrier.

In an embodiment, the present invention provides that the other anticancer compounds can be, for example, anticancer drugs from the following drug classes, including, but not limited to, antimitoics, antineoplastics, antimetabolites, and alkylating agents. Such classes of anticancer drugs are well known in the art.

In accordance with an embodiment of the present invention, the exclusion of compounds included within the proviso of Formula I, as set forth above, does not apply to the methods of treatment and/or use described herein. Therefore, in accordance with another embodiment of the invention, the present invention provides a method of treating or preventing cancer in a subject comprising administering to the subject an effective amount of a compound, salt, solvate, or stereoisomer of any one the compounds of Formula I:

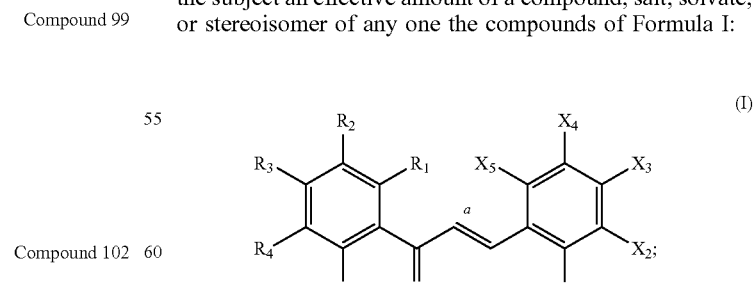

(I)

wherein $R_1$ to $R_5$ are the same or different and are each selected from the group consisting of H, $C_1$-$C_6$ alkyl, $C_2$-$C_6$ alkenyl, $C_2$-$C_6$ alkynyl, $C_1$-$C_6$ hydroxyalkyl, $C_1$-$C_6$ alkoxy, $C_1$-$C_6$ alkoxy $C_1$-$C_6$ alkyl, $C_1$-$C_6$ alkylamino, di-$C_1$-$C_6$ alkylamino, $C_1$-$C_6$ dialkylamino $C_1$-$C_6$ alkyl, $C_1$-$C_6$ thioalkyl, $C_2$-$C_6$ thioalkenyl, $C_2$-$C_6$ thioalkynyl, $C_6$-$C_{22}$ aryloxy, $C_2$-$C_6$ acyloxy, $C_2$-$C_6$ thioacyl, $C_1$-$C_6$ amido, and $C_1$-$C_6$ sulphonamido; wherein $X_1$ to $X_5$ are the same or different and are each selected from the group consisting of H and electron withdrawing groups; and wherein bond "a" can be in either the E or Z form, or a pharmaceutically acceptable salt thereof.

In accordance with another embodiment, the present invention provides a method of treating or preventing cancer in a subject comprising administering to the subject an effective amount of a compound, salt, solvate, or stereoisomer of any one the following:

Compound 1

Compound 2

Compound 3

Compound 4

Compound 5

Compound 6

Compound 7

Compound 8

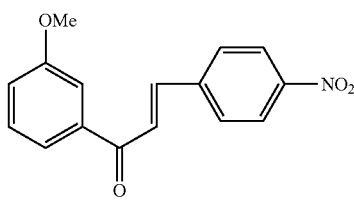

Compound 9

Compound 10

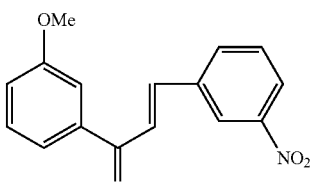

Compound 11

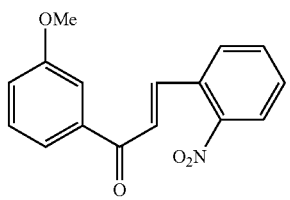

Compound 12

Compound 13

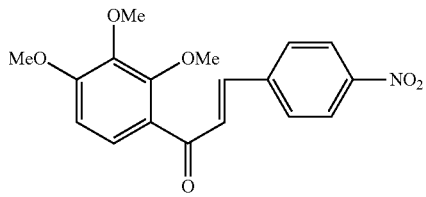

Compound 14

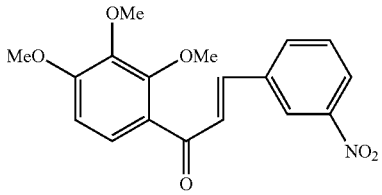

Compound 15

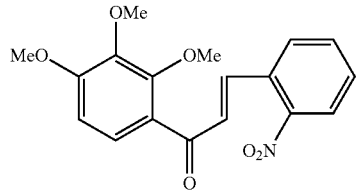

Compound 16
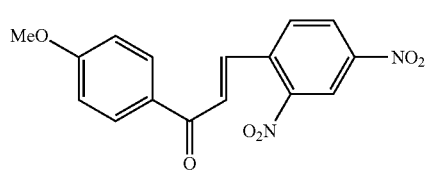
Compound 17
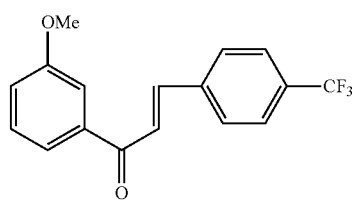
Compound 18
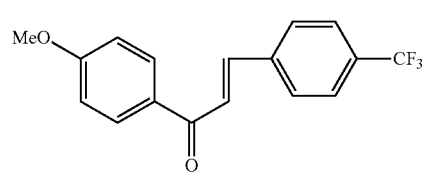
Compound 19
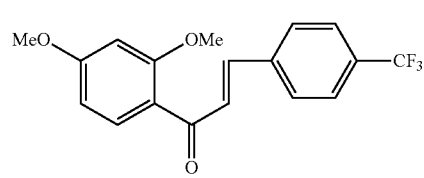
Compound 20
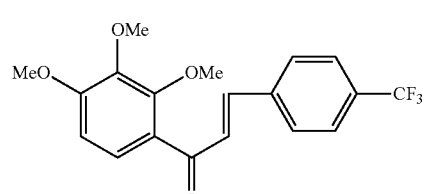
Compound 21
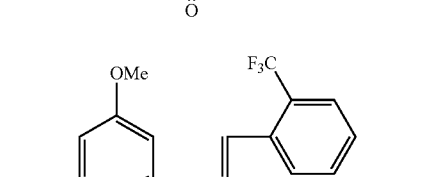
Compound 22
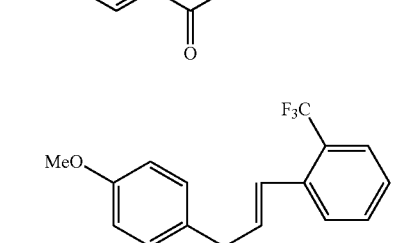
Compound 23
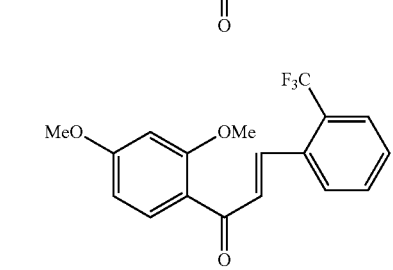
Compound 24
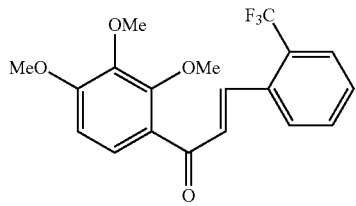
Compound 25
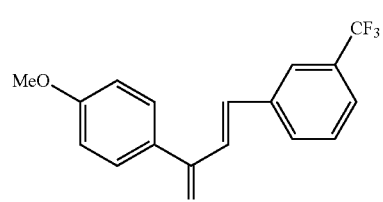
Compound 26
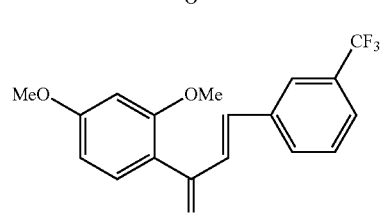
Compound 27
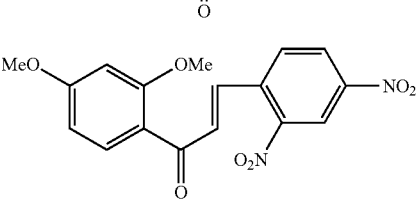
Compound 28
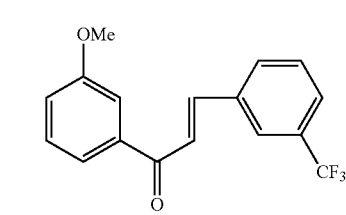
Compound 29
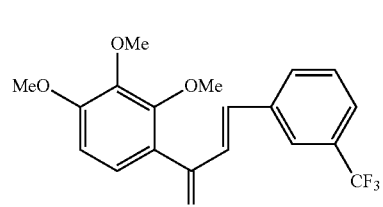
Compound 30
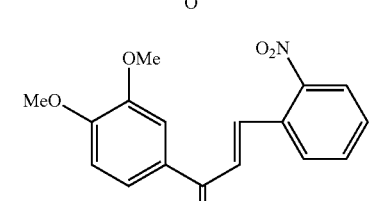
Compound 31
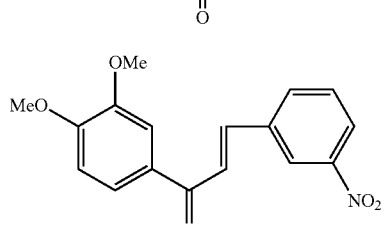

Compound 32
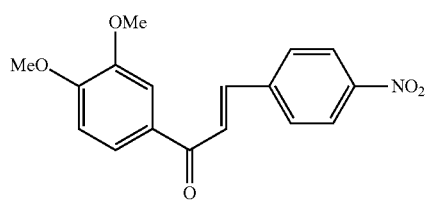
Compound 33
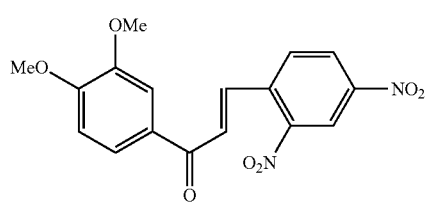
Compound 34
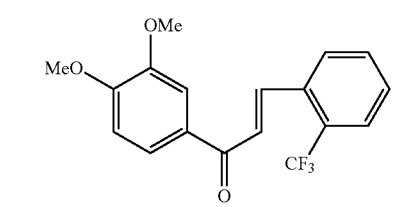
Compound 35
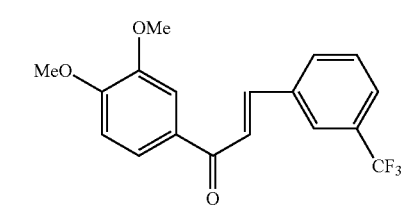
Compound 36
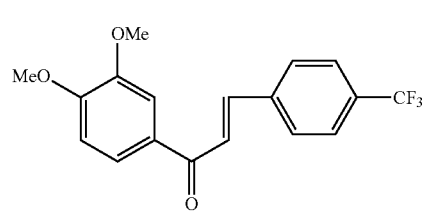
Compound 37
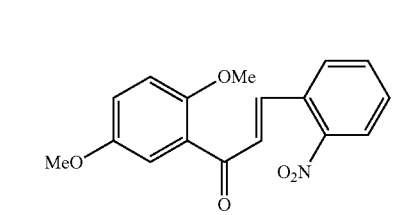
Compound 38
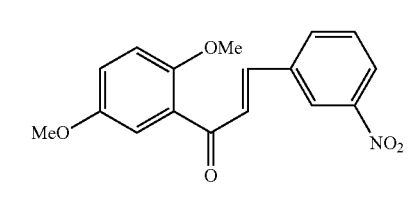
Compound 39
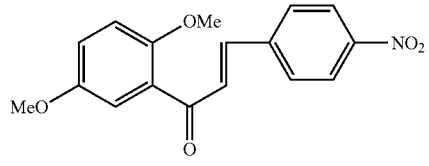
Compound 40
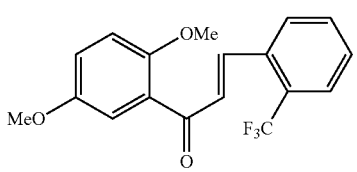
Compound 41
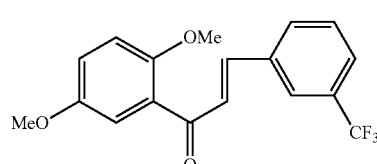
Compound 42
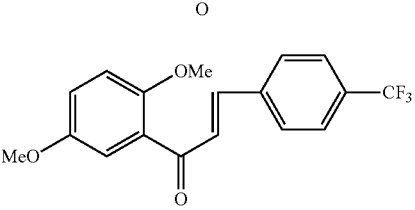
Compound 43
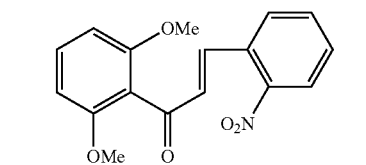
Compound 44
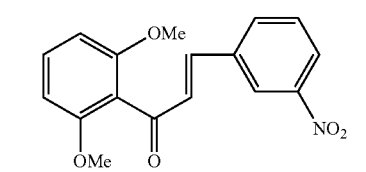
Compound 45
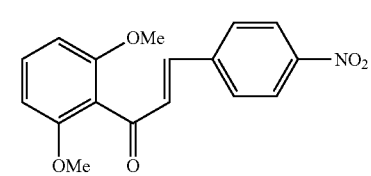
Compound 46
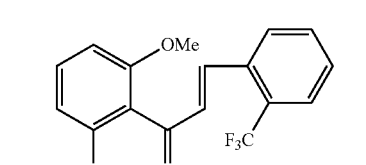
Compound 47
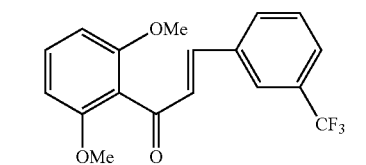
Compound 48
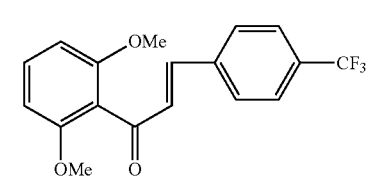

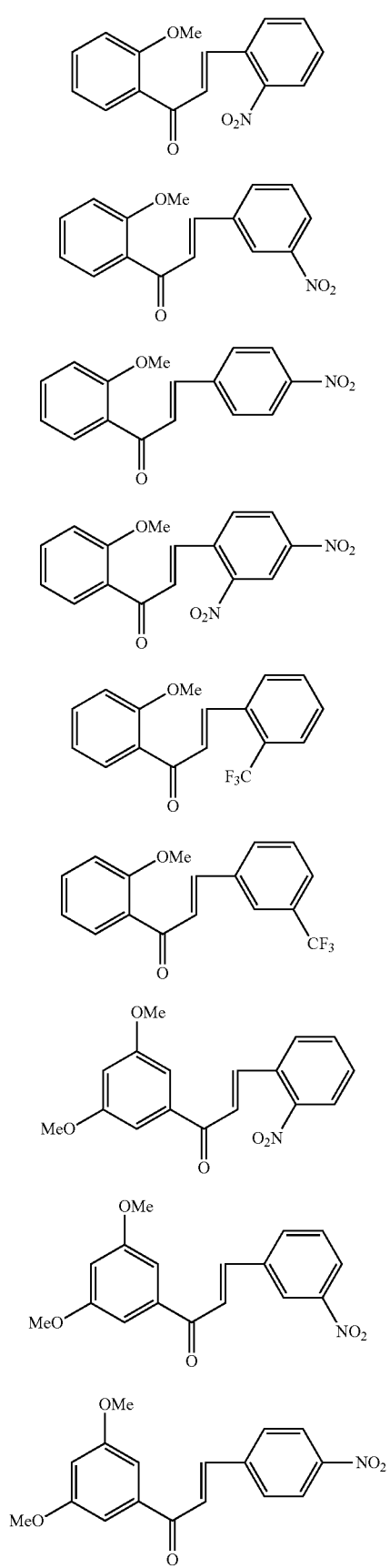
Compound 49
Compound 50
Compound 51
Compound 52
Compound 53
Compound 54
Compound 55
Compound 56
Compound 57
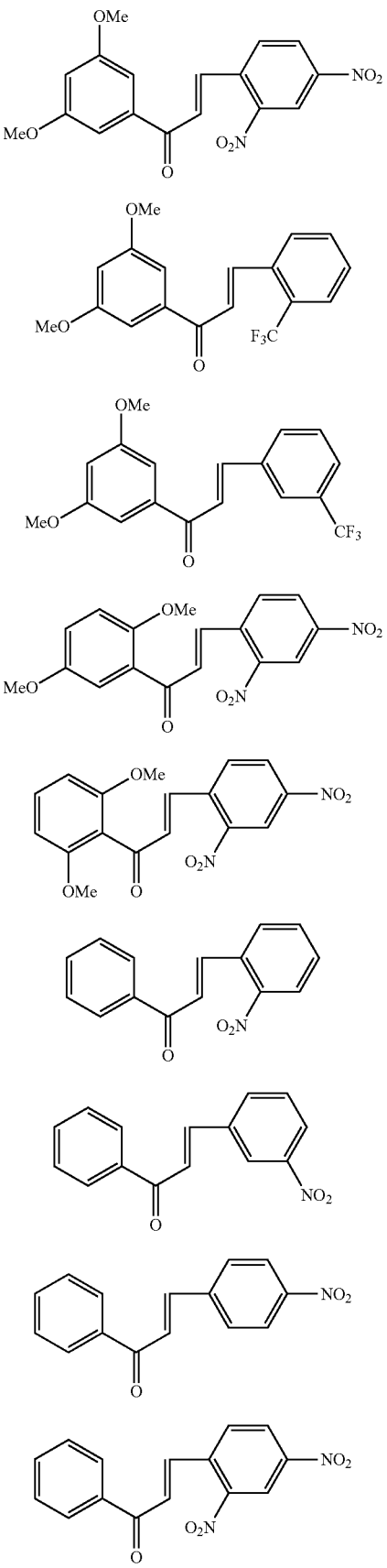
Compound 58
Compound 59
Compound 60
Compound 61
Compound 62
Compound 63
Compound 64
Compound 65
Compound 66

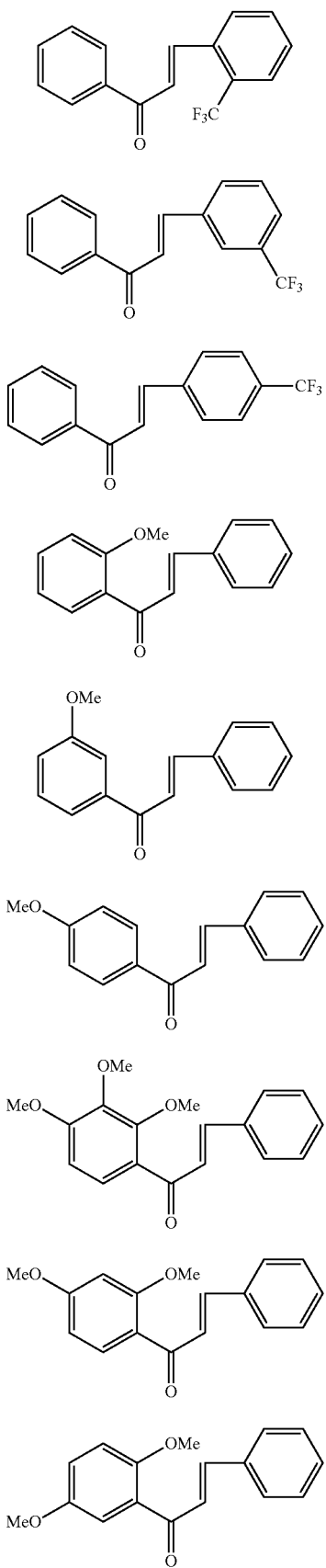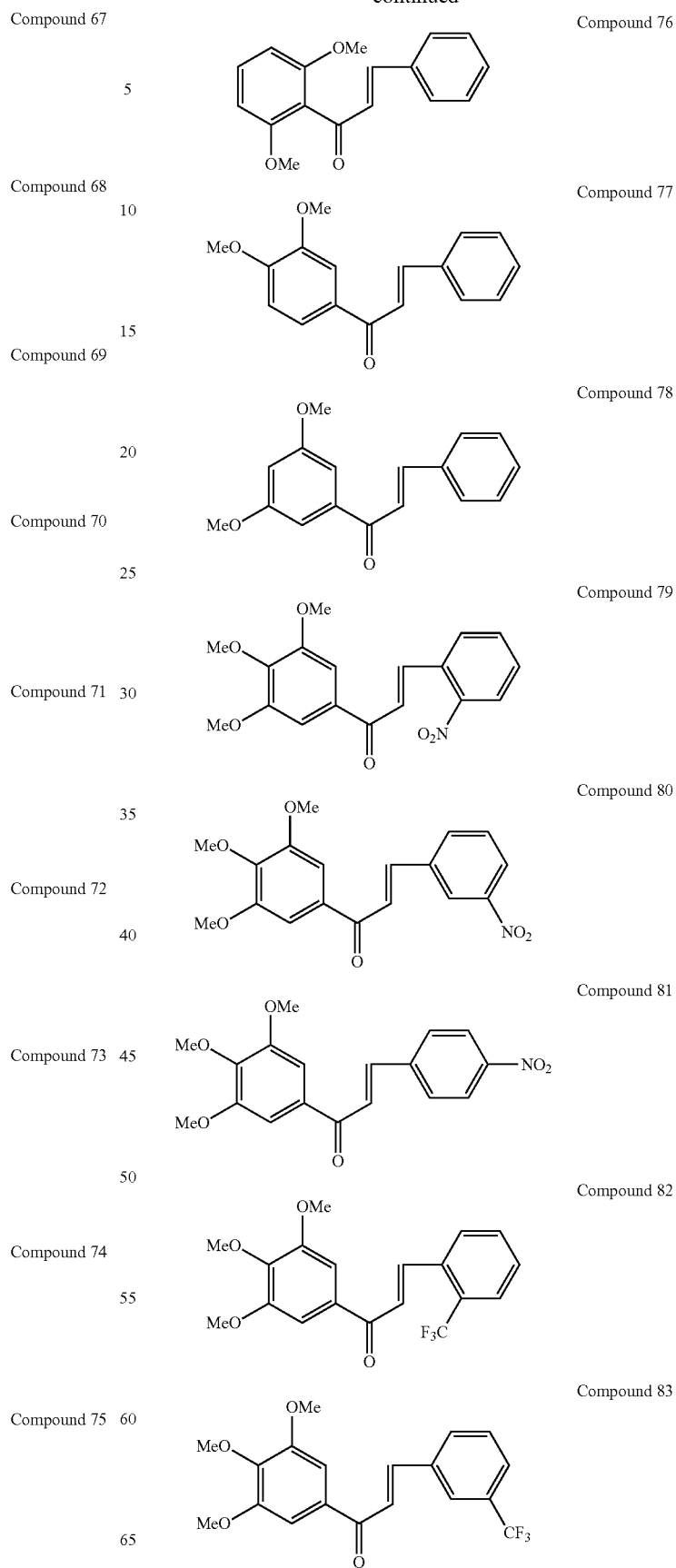

Compound 84
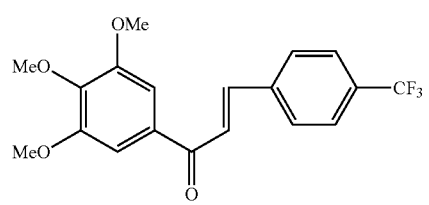
Compound 85
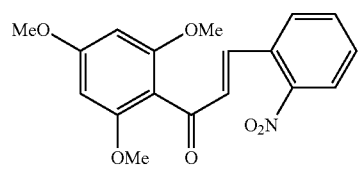
Compound 86
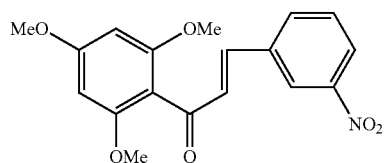
Compound 87
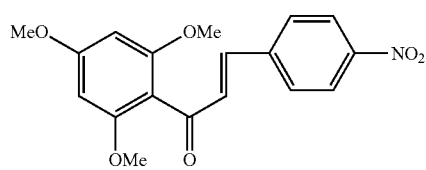
Compound 88
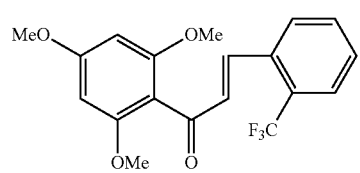
Compound 89
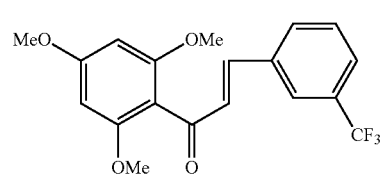
Compound 90
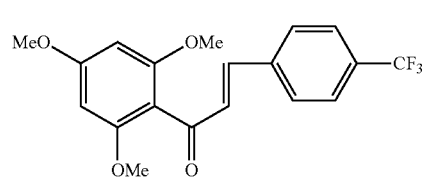
Compound 91
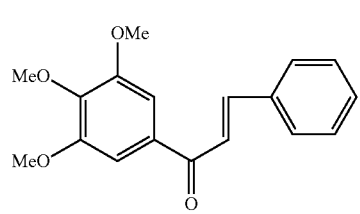
Compound 92
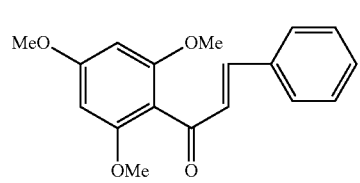
Compound 93
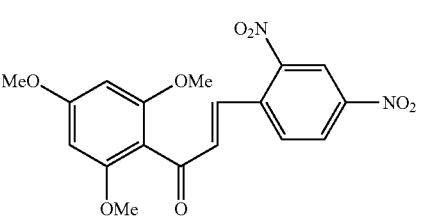
Compound 94
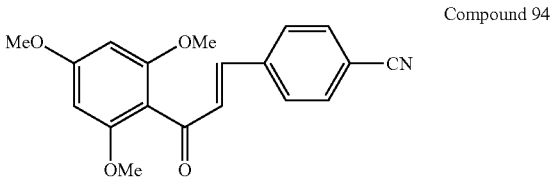
Compound 95
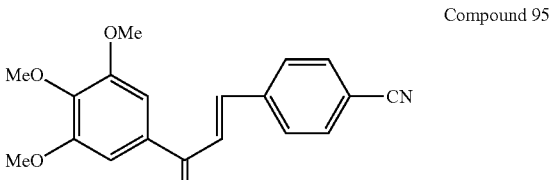
Compound 96
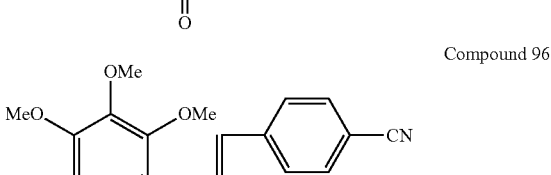
Compound 97
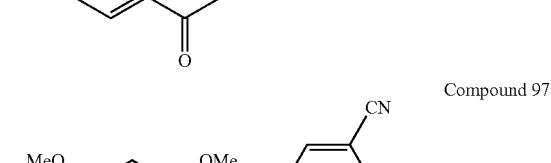
Compound 98
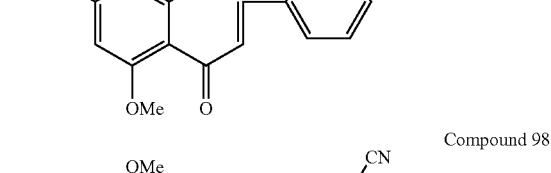
Compound 99
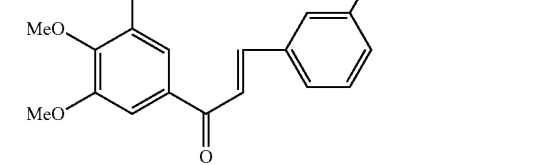
Compound 100
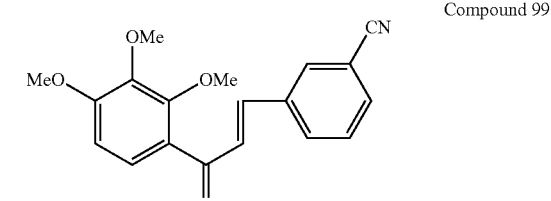

Compound 101
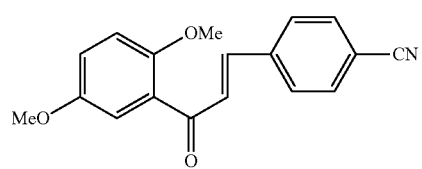
Compound 102
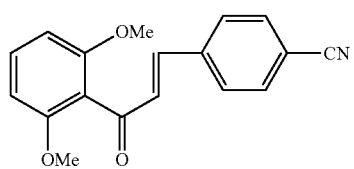
Compound 103
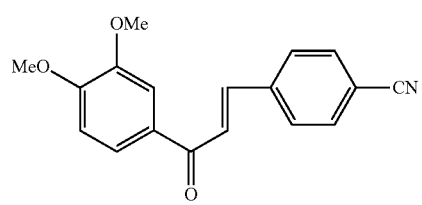
Compound 104
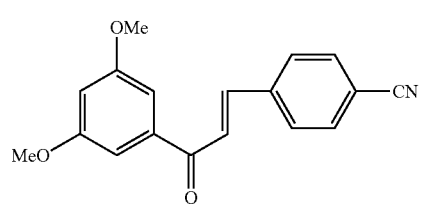
Compound 105
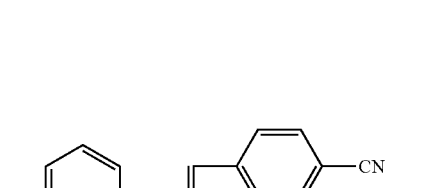
Compound 106
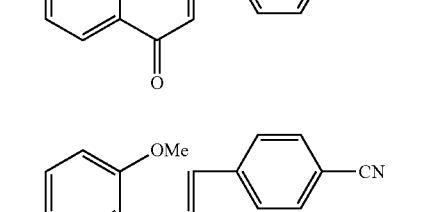
Compound 107
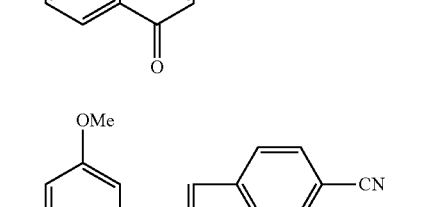
Compound 108
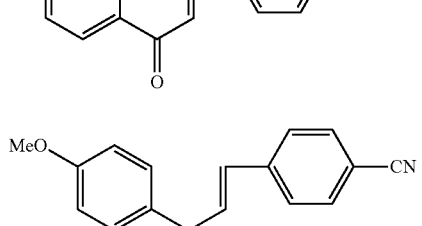
Compound 109
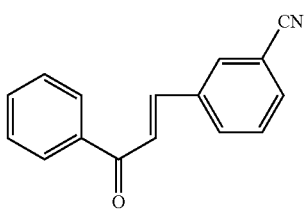
Compound 110
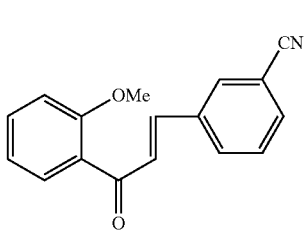
Compound 111
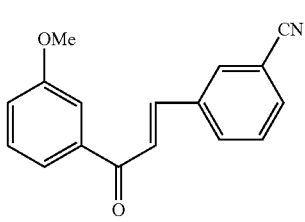
Compound 112
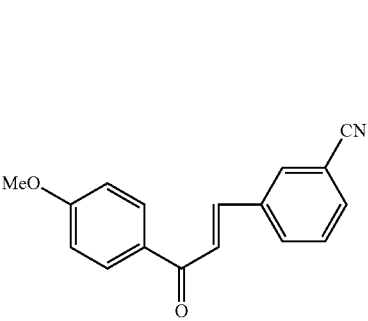
Compound 113
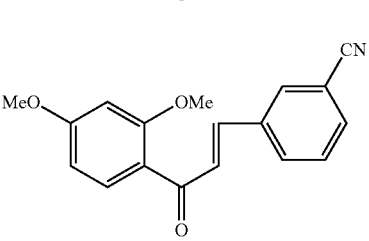
Compound 114
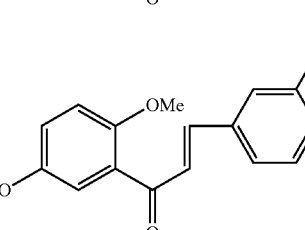
Compound 115
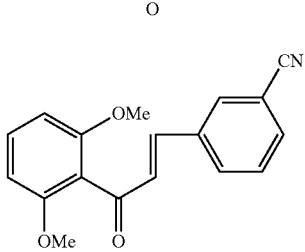

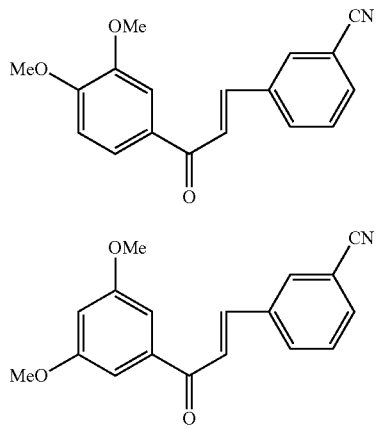

Compound 116

Compound 117

In a further embodiment, the type of cancer being treated with the compounds of the present invention include prostate cancer, AR-dependent cancers, AR-independent cancers, androgen-independent AR-dependent cancers and castrate resistant prostate cancer.

In an embodiment, the present invention provides a method of inhibiting AR activation in a subject comprising administering to the subject an effective amount of a compound, salt, solvate, or stereoisomer of any one the compounds of Formula I, as set forth above.

In accordance with an embodiment of the invention, the present invention also provides a method of inducing AR degradation in a prostate cancer cell of a subject comprising administering to the subject an effective amount of a compound, salt, solvate, or stereoisomer of any one the compounds of Formula I, as set forth above.

In another embodiment, the present invention provides a method of inhibiting AR activation in a subject, comprising administering to the subject an effective amount of a compound, salt, solvate, or stereoisomer of any one the compounds of Formula I, as set forth above.

In another embodiment, the present invention provides a method of inhibiting androgen-independent AR activation in a subject, comprising administering to the subject an effective amount of a compound, salt, solvate, or stereoisomer of any one the compounds of Formula I, as set forth above.

Type I nuclear receptors, of which androgen receptors are included, also include other sex steroid binding receptors, including, for example, progesterone receptors, and estrogen receptors. In accordance with an embodiment, the present invention provides a method of modulating nuclear receptors in a subject, comprising administering to a subject an effective amount of a compound, salt, solvate, or stereoisomer of any one the compounds of Formula I, as set forth above.

In a further embodiment, the present invention provides a method of inhibiting progesterone receptor and/or estrogen receptor activation in a subject, comprising administering to the subject an effective amount of a compound, salt, solvate, or stereoisomer of any one the compounds of Formula I, as set forth above.

In an embodiment, the present invention also provides a method of inducing AR degradation in a prostate cancer cell of a subject, comprising administering to the subject an effective amount of a compound, salt, solvate, or stereoisomer of any one the compounds of Formula I, as set forth above.

In an embodiment, the present invention also provides a method of inhibiting the growth of a cancer cell or tumor cell in vitro comprising contacting the cancer cell or tumor cell with an effective amount of a compound, salt, solvate, or stereoisomer of any one the compounds of Formula I, as set forth above.

In accordance with the present invention, the terms "AR-dependent cancer," "androgen-independent AR-dependent cancer" and "AR-independent cancer" are included within the term "prostate cancer." It is known that AR is also expressed in bladder, lung, breast, hepatocellular, colon, ovarian carcinomas, etc., and may be involved in these cancers as well.

It is also contemplated, in accordance with the present invention, in an embodiment, that the present invention provides a method of inhibiting expression of PSA mRNA in prostate cancer cells by contacting the cells with an effective amount of a compound, salt, solvate, or stereoisomer of any one the compounds of Formula I, as set forth above.

In accordance with the present invention, the term "prostate cancer" also includes any cancers related to cells of the prostate gland and associated tissues, and also includes castrate-resistant prostate cancer.

It was also found, in accordance with the present invention that the present invention provides a method of inhibition of androgen stimulated AR gene expression in prostate cancer cells, by contacting the cells with an effective amount of a compound, salt, solvate, or stereoisomer of any one the compounds of Formula I, as set forth above.

In accordance with the present invention, and without being bound to any particular theory, it is thought that contacting the cancer cells with AR-dependent or AR-independent cancer cell with an effective amount of a compound, salt, solvate, or stereoisomer of any one the compounds of Formula I, as set forth above, can result in inhibition of AR translocation in the nucleus, the blocking of the dissociation of AR-Hsp90 complex, and/or initiate the loss of AR expression in the treated cells, any of which can result in cell apoptosis and/or cell death of the cells contacted.

In addition, in accordance with the present invention, and without being bound to any particular theory, it has been found that the compounds of Formula I, as set forth above, appear to specifically bind Heat Shock Protein 40 kD (Hsp40) and modulates it activity in the cell. In an embodiment, the present invention provides a method of modulating or decreasing the Hsp40 activity in a subject, and/or a cancer cell, comprising administering to the subject and/or cancer cell, an effective amount of a compound, salt, solvate, or stereoisomer of any one the compounds of Formula I, as set forth above.

As used herein, examples of the term "alkyl" preferably include a $C_{1-6}$ alkyl (e.g., methyl, ethyl, propyl, isopropyl, butyl, isobutyl, sec-butyl, tert-butyl, pentyl, hexyl, etc.) and the like.

As used herein, examples of the term "alkenyl" preferably include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, etc.) and the like.

As used herein, examples of the term "alkynyl" preferably include $C_{2-6}$ alkynyl (e.g., ethynyl, propargyl, 1-butynyl, 2-butynyl, 3-butynyl, 1-hexynyl, etc.) and the like.

Examples of the term "cycloalkyl" preferably include a $C_{3-8}$ cycloalkyl (e.g., a cyclopropyl, cyclobutyl, cyclopentyl, cyclohexyl, etc.) and the like.

Examples of the term "aryl" preferably include a $C_{6-14}$ aryl (e.g., a phenyl, 1-naphthyl, a 2-naphthyl, 2-biphenylyl group, 3-biphenylyl, 4-biphenylyl, 2-anthracenyl, etc.) and the like.

Examples of the term "arylalkyl" preferably include a $C_{6-14}$ arylalkyl (e.g., benzyl, phenylethyl, diphenylmethyl, 1-naphthylmethyl, 2-naphthylmethyl, 2,2-diphenylethyl, 3-phenylpropyl, 4-phenylbutyl, 5-phenylpentyl, etc.) and the like.

The term "hydroxyalkyl" embraces linear or branched alkyl groups having one to about ten carbon atoms any one of which may be substituted with one or more hydroxyl groups.

The term "alkylamino" includes monoalkylamino. The term "monoalkylamino" means an amino, which is substituted with an alkyl as defined herein. Examples of monoalkylamino substituents include, but are not limited to, methylamino, ethylamino, isopropylamino, t-butylamino, and the like. The term "dialkylamino" means an amino, which is substituted with two alkyls as defined herein, which alkyls can be the same or different. Examples of dialkylamino substituents include dimethylamino, diethylamino, ethylisopropylamino, diisopropylamino, dibutylamino, and the like.

The terms "alkylthio," "alkenylthio" and "alkynylthio" mean a group consisting of a sulphur atom bonded to an alkyl-, alkenyl- or alkynyl-group, which is bonded via the sulphur atom to the entity to which the group is bonded.

In the compounds disclosed herein, including, e.g., the compounds of Formula I, and their salts, solvates, or stereoisomers thereof, the group represented by $X_1$ to $X_5$ may be H or an electron withdrawing group, including $N_3$, CN, $NO_2$, CHO, NCS, SCN, F, Cl, Br, I, $OCF_3$, $SO_3H$, $B(OH)_2$, $PO(OH)_2$, $PO(OH)(OR")$, $PO(OR")_2$, $SO_2NHOH$, $SO_2NH_2$, $CONH_2$, CONHOH, SR", SOR", $SO_2R"$, $SO_2NHR"$, $SO_2N(R")R"$, $SO_2NHCON(R")R"$, COOR", COR", CONHR", $CON(R")R"$, $CONHSO_2N(R")R"$, NHCOR", $N(R")COR"$, $NHSO_2R"$. $N(R")SO_2R"$, $NH_2R"^+$, $NHR"_2^+$, $NR"_3^+$, wherein R" is H or $C_1$-$C_6$ alkyl, and $CY_3$, wherein Y is F, Cl, or Br.

Accordingly, included within the compounds of the present invention are the tautomeric forms of the disclosed compounds, isomeric forms including enantiomers, stereoisomers, and diastereoisomers, and the pharmaceutically-acceptable salts thereof. The term "pharmaceutically acceptable salts" embraces salts commonly used to form alkali metal salts and to form addition salts of free acids or free bases. Examples of acids which may be employed to form pharmaceutically acceptable acid addition salts include such inorganic acids as hydrochloric acid, sulphuric acid and phosphoric acid, and such organic acids as maleic acid, succinic acid and citric acid. Other pharmaceutically acceptable salts include salts with alkali metals or alkaline earth metals, such as sodium, potassium, calcium and magnesium, or with organic bases, such as dicyclohexylamine. Suitable pharmaceutically acceptable salts of the compounds of the present invention include, for example, acid addition salts which may, for example, be formed by mixing a solution of the compound according to the invention with a solution of a pharmaceutically acceptable acid, such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. All of these salts may be prepared by conventional means by reacting, for example, the appropriate acid or base with the corresponding compounds of the present invention.

Salts formed from free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

For use in medicines, the salts of the compounds of the present invention should be pharmaceutically acceptable salts. Other salts may, however, be useful in the preparation of the compounds according to the invention or of their pharmaceutically acceptable salts.

In addition, embodiments of the invention include hydrates of the compounds of the present invention. The term "hydrate" includes but is not limited to hemihydrate, monohydrate, dihydrate, trihydrate and the like. Hydrates of the compounds of the present invention may be prepared by contacting the compounds with water under suitable conditions to produce the hydrate of choice.

The pharmaceutical compositions of the present invention are suitably used as therapeutic agents for AR-dependent and/or AR-independent prostate cancers, androgen-independent AR-dependent prostate cancers, and related disorders. According to another embodiment of the present invention, a method is provided for treating or preventing AR-dependent and/or AR-independent prostate cancers, androgen-independent AR-dependent prostate cancers, and related disorders in a subject, comprising administering to the subject, at least one compound, salt, solvate, or stereoisomer of any one the compounds of Formula I, as set forth above, in an amount effective to treat or prevent the AR-dependent and/or AR-independent prostate cancers, androgen-independent AR-dependent prostate cancers, and related disorders in the subject.

Accordingly, in a further embodiment, one or more compounds, salts, solvates, or stereoisomers of any one the compounds of Formula I, as set forth above, are suitably used as therapeutic agents for AR-dependent and/or AR-independent prostate cancers and related disorders, in conjunction with one or more antiandrogen compounds, in an amount effective to treat or prevent the AR-dependent and/or AR-independent prostate cancers and related disorders in the subject.

As defined herein, "antiandrogen compounds" include any compound which can act as an androgen hormone receptor antagonist and/or are capable of preventing or inhibiting the biologic effects of androgens, or male sex hormones on androgen receptors, and functional portions thereof. Examples of antiandrogen compounds include, but are not limited to, spironolactone, cyproterone acetate, flutamide, ketoconazole, finasteride, bexlosteride, izonsteride, epristeride, turosteride, R1881 (methyltrienolone), nilutamide, bicalutamide, MDV3100 (4-(3-(4-cyano-3-(trifluoromethyl)phenyl)-5,5-dimethyl-4-oxo-2-thioxoimidazolidin-1-yl)-2-fluoro-N-methylbenzamide), BMS-641988, YM-580, DIMP, abiraterone acetate, VN/124-1, dutasteride, FCE 28260, SKF 105111, apoptone (HE3235), TAK-700, and ARN-509.

As defined herein, in one or more embodiments, "contacting" means that the one or more compounds of the present invention are introduced into a sample having at least one cancer cell expressing a type I nuclear receptor, such as, for example, an AR, or AR complex, and appropriate enzymes or reagents, in a test tube, flask, tissue culture, chip, array, plate, microplate, capillary, or the like, and incubated at a temperature and time sufficient to permit binding of the at least one compound to the AR, or AR complex of the cancer cell. Methods for contacting the samples with the compounds, and other specific binding components are known to those skilled in the art, and may be selected depending on the type of assay protocol to be run. Incubation methods are also standard and are known to those skilled in the art.

In another embodiment, the term "contacting" means that the at least one compound of the present invention is introduced into a subject, preferably a subject receiving treatment for a AR-dependent or AR-independent disorder, such as prostate cancer, and the at least one compounds is allowed to come in contact with the AR or AR complex in vivo.

In an embodiment, the pharmaceutical compositions of the present invention comprise the compounds of the present invention, for example, the compounds of Formula I, and/or their salts, solvates or stereoisomers thereof, and optionally, one or more other antiandrogen or anticancer compounds, together with a pharmaceutically acceptable carrier.

Embodiments of the invention also include a process for preparing pharmaceutical products comprising the compounds. The term "pharmaceutical product" means a composition suitable for pharmaceutical use (pharmaceutical composition), as defined herein. Pharmaceutical compositions formulated for particular applications comprising the compounds of the present invention are also part of this invention, and are to be considered an embodiment thereof.

As used herein, the term "modulate," as well as words stemming therefrom, can mean effecting a change in the function or operation of a protein or a biological process. The term "modulate" can also be used to mean an upregulation, or a downregulation of expression of a gene product. Furthermore, the term "modulate" can also mean to increase or decrease the endogenous activity of a protein in a cell, or in a cellular process. For example, the binding of compound to a protein, such as a receptor, for example, can alter the affinity of the receptor for binding its endogenous ligand, which can change how it interacts with other cellular proteins.

As used herein, the term "treat," as well as words stemming therefrom, includes preventative as well as disorder remitative treatment. The terms "reduce," "suppress," "prevent," and "inhibit," as well as words stemming therefrom, have their commonly understood meaning of lessening or decreasing. These words do not necessarily imply 100% or complete treatment, reduction, suppression, or inhibition.

With respect to pharmaceutical compositions described herein, the pharmaceutically acceptable carrier can be any of those conventionally used, and is limited only by physico-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. Examples of the pharmaceutically acceptable carriers include soluble carriers such as known buffers which can be physiologically acceptable (e.g., phosphate buffer) as well as solid compositions such as solid-state carriers or latex beads. It is preferred that the pharmaceutically acceptable carrier be one which is chemically inert to the active agent(s), and one which has little or no detrimental side effects or toxicity under the conditions of use.

The carriers or diluents used herein may be solid carriers or diluents for solid formulations, liquid carriers or diluents for liquid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

For liquid formulations, pharmaceutically acceptable carriers may be, for example, aqueous or non-aqueous solutions, suspensions, emulsions or oils. Examples of non-aqueous solvents are propylene glycol, polyethylene glycol, and injectable organic esters such as ethyl oleate. Aqueous carriers include, for example, water, alcoholic/aqueous solutions, cyclodextrins, emulsions or suspensions, including saline and buffered media.

Examples of oils are those of petroleum, animal, vegetable, or synthetic origin, for example, peanut oil, soybean oil, mineral oil, olive oil, sunflower oil, fish-liver oil, sesame oil, cottonseed oil, corn oil, olive, petrolatum, and mineral. Suitable fatty acids for use in parenteral formulations include, for example, oleic acid, stearic acid, and isostearic acid. Ethyl oleate and isopropyl myristate are examples of suitable fatty acid esters.

Parenteral vehicles (for subcutaneous, intravenous, intraarterial, or intramuscular injection) include, for example, sodium chloride solution, Ringer's dextrose, dextrose and sodium chloride, lactated Ringer's and fixed oils. Formulations suitable for parenteral administration include, for example, aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

Intravenous vehicles include, for example, fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions.

In addition, in an embodiment, the compounds of the present invention may further comprise, for example, binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweetners (e.g., aspartame, citric acid), preservatives (e.g., thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates), and/or adjuvants.

The choice of carrier will be determined, in part, by the particular compound, as well as by the particular method used to administer the compound. Accordingly, there are a variety of suitable formulations of the pharmaceutical composition of the invention. The following formulations for parenteral, subcutaneous, intravenous, intramuscular, intraarterial, intrathecal and interperitoneal administration are exemplary, and are in no way limiting. More than one route can be used to administer the compounds, and in certain instances, a particular route can provide a more immediate and more effective response than another route.

Suitable soaps for use in parenteral formulations include, for example, fatty alkali metal, ammonium, and triethanolamine salts, and suitable detergents include, for example, (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25% by weight of the compounds in solution. Preservatives and buffers may be used. In order to minimize or eliminate irritation at the site of injection, such compositions may contain one or more nonionic surfactants, for example, having a hydrophile-lipophile balance (HLB) of from about 12 to about 17. The quantity of surfactant in such formulations will typically range from about 5% to about 15% by weight. Suitable surfactants include, for example, polyethylene glycol sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Injectable formulations are in accordance with the invention. The requirements for effective pharmaceutical carriers for injectable compositions are well-known to those of ordinary skill in the art (see, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Trissel, 15th ed., pages 622-630 (2009)).

For purposes of the invention, the amount or dose of the compounds, salts, solvates, or stereoisomers of any one the compounds of Formula I, as set forth above, administered should be sufficient to effect, e.g., a therapeutic or prophylactic response, in the subject over a reasonable time frame. The dose will be determined by the efficacy of the particular compound and the condition of a human, as well as the body weight of a human to be treated.

The dose of the compounds, salts, solvates, or stereoisomers of any one the compounds of Formula I, as set forth above, of the present invention also will be determined by the existence, nature and extent of any adverse side effects that might accompany the administration of a particular compound. Typically, an attending physician will decide the dosage of the compound with which to treat each individual patient, taking into consideration a variety of factors, such as age, body weight, general health, diet, sex, compound to be administered, route of administration, and the severity of the condition being treated. By way of example, and not intending to limit the invention, the dose of the compound can be about 0.001 to about 1000 mg/kg body weight of the subject being treated/day, from about 0.01 to about 100 mg/kg body weight/day, about 0.1 mg to about 10 mg/kg body weight/day.

Alternatively, the compounds of the present invention can be modified into a depot form, such that the manner in which the compound is released into the body to which it is administered is controlled with respect to time and location within the body (see, for example, U.S. Pat. No. 4,450,150). Depot forms of compounds can be, for example, an implantable composition comprising the compound and a porous or non-porous material, such as a polymer, wherein the compound is encapsulated by or diffused throughout the material and/or degradation of the non-porous material. The depot is then implanted into the desired location within the body and the compounds are released from the implant at a predetermined rate.

In one embodiment, the compounds of the present invention provided herein can be controlled release compositions, i.e., compositions in which the one or more compounds are released over a period of time after administration. Controlled or sustained release compositions include formulation in lipophilic depots (e.g., fatty acids, waxes, oils). In another embodiment the composition is an immediate release composition, i.e., a composition in which all or substantially all of the compound is released immediately after administration.

In yet another embodiment, the compounds of the present invention can be delivered in a controlled release system. For example, the agent may be administered using intravenous infusion, an implantable osmotic pump, a transdermal patch, or other modes of administration. In an embodiment, a pump may be used. In one embodiment, polymeric materials can be used. In yet another embodiment, a controlled release system can be placed in proximity to the therapeutic target, i.e., the brain, thus requiring only a fraction of the systemic dose (see, e.g., *Design of Controlled Release Drug Delivery Systems*, Xiaoling Li and Bhaskara R. Jasti eds. (McGraw-Hill, 2006)).

The compounds included in the pharmaceutical compositions of the present invention may also include incorporation of the active ingredients into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

In accordance with the present invention, the compounds of the present invention may be modified by, for example, the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection, than do the corresponding unmodified compounds. Such modifications may also increase the compounds' solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently, or in lower doses than with the unmodified compound.

EXAMPLES

Unless otherwise stated, all reactions were carried out under an atmosphere of dry argon or nitrogen in dried glassware. Indicated reaction temperatures refer to those of the reaction bath, while room temperature (RT) is noted as about 25° C. All solvents were of anhydrous quality and all chemicals were purchased from Sigma-Aldrich (St. Louis, Mo.) and were used as received.

General methods. Thin layer chromatography (TLC) was run on pre-coated Merck silica gel 60F254 plates and observed under UV light (Merck KGaA, Darmstadt, Germany). The products were isolated and purified by crystallization or using a Teledyne ISCO Rf Flash chromatography system with hexanes and ethyl acetate as eluents (Teledyne ISCO Inc., Lincoln, Nebr.). The $^1$H (400 MHz), $^{13}$C (101 MHz), gCOSY, and gHSQC NMR spectra were taken on a Varian 400-MR spectrophotometer using TMS as an internal standard (Agilent, Inc., Santa Clara, Calif.). Chemical shifts (δ) are expressed in ppm, coupling constants (J) are expressed in Hz, and splitting patterns are described as follows: s=singlet; d=doublet; t=triplet; q=quartet; m=multiplet; dd=doublet of doublets; dt=doublet of triplets; td=triplet of doublets; ddd=doublet of doublet of doublets. For the verification of the product and purity analysis, the LC-MS was taken on an Agilent 1200 series system with an Agilent 6210 Time-Of-Flight (TOF) mass detector using Agilent Eclipse XDB-C-18 column (5 mm, 4.6×150 mm) using a flow rate of 0.9 ml/min and solvent system water (with 0.1% formic acid)/acetonitrile (ACN) (Gradient: 50% ACN @ 0 minutes, 80% ACN @ 7 minutes, 80% ACN @ 10 minutes and 50% ACN @ 15 minutes).

Example 1

This example provides a general procedure for synthesis of the compounds, salts, solvates, or stereoisomers of any one the compounds of Formula I, as set forth above.

The general reaction scheme is provided below.

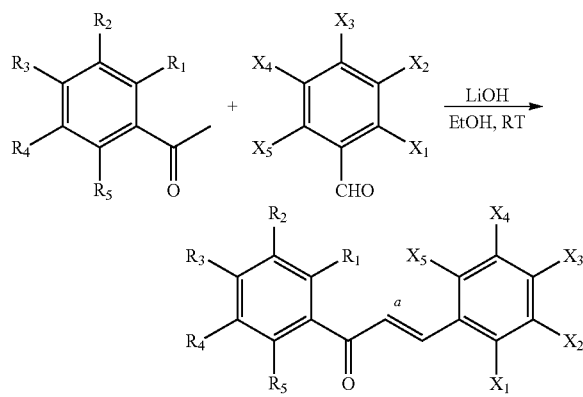

In a 14-ml vial, the substituted acetophenone (1.25 mmol) and lithium hydroxide monohydrate (0.251 mmol) were dissolved in ethanol (5 ml) and the mixture was stirred at RT for 10 minutes followed by addition of substituted benzaldehyde (1.272 mmol). The reaction mixture was then stirred at RT and monitored by TLC using 25% ethyl acetate/hexanes as the solvent system. The reaction was quenched after 2 hours by pouring into 50 ml of stirring ice cold water. If the product precipitated out after quenching with cold water, it was filtered off and crystallized with hot ethanol. In some examples, a sticky mass was observed in the aqueous solution after quenching. In those cases, the product was extracted by ethyl acetate (3×50 ml), dried over sodium sulfate, and concentrated under vacuum. The crude product was purified by flash chromatography using ethyl acetate/hexanes as the solvent system in increasing order of polarity.

Example 2

This example provides the synthesis of (E)-1-(2,3,4-trimethoxyphenyl)-3-(2,4-dinitrophenyl)prop-2-en-1-one (Compound 14).

Compound 14 was obtained as yellow solid in 24% yield. $^1$H NMR (400 MHz, DMSO) δ=8.79 (s, 1H), 8.55 (d, J=8.2, 1H), 8.22 (d, J=8.6 Hz, 1H), 7.82 (d, J=15.7 Hz, 1H), 7.56 (d, J=15.8 Hz, 1H), 7.46 (d, J=8.7 Hz, 1H), 6.96 (d, J=8.9 Hz, 1H), 3.99-3.66 (m, 10H). $^{13}$C NMR (101 MHz, DMSO) δ=189.40, 157.95, 153.84, 148.70, 147.96, 142.07, 136.54, 135.40, 133.77, 131.27, 128.36, 126.13, 125.60, 120.71, 108.52, 62.27, 61.01, 56.65.

Example 3

This example provides the synthesis of (E)-1-(3-methoxyphenyl)-3-(2,4-dinitrophenyl)prop-2-en-1-one (Compound 15).

Compound 15 was obtained as dark green solid in 24% yield. $^1$H NMR (400 MHz, DMSO) δ=8.79 (s, 1H), 8.57 (d, J=7.8 Hz, 1H), 8.44 (d, J=8.6 Hz, 1H), 8.07-7.92 (m, 2H), 7.77 (d, J=7.3 Hz, 1H), 7.62 (s, 1H), 7.51 (t, J=7.9 Hz, 1H), 7.27 (d, J=7.7 Hz, 1H), 3.84 (s, 3H). $^1$H NMR (400 MHz, CDCl$_3$) δ=8.93 (d, J=2.0 Hz, 1H), 8.53 (dd, J=8.6, 2.0 Hz, 1H), 8.14 (d, J=15.7 Hz, 1H), 7.95 (d, J=8.5 Hz, 1H), 7.63-7.52 (m, 2H), 7.43 (dd, J=18.3, 11.8 Hz, 2H), 7.19 (dd, J=8.1 Hz, 2.2 Hz, 1H), 3.90 (s, 3H). $^{13}$C NMR (101 MHz, DMSO) δ=189.10, 160.06, 148.90, 148.12, 138.61, 137.45, 136.24, 131.74, 130.56, 129.65, 128.10, 121.84, 120.64, 120.29, 113.74, 55.89.

Example 4

This example provides the synthesis of (E)-1-(3-methoxyphenyl)-4-(4-(trifluoromethyl)phenyl)prop-2-en-1-one (Compound 16).

Compound 16 was obtained as yellow solid in 15% yield. $^1$H NMR (400 MHz, DMSO) δ=8.60 (dd, J=8.7, 2.4 Hz, 1H), 8.47 (d, J=8.7 Hz, 1H), 8.24-8.17 (m, 2H), 8.09 (d, J=15.5 Hz, 1H), 7.96 (d, J=15.5 Hz, 1H), 7.16-7.09 (m, 2H), 3.89 (s, 3H). $^{13}$C NMR (101 MHz, DMSO) δ=187.28, 164.19, 148.92, 148.02, 136.34, 136.33, 131.81, 131.61, 130.15, 129.78, 128.04, 120.63, 114.67, 56.14.

Example 5

This example provides the synthesis of (E)-1-(3-methoxyphenyl)-4-(4-(trifluoromethyl)phenyl)prop-2-en-1-one (Compound 17).

Compound 17 was obtained as white solid in 61% yield. $^1$H NMR (400 MHz, DMSO) δ 8.14 (d, J=8.1 Hz, 2H), 8.07

(d, J=15.7 Hz, 1H), 7.85-7.80 (m, 3H), 7.79 (d, J=4.3 Hz, 1H), 7.67-7.62 (m, 1H), 7.52 (t, J=7.9 Hz, 1H), 7.27 (dd, J=8.2, 2.6 Hz, 1H), 3.87 (s, 3H). $^{13}$C NMR (101 MHz, DMSO) δ 189.29, 160.04, 142.49, 139.13, 13.50 (d, J=31.2 Hz), 130.45, 129.95, 126.12 (q, J=3.7 Hz), 124.5 (d, J=272.46 Hz), 125.20, 121.65, 119.90, 113.58, 55.86. LC-MS (ESI-TOF): m/z 304.0943 ([$C_{17}H_{13}F_3O_2$+H]$^+$ calculated. 307.0940). Purity 100.00% (rt 9.52 minutes).

Example 6

This example provides the synthesis of (E)-1-(2,3,4-trimethoxyphenyl)-3-(2-(trifluoromethyl)phenyl)prop-2-en-1-one (Compound 24).

Compound 24 was obtained as yellow solid in 58% yield. $^1$H NMR (400 MHz, DMSO) δ=8.10 (d, J=7.7 Hz, 1H), 7.80 (dt, J=22.4, 7.7 Hz, 3H), 7.66 (t, J=7.6 Hz, 1H), 7.56 (d, J=15.5 Hz, 1H), 7.46 (d, J=8.8 Hz, 1H), 6.97 (d, J=8.9 Hz, 1H), 3.89 (s, 3H), 3.86 (s, 3H), 3.80 (s, 3H). $^{13}$C NMR (101 MHz, DMSO) δ=189.74, 157.66, 153.66, 142.08, 136.44 (d, J=2.1 Hz), 133.60, 133.46 (d, J=2.0 Hz), 131.02, 130.73, 128.71, 127.78 (d, J=29.2 Hz), 126.66 (d, J=5.0 Hz), 125.95 (d, J=7.0 Hz), 124.59 (d, J=274.5 Hz), 108.48, 62.21, 60.98, 56.60. LC-MS (ESI-TOF): m/z 367.1152 ([$C_{19}H_{17}F_3O_4$+H]$^+$ calculated. 367.1152). Purity 96.17% (rt 8.70 minutes).

Example 7

This example provides the synthesis of (E)-1-(2,4-dimethoxyphenyl)-3-(2,4-dinitrophenyl)prop-2-en-1-one (Compound 27).

Compound 27 was obtained as dark yellow solid in 12% yield. $^1$H NMR (400 MHz, DMSO) δ=8.80 (d, J=2.4 Hz, 1H), 8.56 (dd, J=8.7, 2.4 Hz, 1H), 8.22 (d, J=8.7 Hz, 1H), 7.81 (d, J=15.7 Hz, 1H), 7.68 (dd, J=12.1, 9.4 Hz, 2H), 6.75-6.64 (m, 2H), 3.93 (s, 3H), 3.87 (s, 3H). $^{13}$C NMR (101 MHz, DMSO) δ=188.67, 165.18, 161.25, 148.73, 147.84, 136.67, 134.38, 134.28, 132.91, 131.28, 128.29, 120.86, 120.68, 106.84, 99.03, 56.56, 56.18.

Example 8

This example provides the synthesis of (E)-1-(3-methoxyphenyl)-3-(3-(trifluoromethyl)phenyl)prop-2-en-1-one (Compound 28).

Compound 28 was obtained as white solid in 21% yield. $^1$H NMR (400 MHz, DMSO) δ 8.35 (s, 1H), 8.21 (d, J=7.8 Hz, 1H), 8.11 (d, J=15.7 Hz, 1H), 7.87-7.77 (m, 3H), 7.70 (t, J=7.78 Hz, 1H), 7.66 (dd, J=1.6, 2.5 Hz, 1H), 7.52 (t, J=7.94 Hz, 1H), 7.27 (ddd, J=0.8, 2.6, 8.2 Hz, 1H), 3.87 (s, 3H). $^{13}$C NMR (101 MHz, DMSO) δ 189.28, 160.03, 142.68, 139.18, 136.27, 133.32, 130.41, 130.36, 130.25 (q, J=31.2 Hz), 127.15 (q, J=3.7 Hz), 125.72 (q, J=3.7 Hz), 124.50 (q, J=272.5 Hz), 124.46, 121.70, 119.76, 113.68, 55.85. LC-MS (ESI-TOF): m/z 304.0945 ([$C_{17}H_{13}F_3O_2$H]$^+$ calculated. 307.0940). Purity 100.00% (rt 9.35 minutes).

Example 9

This example provides the synthesis of (E)-1-(2,3,4-trimethoxyphenyl)-3-(3-(trifluoromethyl)phenyl)prop-2-en-1-one (Compound 29).

Compound 29 was obtained as yellow oil in 46% yield. $^1$H NMR (400 MHz, DMSO) δ 8.13 (s, 1H), 8.09 (d, J=7.8 Hz, 1H), 7.78 (d, J=7.7 Hz, 1H), 7.71-7.56 (m, 3H), 7.42 (d, J=8.7 Hz, 1H), 6.96 (d, J=8.9 Hz, 1H), 3.89 (s, 3H), 3.85 (s, 3H), 3.80 (s, 3H). $^{13}$C NMR (101 MHz, DMSO) δ 190.46, 157.30, 153.41, 142.11, 140.87, 136.36, 132.23, 130.49, 130.27 (q, J=31.2 Hz), 128.92, 126.96 (q, J=3.7 Hz), 126.42, 125.69, 125.66 (q, J=5.0 Hz), 124.43 (q, J=272.5 Hz), 108.33, 62.14, 60.97, 56.57. LC-MS (ESI-TOF): m/z 367.1157 ([$C_{19}H_{17}F_3O_4$+H]$^+$ calculated. 367.1152). Purity 97.99% (rt 8.83 minutes).

Example 10

This example provides the synthesis of (E)-1-(3,4-dimethoxyphenyl)-3-(2,4-dinitrophenyl)prop-2-en-1-one (Compound 33).

Compound 33 was obtained as dark yellow powder in 18% yield. $^1$H NMR (400 MHz, DMSO) δ=8.82 (d, J=2.3 Hz, 1H), 8.60 (dd, J=8.7, 2.3, 1H), 8.46 (d, J=8.7 Hz, 1H), 8.08 (d, J=15.5 Hz, 1H), 8.00-7.91 (m, 2H), 7.62 (d, J=2.0 Hz, 1H), 7.14 (d, J=8.5 Hz, 1H), 3.89 (s, 3H), 3.87 (s, 3H). $^{13}$C NMR (101 MHz, DMSO) δ=187.30, 154.25, 149.37, 148.00, 136.41, 136.33, 131.66, 130.18, 129.71, 128.03, 124.53, 120.63, 111.43, 111.28, 56.34, 56.09.

Example 11

This example provides the synthesis of (E)-1-(2,5-dimethoxyphenyl)-3-(2-nitrophenyl)prop-2-en-1-one (Compound 37).

Compound 37 was obtained as yellow solid in 49% yield. $^1$H NMR (400 MHz, d$_2$o) δ=8.09 (dd, J=8.1, 1.1 Hz, 1H), 7.97 (d, J=7.7 Hz, 1H), 7.85-7.76 (m, 2H), 7.73-7.65 (m, 1H), 7.41 (d, J=15.8 Hz, 1H), 7.16 (d, J=1.8 Hz, 2H), 7.09 (t, J=1.8 Hz, 1H), 3.84 (s, 3H), 3.76 (s, 3H). $^{13}$C NMR (101 MHz, d$_2$o) δ=191.59, 153.41, 152.61, 137.66, 134.31, 131.31, 131.11, 130.19, 129.56, 128.86, 125.14, 119.67, 114.33, 114.32, 56.74, 55.96. LC-MS (ESI-TOF): m/z 314.1029 ([$C_{17}H_{15}NO_5$+H]$^+$ calculated. 314.1023). Purity 100.00% (rt 6.63 minutes).

Example 12

This example provides the synthesis of (E)-1-(2,6-dimethoxyphenyl)-3-(2-nitrophenyl)prop-2-en-1-one (Compound 43).

Compound 43 was obtained as white solid in 82% yield. $^1$H NMR (400 MHz, DMSO) δ=8.06 (dd, J=8.1, 1.2 Hz, 1H), 7.98 (dd, J=7.8, 1.3 Hz, 1H), 7.78 (ddd, J=7.8, 1.2, 0.6 Hz, 1H), 7.70-7.64 (m, 1H), 7.52 (d, J=16.0 Hz, 1H), 7.40 (t, J=8.4 Hz, 1H), 6.96 (d, J=16.0 Hz, 1H), 6.77 (d, J=8.4 Hz, 2H), 3.75 (s, 7H). $^{13}$C NMR (101 MHz, DMSO) δ=194.37, 157.44, 148.75, 140.06, 134.33, 132.66, 131.72, 131.52, 129.86, 129.66, 125.21, 117.59, 104.80, 56.26. LC-MS (ESI-TOF): m/z 314.1024 ([$C_{17}H_{15}NO_5$+H]$^+$ calculated. 314.1023). Purity 100.00% (rt 5.74 minutes).

Example 13

This example provides the synthesis of (E)-1-(2,6-dimethoxyphenyl)-3-(3-nitrophenyl)prop-2-en-1-one (Compound 44).

Compound 44 was obtained as fluffy white solid in 86% yield. $^1$H NMR (400 MHz, DMSO) δ 8.53 (t, J=1.9 Hz, 1H), 8.27-8.16 (m, 2H), 7.69 (t, J=8.0 Hz, 1H), 7.47-7.33 (m, 2H), 7.20 (d, J=16.2 Hz, 1H), 6.77 (d, J=8.4 Hz, 2H), 3.73 (s, 6H). $^{13}$C NMR (101 MHz, DMSO) δ 194.32, 157.40, 148.79, 142.11, 136.64, 134.63, 131.53, 131.30, 130.81, 125.14, 123.83, 118.15, 104.92, 56.28.

Example 14

This example provides the synthesis of (E)-1-(2,6-dimethoxyphenyl)-3-(2-(trifluoromethyl)phenyl)prop-2-en-1-one (Compound 46).

Compound 46 was obtained as white solid in 67% yield. $^1$H NMR (400 MHz, DMSO) δ 8.07 (s, 1H), 8.01 (d, J=7.9 Hz, 1H), 7.74 (d, J=7.8 Hz, 1H), 7.61 (t, J=7.8 Hz, 1H), 7.38 (t, J=8.4 Hz, 1H), 7.30 (d, J=16.3 Hz, 1H), 7.14 (d, J=16.2 Hz, 1H), 6.74 (d, J=8.5 Hz, 2H), 3.70 (s, 6H). $^{13}$C NMR (101 MHz, DMSO) δ 194.45, 157.36, 142.84, 135.92, 132.43, 131.45, 130.69, 130.41, 130.26 (q, J=31.1 Hz), 127.17 (q, J=3.6 Hz), 125.92 (q, J=3.8 Hz), 124.38 (q, J=272.5 Hz), 118.22, 104.90, 56.27. LC-MS (ESI-TOF): m/z 337.1045 ([$C_{18}H_{15}F_3O_3$+H]$^+$ calculated. 337.1046). Purity 100.00% (rt 7.68 minutes).

Example 15

This example provides the synthesis of (E)-1-(2,6-dimethoxyphenyl)-3-(3-(trifluoromethyl)phenyl)prop-2-en-1-one (Compound 47).

Compound 47 was obtained as light yellow solid in 72% yield. $^1$H NMR (400 MHz, DMSO) δ=8.07 (d, J=7.8 Hz, 1H), 7.76 (d, J=7.8, 1H), 7.71 (dd, J=11.4 Hz, 4.0 Hz, 1H), 7.61 (t, J=7.6 Hz, 1H), 7.45 (d, J=2.1 Hz, 1H), 7.40 (dd, J=11.1 Hz, 5.7 Hz, 1H), 7.02 (d, J=15.9 Hz, 1H), 6.75 (d, J=8.4 Hz, 2H), 3.70 (s, 6H). $^{13}$C NMR (101 MHz, DMSO) δ=194.52, 157.33, 139.62 (d, J=2.2 Hz), 133.52, 132.81 (d, J=1.6 Hz), 132.57, 131.77, 131.02, 128.90, 127.59 (q, J=30.2 Hz), 126.64 (q, J=5.7 Hz), 124.38 (q, J=274.5 Hz), 117.44, 104.69, 56.22. LC-MS (ESI-TOF): m/z 337.1050 ([$C_{18}H_{15}F_3O_3$+H]$^+$ calculated. 337.1046). Purity 98.65% (rt 7.83 minutes).

Example 16

This example provides the synthesis of (E)-1-(2-methoxyphenyl)-3-(2,4-dinitrophenyl)prop-2-en-1-one (Compound 52).

Compound 52 was obtained as off white solid in 46% yield. $^1$H NMR (400 MHz, DMSO) δ=8.80 (d, J=2.4 Hz, 1H), 8.56 (dd, J=8.6, 2.4 Hz, 1H), 8.24 (d, 1=8.6 Hz, 1H), 7.82 (d, J=15.9 Hz, 1H), 7.64-7.52 (m, 3H), 7.24 (d, J=8.2 Hz, 1H), 7.10 (td, J=7.5 Hz, 0.7 Hz, 1H), 3.91 (s, 3H). $^{13}$C NMR (101 MHz, DMSO) δ=191.62, 158.70, 148.74, 148.00, 136.44, 135.63, 134.49, 133.92, 131.37, 130.38, 128.30, 128.19, 121.14, 120.69, 112.91, 56.40.

Example 17

This example provides the synthesis of (E)-1-(2-methoxyphenyl)-3-(2-(trifluoromethyl)phenyl)prop-2-en-1-one (Compound 53).

Compound 53 was obtained as yellow oil in 72% yield. $^1$H NMR (400 MHz, CDCl$_3$) δ=7.90-7.82 (m, 1H), 7.71 (d, J=7.8 Hz, 1H), 7.63 (d, J=7.8 Hz, 1H), 7.55 (dd, J=7.6 Hz, 1.8, 1H), 7.50 (t, J=7.6 Hz, 1H), 7.45-7.36 (m, 2H), 7.22 (d, J=15.7 Hz, 1H), 6.97 (td, J=7.5 Hz, 0.8 Hz, 1H), 6.92 (d, J=8.4 Hz, 1H), 3.82 (s, 4H). $^{13}$C NMR (101 MHz, DMSO) δ=192.21, 158.40, 136.83 (d, J=2.1 Hz), 134.05, 133.58, 133.29 (d, J=1.6 Hz), 131.30, 130.82, 130.15, 128.79, 128.58, 127.81 (q, J=29.2 Hz), 126.68 (q, J=5.2 Hz), 124.55 (q, J=274.5 Hz), 121.07, 112.76, 56.31. LC-MS (ESI-TOF): m/z 304.0940 ([$C_{17}H_{13}F_3O_2$+H]$^+$ calculated. 307.0940). Purity 96.40% (rt 8.69 minutes).

Example 18

This example provides the synthesis of (E)-1-(2-methoxyphenyl)-3-(3-(trifluoromethyl)phenyl)prop-2-en-1-one (Compound 54).

Compound 54 was obtained as yellow oil in 45% yield. $^1$H NMR (400 MHz, DMSO) δ 8.57 (t, J=1.9 Hz, 1H), 8.29-8.19 (m, 2H), 7.73 (t, J=8.0 Hz, 1H), 7.69-7.61 (m, 2H), 7.61-7.57 (m, 1H), 7.57-7.52 (m, 1H), 7.22 (d, J=7.9 Hz, 1H), 7.08 (td, J=7.5, 0.9 Hz, 1H), 3.89 (s, 3H). LC-MS (ESI-TOF): m/z 304.0941 ([$C_{17}H_{13}F_3O_2$+H]$^+$ calculated. 307.0940). Purity 96.00% (rt 8.88 minutes).

Example 19

This example provides the synthesis of (E)-1-(3,5-dimethoxyphenyl)-3-(2-nitrophenyl)prop-2-en-1-one (Compound 55).

Compound 55 was obtained as off white solid in 57% yield. $^1$H NMR (400 MHz, DMSO) δ=8.21 (dd, J=7.8, 1.3 Hz, 1H), 8.10 (dd, J=8.1, 1.2 Hz, 1H), 7.98 (d, J=15.5 Hz, 1H), 7.89-7.80 (m, 2H), 7.74-7.68 (m, 1H), 7.28 (d, J=2.3 Hz, 2H), 6.82 (t, J=2.3 Hz, 1H), 3.85 (s, 6H). $^{13}$C NMR (101 MHz, DMSO) δ=189.21, 161.19, 149.24, 139.53, 139.25, 134.18, 131.52, 130.15, 130.09, 126.89, 125.13, 106.91, 105.89, 56.05. LC-MS (ESI-TOF): m/z 314.1024 ([$C_{17}H_{15}NO_5$+H]$^+$ calculated. 314.1023). Purity 100.00% (rt 7.21 minutes).

Example 20

This example provides the synthesis of (E)-1-(3,5-dimethoxyphenyl)-3-(3-nitrophenyl)prop-2-en-1-one (Compound 56).

Compound 56 was obtained as light yellow powder in 63% yield. $^1$H NMR (400 MHz, DMSO) δ 8.78 (t, J=1.8 Hz, 1H), 8.38 (d, J=7.8 Hz, 1H), 8.32-8.24 (m, 1H), 8.12 (d, J=15.7 Hz, 1H), 7.86 (d, J=15.7 Hz, 1H), 7.75 (t, J=8.0 Hz, 1H), 7.33 (d, J=2.3 Hz, 2H), 6.82 (t, J=2.3 Hz, 1H), 3.85 (s, 6H). $^{13}$C NMR (101 MHz, DMSO) δ 189.04, 161.20, 148.85, 142.13, 139.68, 136.98, 135.54, 130.75, 125.18, 123.75, 107.00, 105.63, 56.05.

Example 21

This example provides the synthesis of (E)-1-(3,5-dimethoxyphenyl)-3-(4-nitrophenye prop-2-en-1-one (Compound 57).

Compound 57 was obtained as light yellow powder in 75% yield. $^1$H NMR (400 MHz, DMSO) δ 8.28 (d, J=8.9 Hz, 2H), 8.20 (d, J=8.9 Hz, 2H), 8.10 (d, J=15.7 Hz, 1H), 7.82 (d, J=15.7 Hz, 1H), 7.31 (d, J=2.3 Hz, 2H), 6.83 (t, J=2.3 Hz, 1H), 3.85 (s, 6H). $^{13}$C NMR (101 MHz, DMSO) δ 188.99, 161.22, 148.54, 141.78, 141.56, 139.60, 130.45, 126.44, 124.32, 106.95, 105.82, 56.06.

Example 22

This example provides the synthesis of (E)-1-(3,5-dimethoxyphenyl)-3-(2,4-dinitrophenyl)prop-2-en-1-one (Compound 58).

Compound 58 was obtained as dark yellow solid in 23% yield. $^1$H NMR (400 MHz, DMSO) δ=8.81 (d, J=2.3 Hz, 1H), 8.59 (dd, J=8.6, 2.4 Hz, 1H), 8.46 (d, J=8.7 Hz, 1H), 8.00 (s, 2H), 7.30 (d, J=2.3 Hz, 2H), 6.84 (t, J=2.3 Hz, 1H), 3.85 (s, 6H). $^1$H NMR (400 MHz, CDCl$_3$) δ=8.93 (d, J=2.0 Hz, 1H), 8.52 (dd, J=8.5, 2.0 Hz, 1H), 8.12 (d, J=15.7 Hz, 1H), 7.94 (d, J=8.6 Hz, 1H), 7.35 (d, J=15.7 Hz, 1H), 7.14 (d, J=2.1 Hz, 2H), 6.72 (s, 1H), 3.88 (s, 6H). $^{13}$C NMR (101 MHz, DMSO) δ=188.96, 161.24, 148.92, 148.12, 139.21, 137.58, 136.23, 131.81, 129.63, 128.06, 120.63, 107.08, 106.07, 56.08.

Example 23

This example provides the synthesis of (E)-1-(3,5-dimethoxyphenyl)-3-(2-(trifluoromethyl)phenyl)prop-2-en-1-one (Compound 59).

Compound 59 was obtained as yellow oil in 72% yield. $^1$H NMR (400 MHz, DMSO) δ=8.36 (d, J=7.9 Hz, 1H), 7.98 (s, 2H), 7.85 (d, J=7.8 Hz, 1H), 7.80 (t, J=7.6 Hz, 1H), 7.68 (t, J=7.6 Hz, 1H), 7.30 (d, J=2.2, Hz 2H), 6.83 (t, J=2.2 Hz, 1H), 3.85 (s, 6H). $^1$H NMR (400 MHz, CDCl$_3$) δ=8.12 (d, J=13.9 Hz, 1H), 7.82 (d, J=7.8 Hz, 1H), 7.73 (d, J=7.8 Hz, 1H), 7.61 (t, J=7.6 Hz, 1H), 7.51 (t, J=7.7 Hz, 1H), 7.35 (d, J=15.6 Hz, 1H), 7.14 (d, J=2.2 Hz, 2H), 6.69 (t, J=2.1 Hz, 1H), 3.86 (s, 7H). $^{13}$C NMR (101 MHz, DMSO) δ=188.97, 161.20, 139.53, 138.45 (d, J=2.2 Hz), 133.39, 133.18 (d, J=1.6 Hz), 131.00, 129.40, 127.96 (q, J=29.2 Hz), 126.67, 129.60 (q, J=5.2 Hz), 124.62 (q, J=273.5 Hz), 106.93, 105.88, 56.05. LC-MS (ESI-TOF): m/z 337.1047 ([C$_{18}$H$_{15}$F$_3$O$_3$+H]$^+$ calculated. 337.1046). Purity 100.00% (rt 9.37 minutes).

Example 24

This example provides the synthesis of (E)-1-(3,5-dimethoxyphenyl)-3-(3-(trifluoromethyl)phenyl)prop-2-en-1-one (Compound 60).

Compound 60 was obtained as light yellow solid in 72% yield. $^1$H NMR (400 MHz, DMSO) δ 8.34 (s, 1H), 8.22 (d, J=7.8 Hz, 1H), 8.08 (d, J=15.7 Hz, 1H), 7.88-7.77 (m, 2H), 7.70 (t, J=7.8 Hz, 1H), 7.32 (d, J=2.3 Hz, 2H), 6.83 (t, J=2.2 Hz, 1H), 3.85 (s, 6H). $^{13}$C NMR (101 MHz, DMSO) δ 189.08, 161.18, 142.83, 139.77, 136.24, 133.33, 130.33, 130.24 (q, J=32.2 Hz), 127.17 (q, J=3.6 Hz), 125.85 (q, J=3.7 Hz), 124.50 (q, J=273.5 Hz), 124.36, 106.98, 105.52, 56.03. LC-MS (ESI-TOF): m/z 337.1049 ([C$_{18}$H$_{15}$F$_3$O$_3$+H]$^+$ calculated. 337.1046). Purity 100.00% (rt 9.55 minutes).

Example 25

This example provides the synthesis of (E)-1-(2,5-dimethoxyphenyl)-3-(2,4-dinitrophenyl)prop-2-en-1-one (Compound 61).

Compound 61 was obtained as rusty yellow solid in 31% yield. $^1$H NMR (400 MHz, DMSO) δ=8.80 (d, J=2.3 Hz, 1H), 8.57 (dd, J=8.7, 2.3 Hz, 1H), 8.23 (d, J=8.7 Hz, 1H), 7.83 (d, J=15.8 Hz, 1H), 7.55 (dd, J=15.8, 0.9 Hz, 1H), 7.23-7.09 (m, 3H), 3.86 (d, J=0.9 Hz, 3H), 3.77 (d, J=0.9 Hz, 3H). $^{13}$C NMR (101 MHz, DMSO) δ=191.20, 153.50, 152.94, 148.72, 148.00, 136.46, 135.89, 133.74, 131.38, 128.49, 128.34, 120.71, 120.24, 114.44, 114.41, 56.85, 56.04.

Example 26

This example provides the synthesis of (E)-1-(2,6-dimethoxyphenyl)-3-(2,4-nitrophenyl)prop-2-en-1-one (Compound 62).

Compound 62 was obtained as light yellow solid in 33% yield. $^1$H NMR (400 MHz, DMSO) δ=8.76 (d, J=2.3 Hz, 1H), 8.51 (dd, J=8.6, 2.2 Hz, 1H), 8.23 (d, J=8.7 Hz, 1H), 7.58 (d, J=16.1 Hz, 1H), 7.42 (t, J=8.4 Hz, 1H), 7.09 (d, J=16.0 Hz, 1H), 6.78 (d, J=8.5 Hz, 2H), 3.75 (s, 6H). $^{13}$C NMR (101 MHz, DMSO) δ=194.09, 157.53, 148.47, 148.07, 138.60, 136.20, 134.91, 132.01, 131.48, 128.21, 120.66, 117.28, 104.81, 56.29.

Example 27

This example provides the synthesis of (E)-1-(2,4,6-trimethoxyphenyl)-3-(2-(trifluoromethyl)phenyl)prop-2-en-1-one (Compound 88).

Compound 88 was obtained as yellow solid in 72% yield. $^1$H NMR (400 MHz, DMSO) δ=8.04 (d, J=7.8 Hz, 1H), 7.77 (d, J=7.7 Hz, 1H), 7.71 (t, 1=7.5 Hz, 1H), 7.60 (t, J=7.6 Hz, 1H), 7.48 (dd, J=15.9, 2.2 Hz, 1H), 7.01 (d, J=15.8 Hz, 1H), 6.30 (s, 2H), 3.82 (s, 3H), 3.70 (s, 6H). $^{13}$C NMR (101 MHz, DMSO) δ=193.37, 162.78, 162.78, 158.71, 138.33 (d, J=2.2 Hz), 133.51, 133.07, 130.80, 128.83, 127.58 (q, J=29.2 Hz), 126.61 (q, J=6.0 Hz), 124.46 (q, J=274.5 Hz), 110.73, 91.34, 56.23, 55.96. LC-MS (ESI-TOF): m/z 367.1157 ([C$_{19}$H$_{17}$F$_3$O$_4$+H]$^+$ calculated. 367.1152). Purity 96.17% (rt 7.58 minutes).

Example 28

This example provides the synthesis of (E)-1-(2,4,6-trimethoxyphenyl)-3-(2,4-dinitrophenyl)prop-2-en-1-one (Compound 93).

Compound 93 was obtained as fluffy yellow solid in 41% yield. $^1$H NMR (400 MHz, DMSO) δ=8.75 (d, J=2.3 Hz, 1H), 8.49 (dd, J=8.6, 2.3 Hz, 1H), 8.18 (d, J=8.7 Hz, 1H), 7.58 (d, J=16.0 Hz, 1H), 7.06 (d, J=15.9 Hz, 1H), 6.31 (s, 2H), 3.82 (s, 3H), 3.73 (s, 6H). $^{13}$C NMR (101 MHz, DMSO) δ=192.70, 163.04, 159.01, 148.49, 147.97, 137.05, 136.37, 135.55, 131.40, 128.18, 120.65, 110.59, 91.46, 56.32, 55.99.

Example 28

This example provides the synthesis of (E)-1-(2,4,6-trimethoxyphenyl)-3-(4-cyano)prop-2-en-1-one (Compound 94).

Compound 94 was obtained as fluffy, light yellow solid in 64% yield. 1H NMR (400 MHz, DMSO) δ 7.85 (q, J=8.6 Hz, 4H), 7.28 (d, J=16.2 Hz, 1H), 7.11 (d, J=16.2 Hz, 1H), 6.30 (s, 2H), 3.82 (s, 3H), 3.70 (s, 6H); 13C NMR (101 MHz, DMSO) δ 193.18, 162.70, 158.76, 141.23, 139.54, 133.16, 132.27, 129.53, 119.04, 112.61, 111.26, 91.57, 56.30, 55.95.

Example 29

This example provides the synthesis of (E)-1-(2,3,4-trimethoxyphenyl)-3-(3-cyano)prop-2-en-1-one (Compound 99).

Compound 99 was obtained fluffy yellow solid in 77% yield. $^1$H NMR (400 MHz, DMSO) δ 8.26 (s, 1H), 8.08 (d, J=8.0 Hz, 1H), 7.86 (d, J=7.8 Hz, 1H), 7.63 (t, J=7.8 Hz, 1H), 7.58 (d, J=16.0 Hz, 1H), 7.54 (d, J=16.1 Hz, 1H), 7.40 (d, J=8.8 Hz, 1H), 6.93 (d, J=8.8 Hz, 1H), 3.87 (s, 3H), 3.83 (s, 3H), 3.77 (s, 3H); $^{13}$C NMR (101 MHz, DMSO) δ 190.33, 157.38, 153.46, 142.11, 140.24, 136.48, 133.83, 133.17, 132.43, 130.61, 129.14, 126.36, 125.73, 118.87, 112.64, 108.34, 62.19, 60.98, 56.59.

Example 30

This example provides the synthesis of (E)-1-(2,6-dimethoxyphenyl)-3-(4-cyano)prop-2-en-1-one (Compound 102).

Compound 102 was obtained as fluffy white solid in 92% yield. $^1$H NMR (400 MHz, DMSO) δ 7.88 (dd, J=19.8, 8.5 Hz, 4H), 7.40 (t, J=8.4 Hz, 1H), 7.28 (d, J=16.2 Hz, 1H), 7.16 (d, J=16.2 Hz, 1H), 6.76 (d, J=8.4 Hz, 2H), 3.73 (s, 6H); $^{13}$C NMR (101 MHz, DMSO) δ 194.21, 157.41, 142.26, 139.32, 133.17, 131.78, 131.64, 129.65, 119.00, 118.09, 112.80, 104.93, 56.30.

Example 31

This example provides the synthesis of (E)-1-(2-methoxyphenyl)-3-(3-cyano)prop-2-en-1-one (Compound 110).

Compound 110 was obtained as yellowish white solid in 50% yield. $^1$H NMR (400 MHz, DMSO) δ 8.28 (s, 1H), 8.09 (d, J=8.0 Hz, 1H), 7.88 (d, J=7.8 Hz, 1H), 7.64 (t, J=7.8 Hz, 1H), 7.61-7.49 (m, 4H), 7.21 (d, J=8.3 Hz, 1H), 7.08 (t, J=7.5 Hz, 1H), 3.88 (s, 3H), 3.51-2.03 (m, 8H); $^{13}$C NMR (101 MHz, DMSO) δ 192.38, 158.35, 140.29, 136.42, 133.89, 133.81, 133.27, 132.50, 130.58, 130.06, 129.48, 128.99, 121.01, 118.86, 112.83, 112.63, 56.34.

Example 32

This example provides the synthesis of (E)-1-(2,6-dimethoxyphenyl)-3-(3-cyano)prop-2-en-1-one (Compound 115).

Compound 115 was obtained as yellowish white solid in 72% yield. $^1$H NMR (400 MHz, DMSO) δ 8.23 (s, 1H), 8.02 (d, J=8.0 Hz, 1H), 7.84 (d, J=7.7 Hz, 1H), 7.58 (t, J=7.8 Hz, 1H), 7.38 (t, J=8.4 Hz, 1H), 7.24 (d, 1=16.3 Hz, 1H), 7.13 (d, J=16.2 Hz, 1H), 6.74 (d, J=8.4 Hz, 2H), 3.71 (s, 6H); $^{13}$C NMR (101 MHz, DMSO) δ 194.29, 157.38, 142.16, 136.04, 134.03, 133.38, 132.60, 131.54, 130.92, 130.52, 118.76, 118.17, 112.63, 104.91, 56.29.

Example 33

This example details the use of immunocytochemistry to visualize AR translocation.

Figure 7:
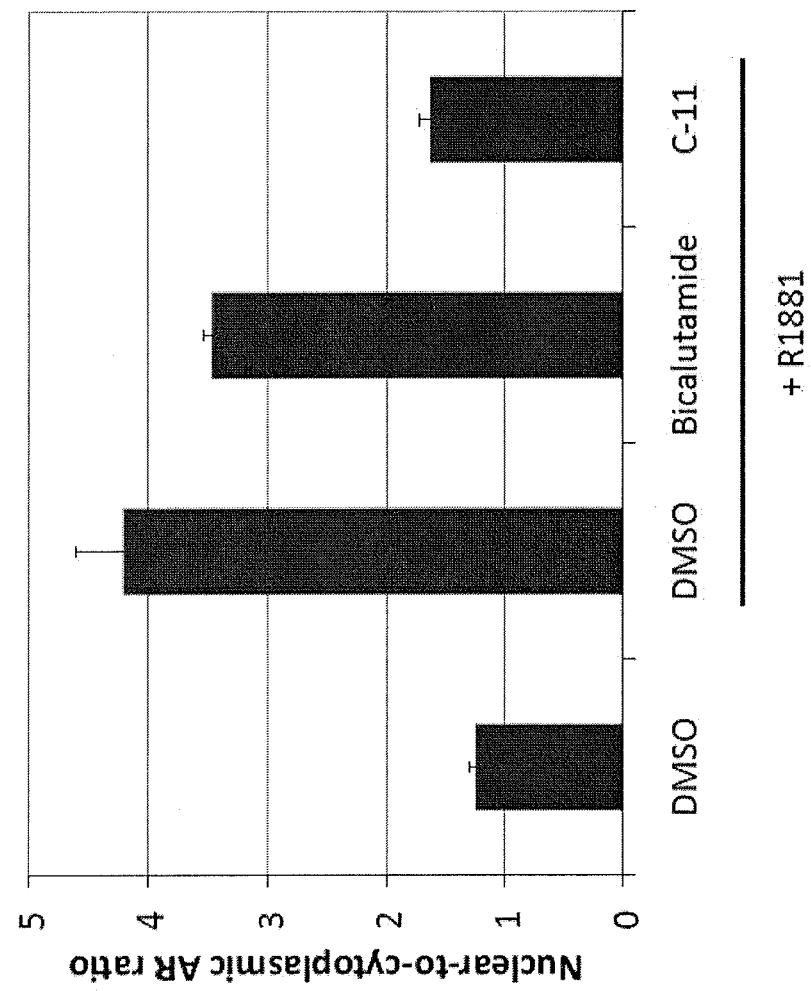
Figure 8:
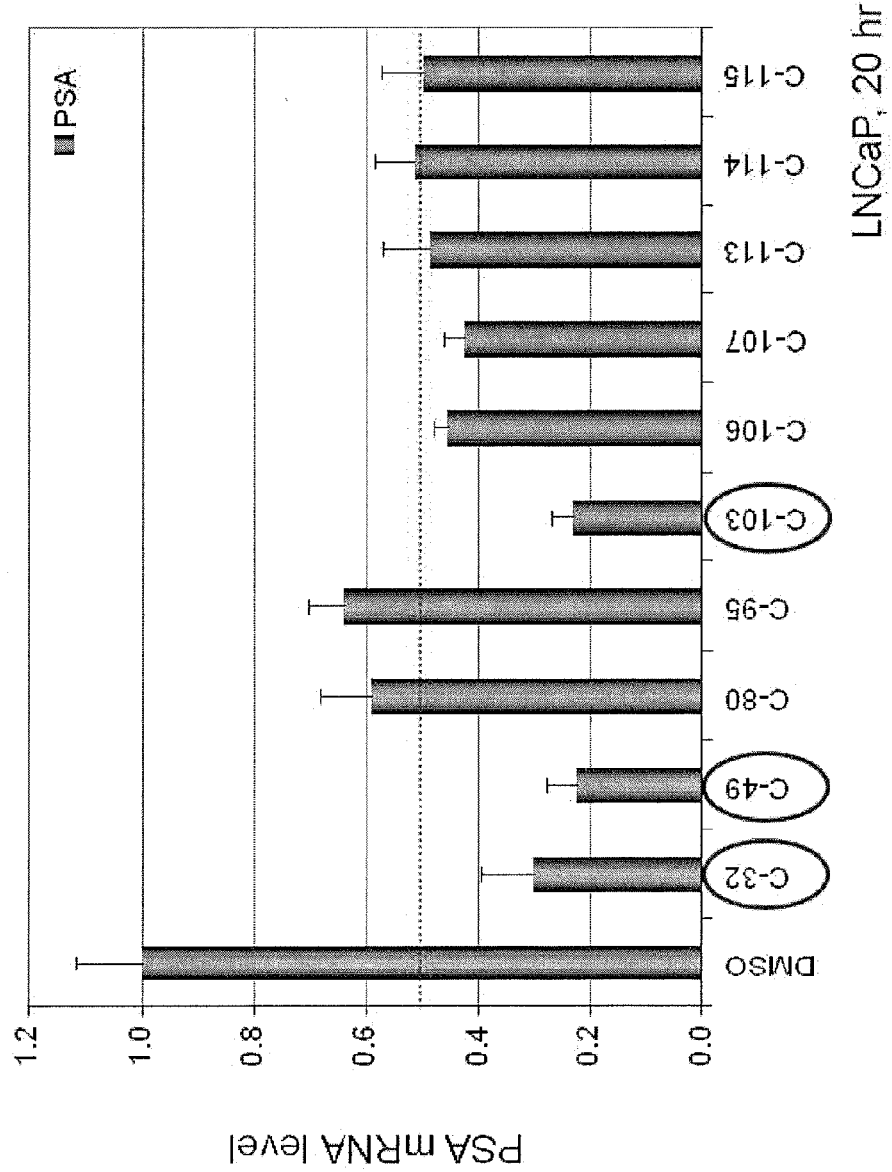
Figure 9:
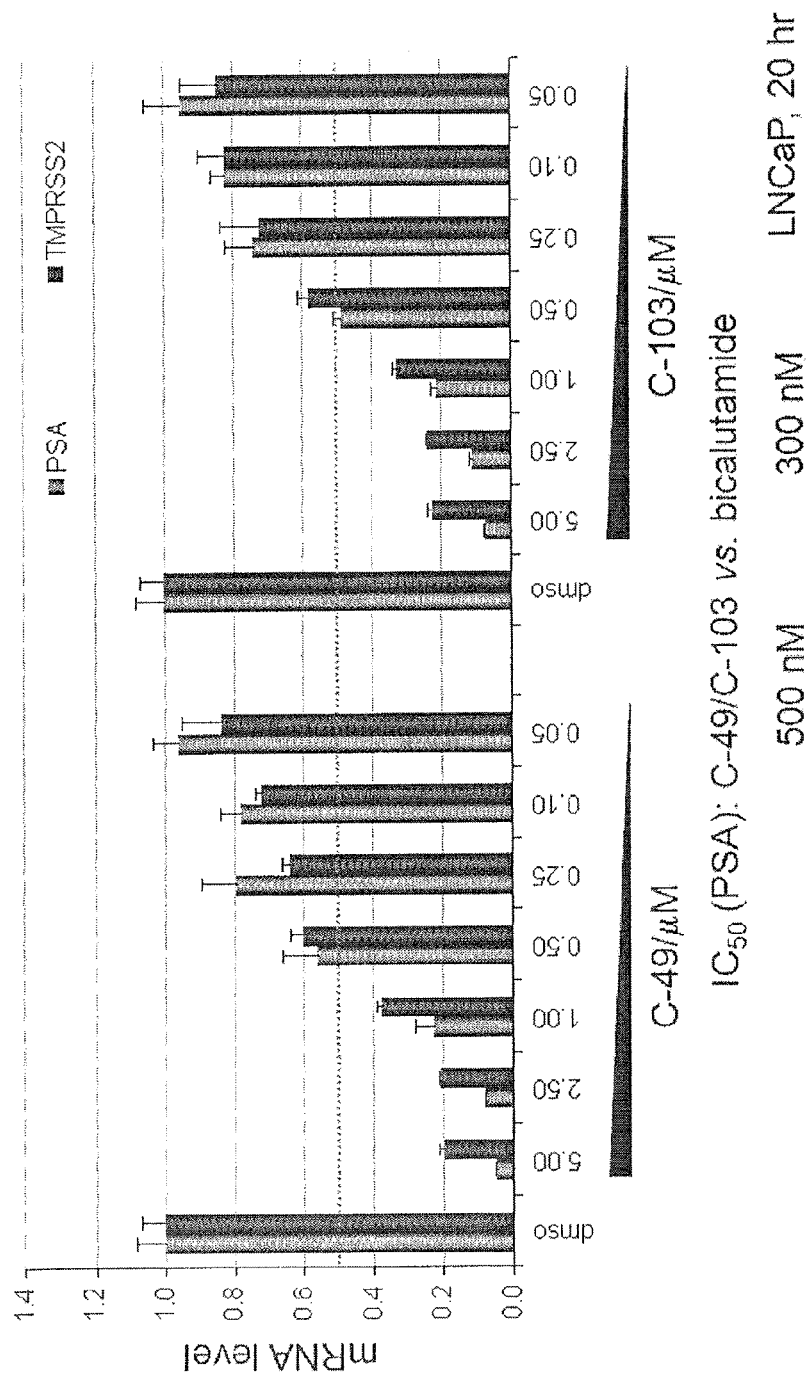
Figure 10:
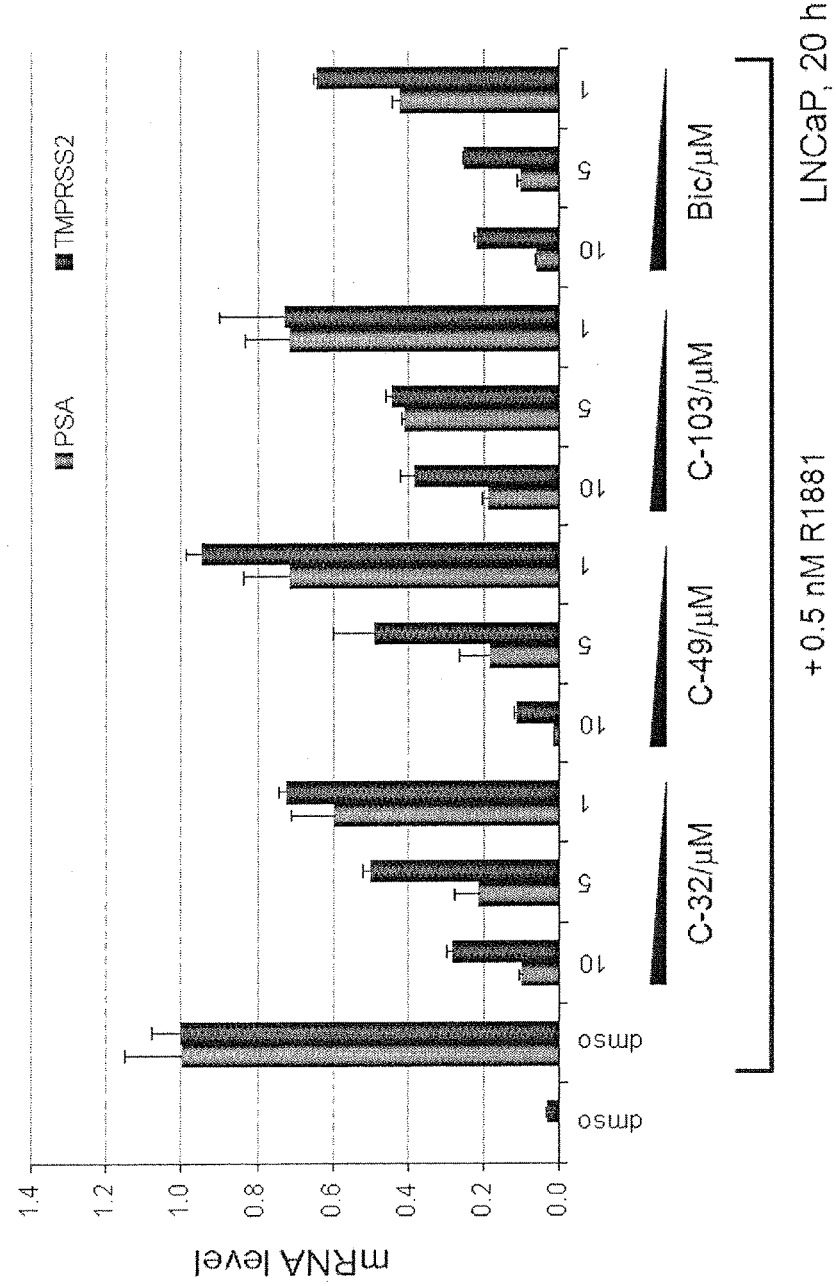
Figure 11:
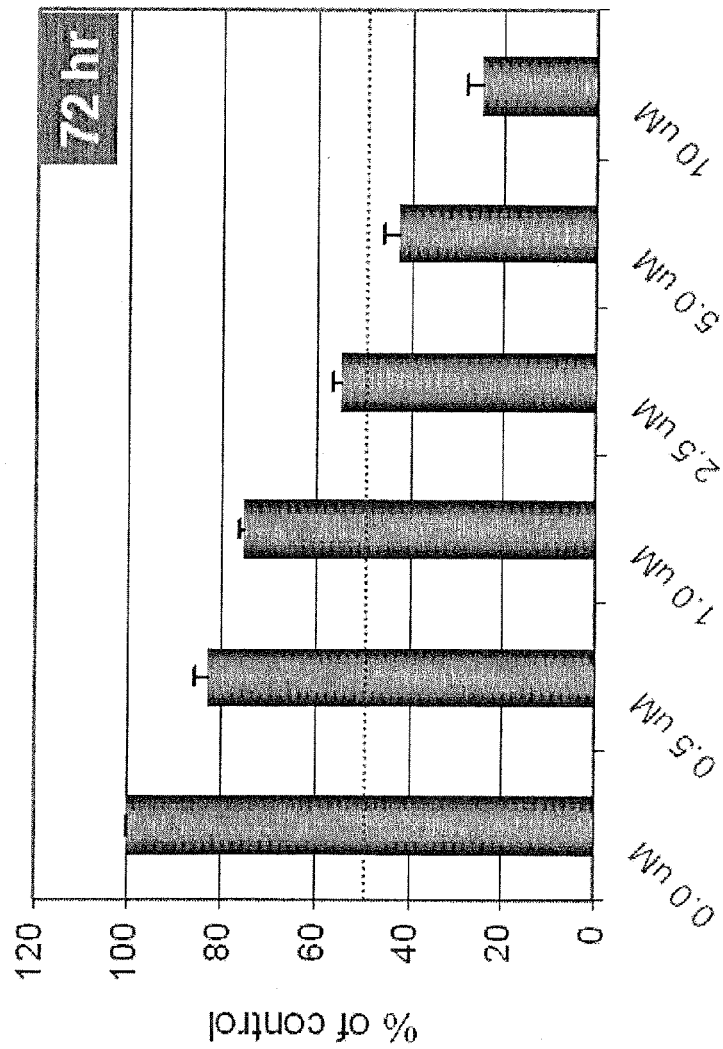
Figure 12:
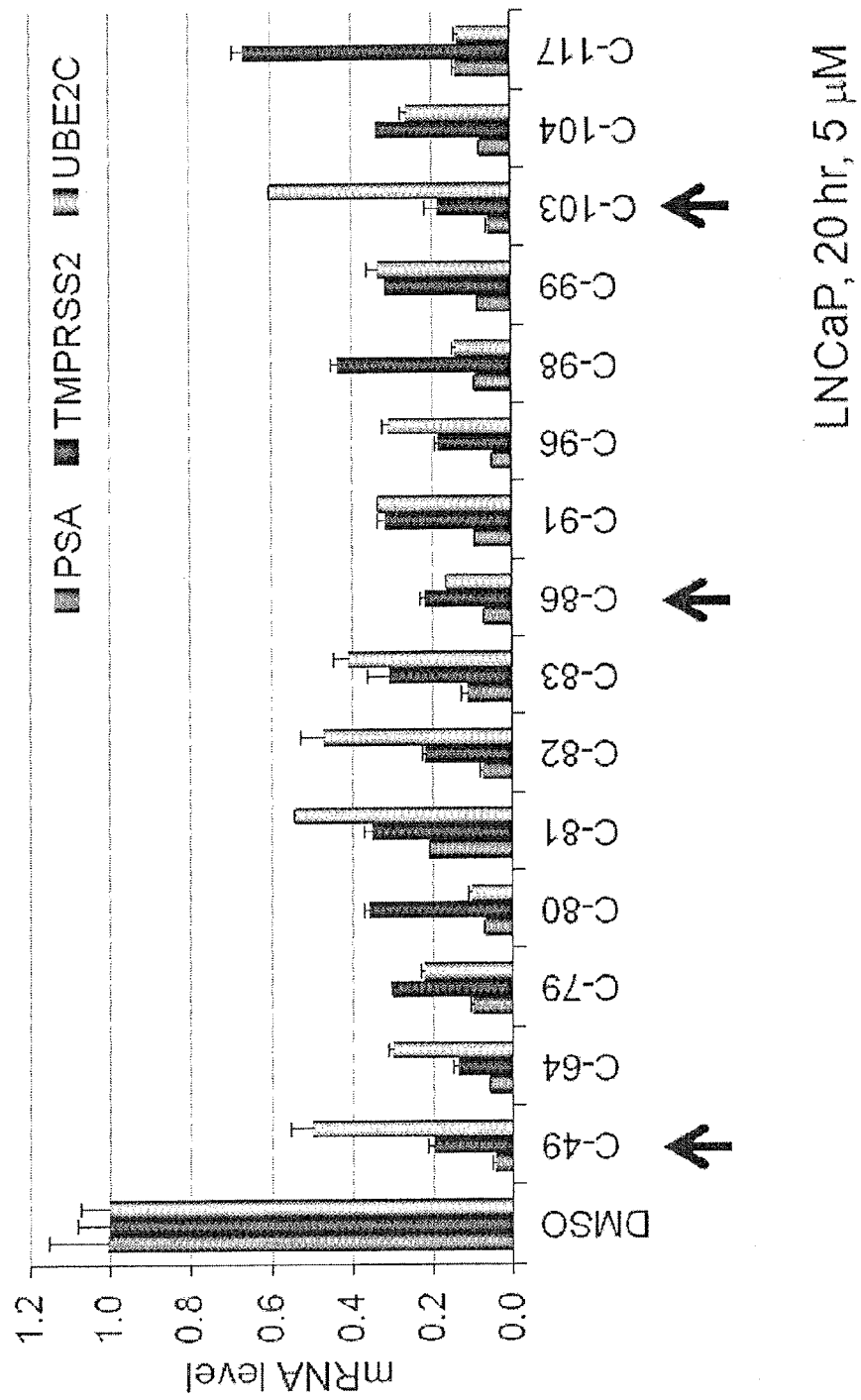
Figure 13:
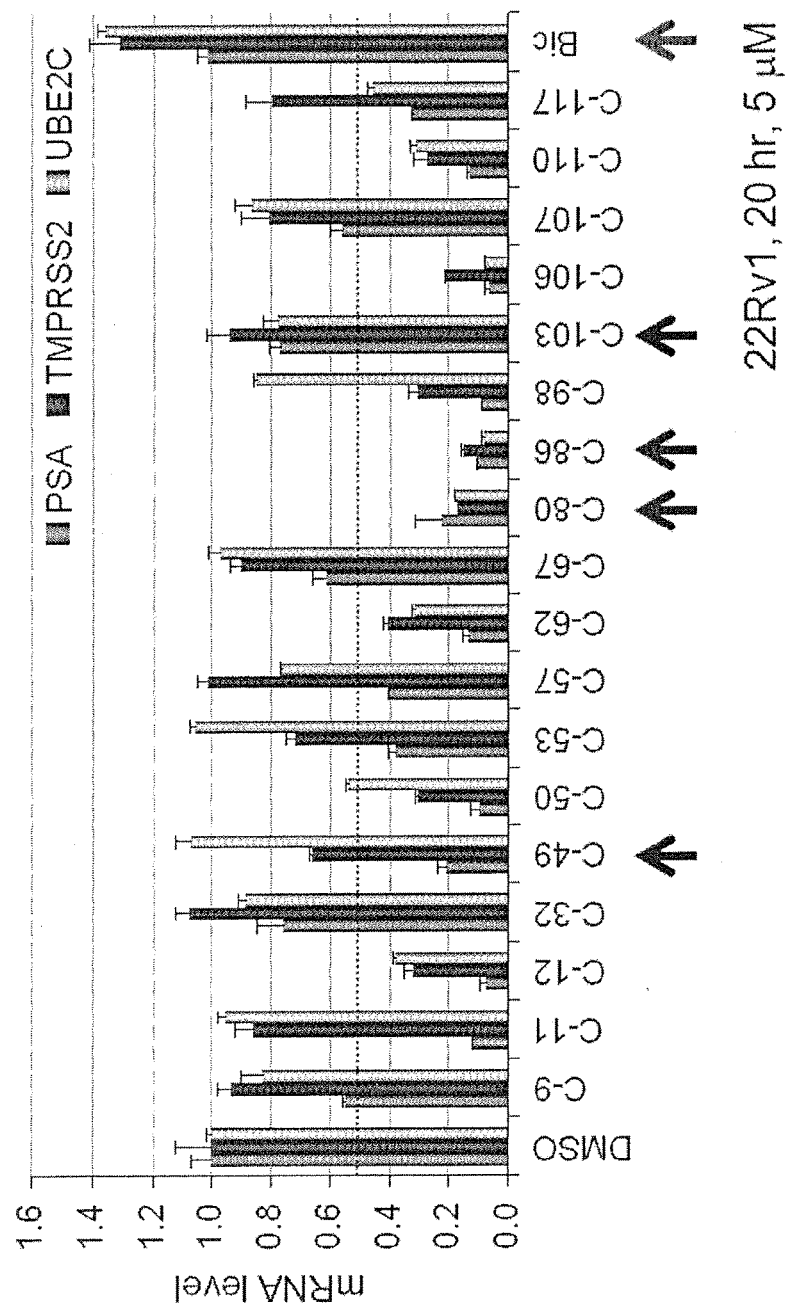
Figure 14:
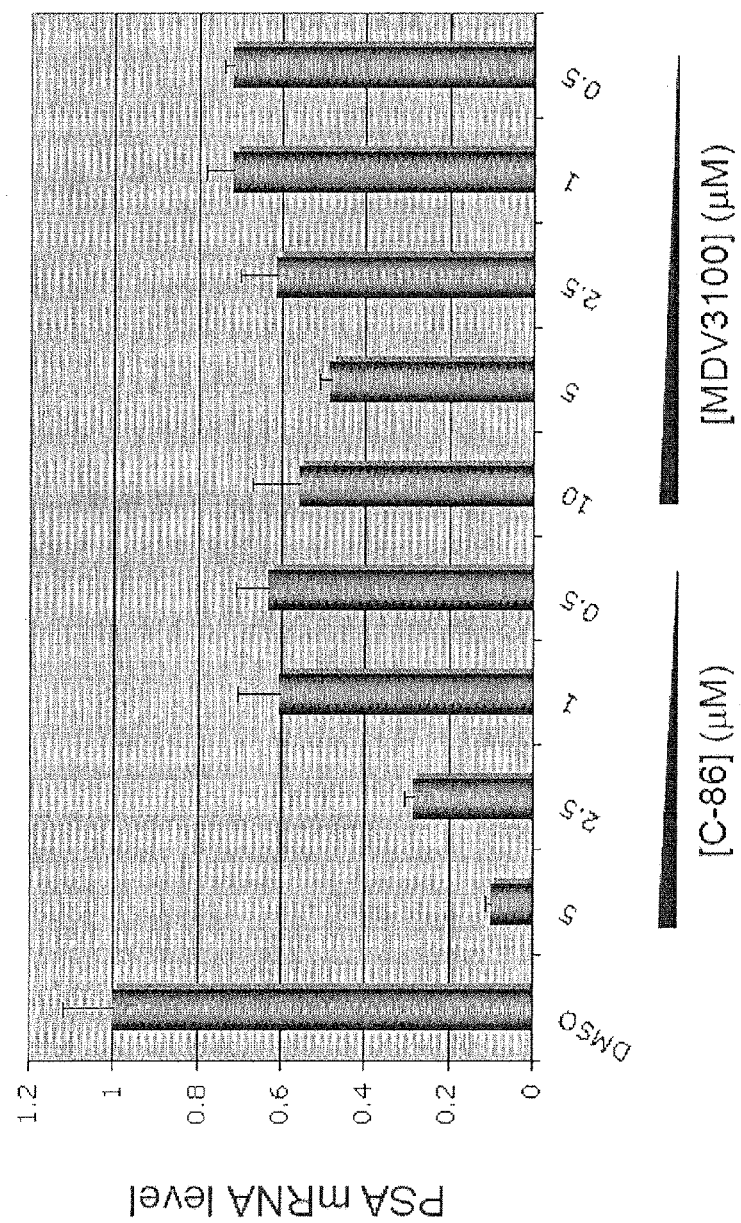

In order to determine the extent to which the compounds of the present invention can inhibit AR translocation from the cytoplasm to the nucleus after addition of the synthetic androgen R1881, LNCaP cells were treated with either DMSO, 1 nM R1881, 10 µM bicalutamide, followed by 1 nM R1881, or 10 µM Compound 11, followed by 1 nM R1881. LNCaP cells were incubated on cover slips in phenol red-free RPMI 1640, with 10% charcoal-stripped FBS, and 1% antimycotic-antibiotic solution, for three days at 37° C. Cells were then treated with DMSO, bicalutamide or Compound 11 for three hours, followed by treatment with R1881 for three hours. After fixation and permeabilization, cells were stained, fluorescence images were obtained using a Leica® fluorescence microscope, and nuclear to cytoplasmic ratios of AR staining intensity were obtained using OpenLab® image analysis software (Perkin Elmer, Waltham, Mass.). Compound 11 was markedly more active than bicalutamide in inhibiting R1881-induced AR translocation to the nucleus (FIG. 7).

Example 34

This example describes the assay used to measure PSA protein expression and the effect of the compounds of the present invention on protein expression.

Figure 1:
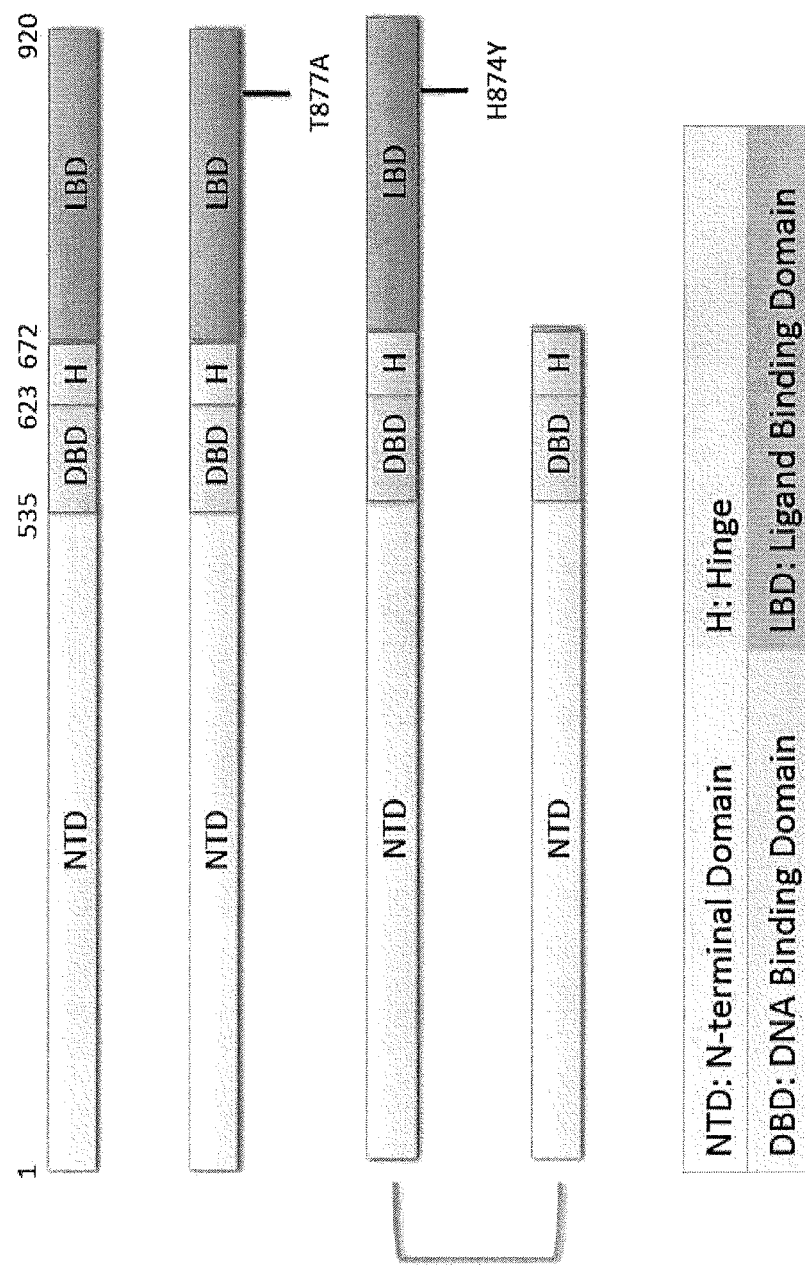
Figure 2:
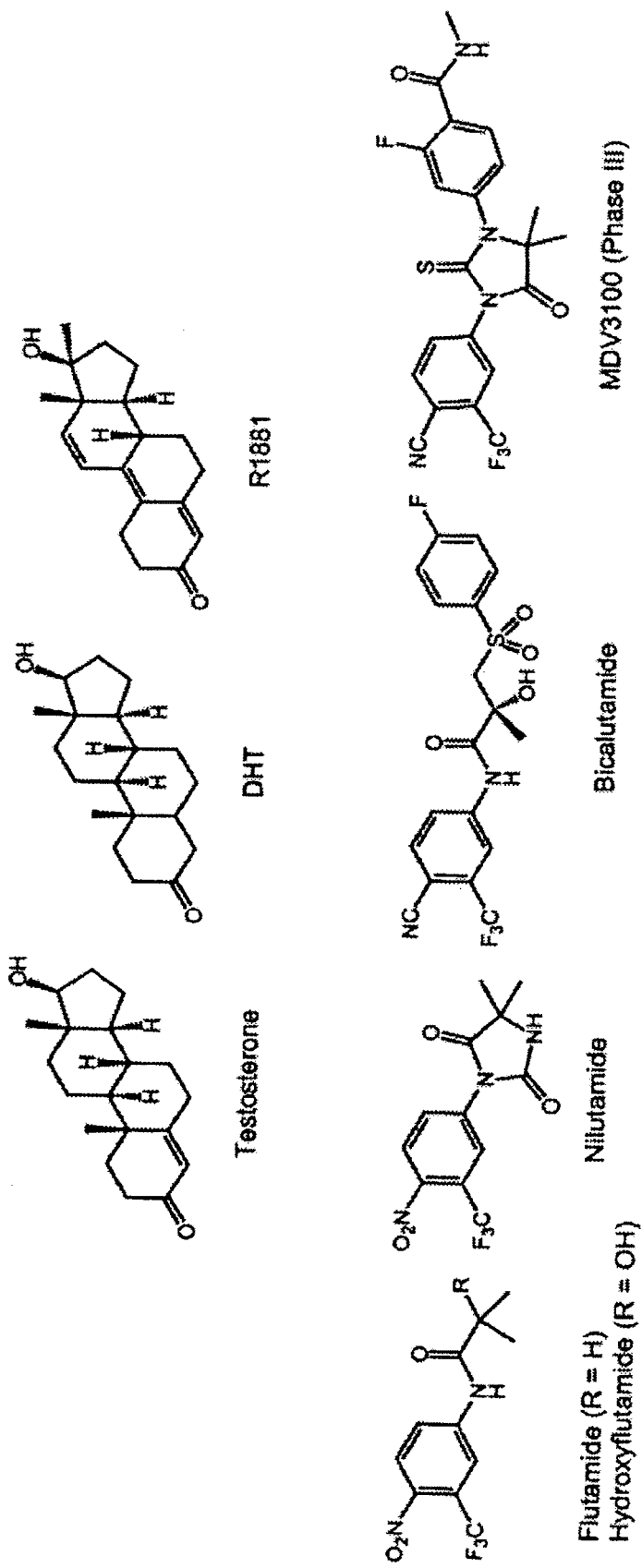
Figure 3:
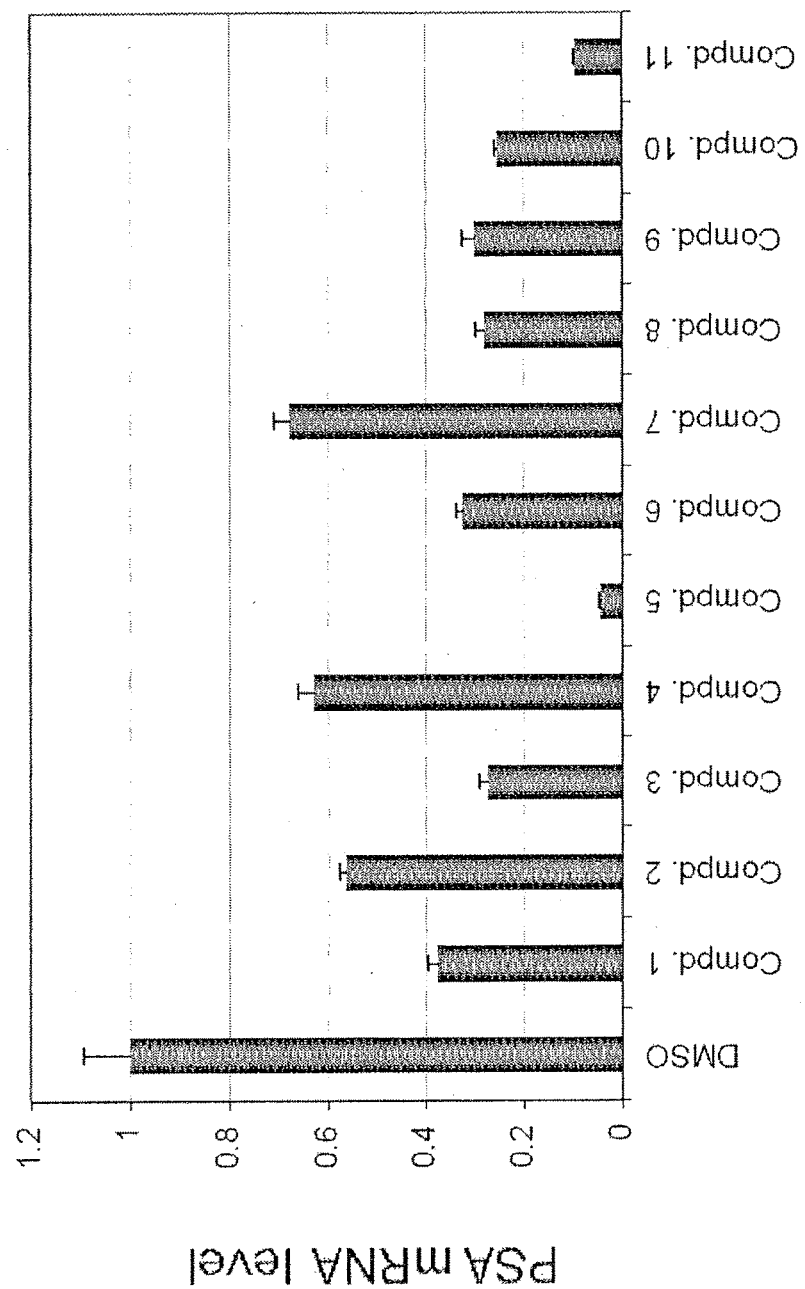
Figure 4:
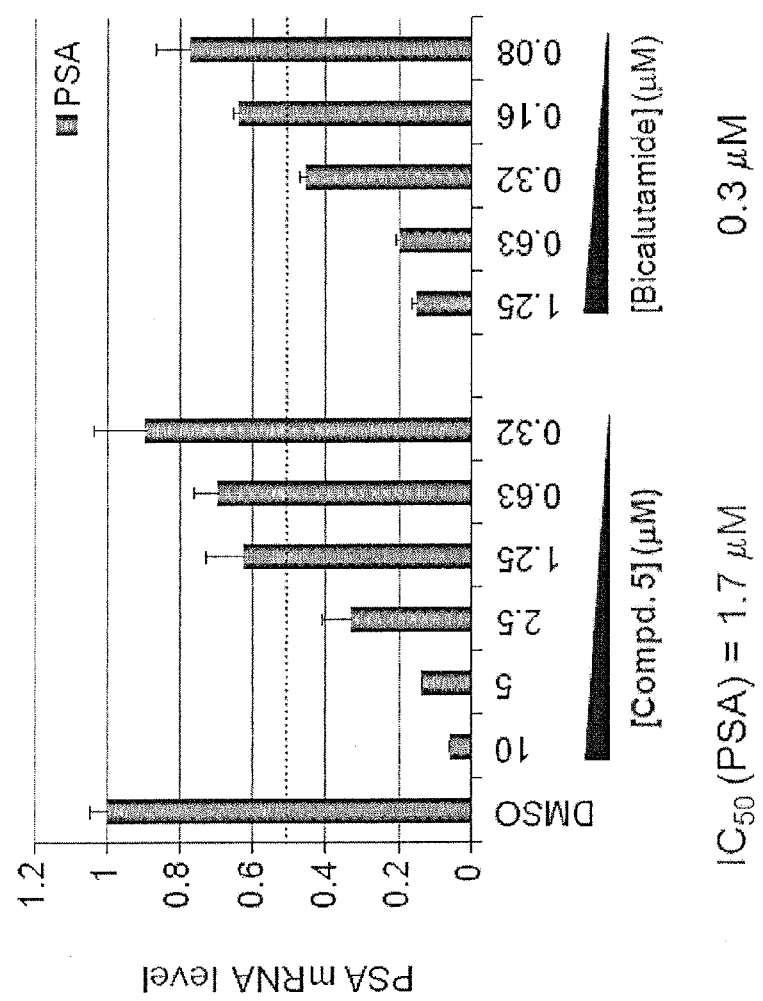
Figure 5:
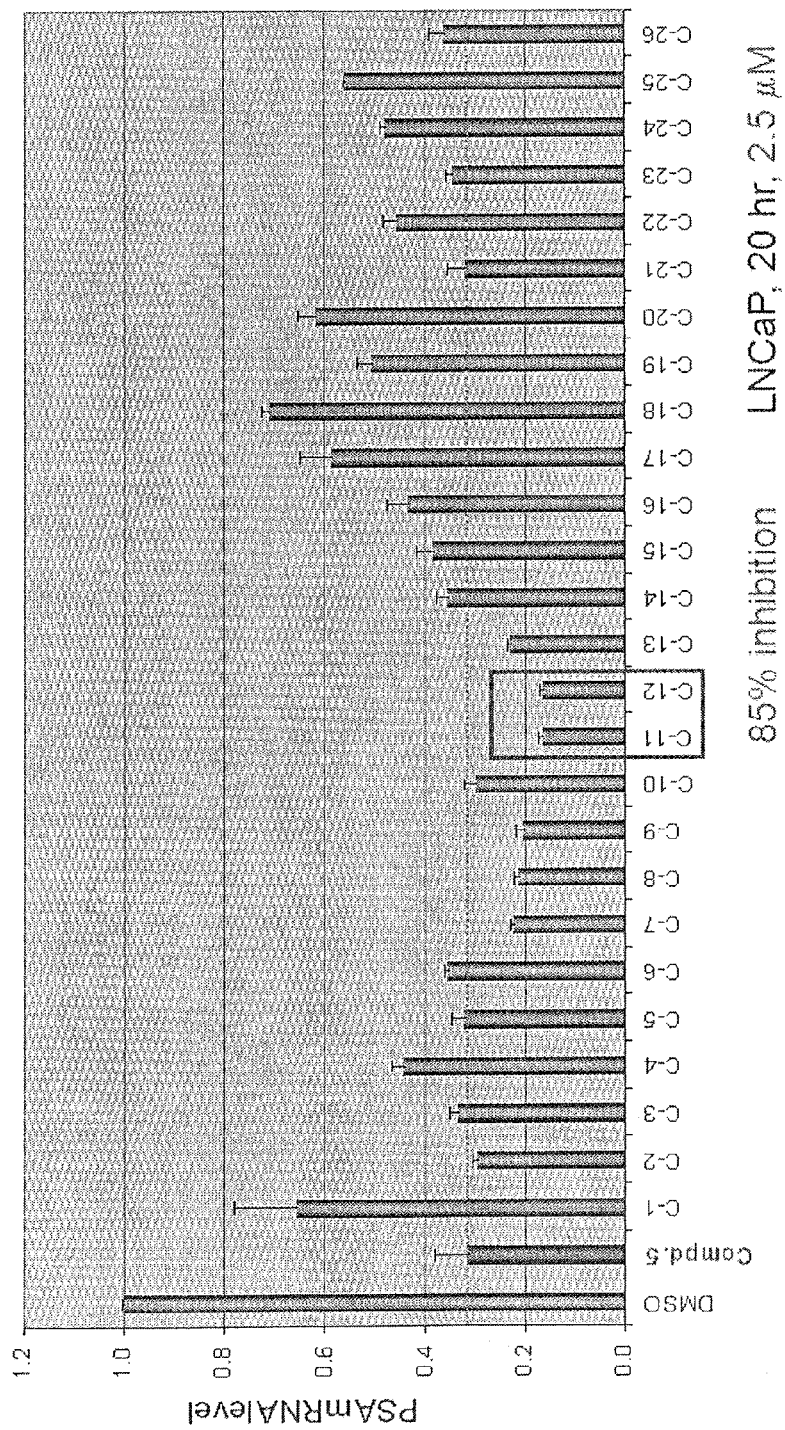
Figure 6:
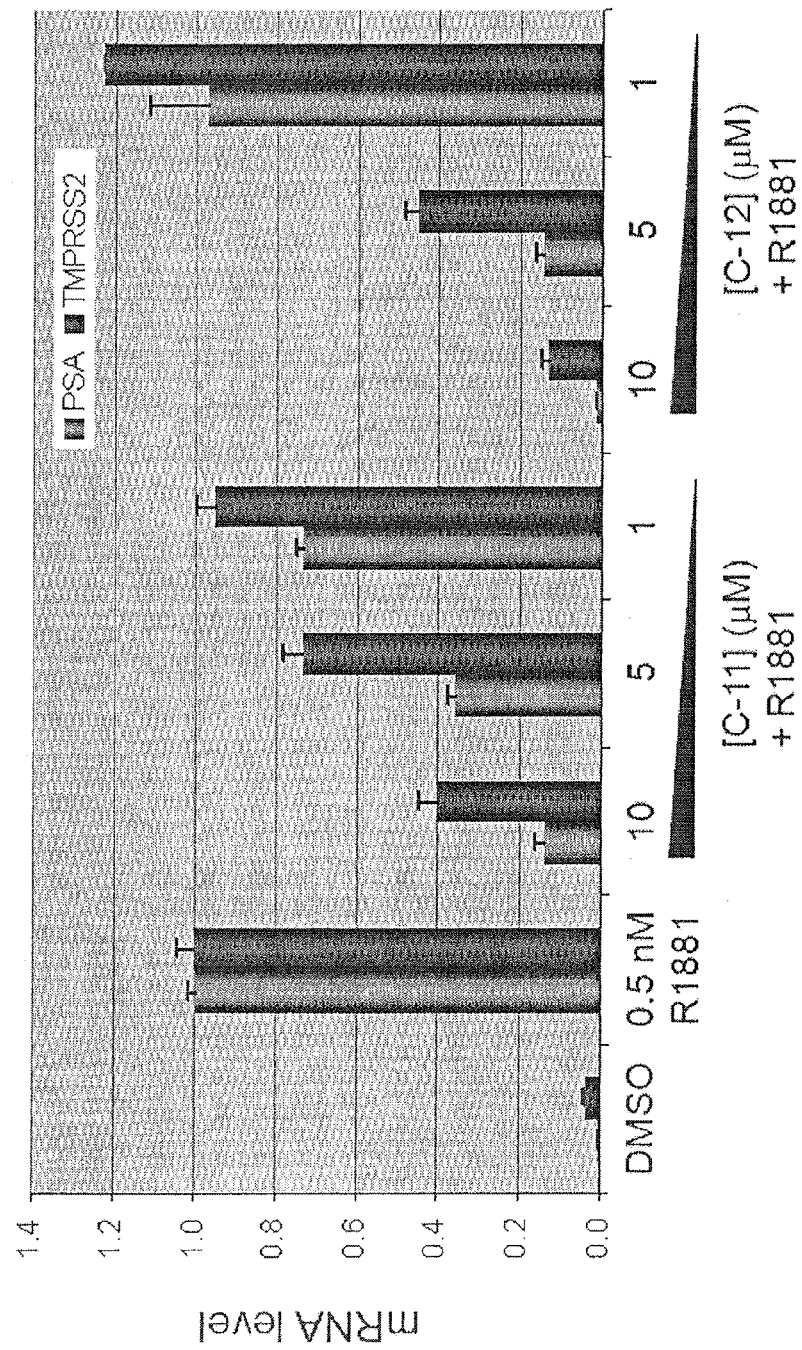

The amount of PSA protein expression levels was measured in cells from the prostate cancer cell line LNCaP, after treatment with either control, or bicalutamide (0.08 µM to 1.25 µM) and from about 0 to 10 µM of one or more of the compounds of the present invention, as shown in FIGS. 3-5. The protein was quantified by an immunohistochemical method using photodetection.

LNCaP cells were maintained in RPMI-1640 medium containing 10% fetal bovine serum. Forty eight hours prior to the experiment, cells were washed several times in serum-free medium and then cultured in RPMI-1640 medium containing 10% charcoal-stripped fetal bovine serum (to remove endogenous androgens). After 48 hours in this medium, the compounds of interest were added in a range of concentrations or at 2.5 µM for 26 other compounds for 24 hours. After an additional 48 hours, cells were lysed as described in Yano A., et al., *Proc. Natl. Acad. Sci. USA*, 105:15541-46 (2008), and PSA protein was monitored by polyacrylamide gel electrophoresis and Western blotting with an anti-PSA antibody (Santa Cruz Biotechnology, Santa Cruz, Calif.).

Example 35

This example discloses the mRNA quantitation methods used.

For PSA, TMPRSS2, and UBE2C mRNA determination, LNCaP cells or 22Rv1 cells, were cultured and treated with the corresponding compounds for 20 hours in the presence or absence of the synthetic androgen R1881. Total RNA was isolated from cultured cells using the RNeasy RNA Isolation Kit (Qiagen). The RNAs were reverse transcribed immediately after RNA extraction with the High Capacity cDNA Reverse Transcription Kit (Applied Biosystems), using random primers included in the kit, according to the manufacturer's instructions. The cDNA products were stored at −20° C. until the PCR analysis was performed. Real-time PCR primers were designed using Primer Express Applications (Applied Biosystems). The primer sequences for real-time PCR were as follows:

```
18S rRNA
                                        (SEQ ID NO: 1)
forward 5'-AGTCCCTGCCCTTTGTACACA-3'
                                        (SEQ ID NO: 2)
reverse 5'-CGATCCGAGGGCCTCACTA-3'

PSA
                                        (SEQ ID NO: 3)
forward 5'-GCAGCATTGAACCAGAGGAGTT-3'
                                        (SEQ ID NO: 4)
reverse 5'-CACGTCATTGGAAATAACATGGA-3'

TMPRSS2
                                        (SEQ ID NO: 5)
forward 5'-AGCCTCTGACTTTCAACGACCTA-3'
                                        (SEQ ID NO: 6)
reverse 5'-TGTTCTGGCTGCAGCATCAT-3'

UBE2C
                                        (SEQ ID NO: 7)
forward 5'-AGGAAAAGTGGTCTGCCCTGTA-3'
                                        (SEQ ID NO: 8)
reverse 5'-ACTATCAATGTTGGGTTCTCCTAGAAG-3'
```

The mRNA level and total protein in cells were measured after treatment with either control, bicalutamide (0.08 µM to 1.25 µM), or MDV3100 (an antiandrogen) and either about 2.5 µM or about 1.0 µM of Compounds 1-117 respectively. It was known that the expression of PSA mRNA in LNCaP cells is driven by an AR mediated pathway. While PSA is androgen-dependent AR-target gene, UBE2C is androgen-independent AR-target gene. The PSA, TMPRSS2 and UBE2C mRNA levels were normalized by the rRNA level.

FIGS. 4 and 5 show the effect of Compound 5 and of 26 additional compounds on expression of PSA protein expression after exposure to the cells for about 20 hours. At 2.5 mRNA expression was decreased significantly after exposure to many of the compounds.

Example 36

This example discloses methods for measurement of AR nuclear translocation using Western blots.

LNCaP cells were maintained as above. At 50% confluence, cells were washed several times in serum-free RPMI-1640 medium, and re-cultured for 72 hours in RPMI-1640 medium containing 10% charcoal-stripped fetal bovine serum. Cells were treated with R1881 (0.5 nM), with, or without 10 µM, 5 µM or 1 µM of Compounds 1-117, and then cells were cultured for 20 hours. Nuclear and cytoplasmic protein fractionation was performed using NE-PER Nuclear and Cytoplasmic Extraction Reagents Kit (Thermo Scientific Pierce Protein Research Products) according to the manufacturer's instructions. Quantification of AR in nucleus and cytosol was performed by Western blotting with an AR-specific antibody following polyacrylamide gel electrophoresis. Appearance of AR in the nuclear fraction following treatment with R1881 represents ligand-dependent nuclear translocation of AR, which is significantly inhibited by the compounds tested.

LNCaP cells were also tested after treatment for only 6 hours. Compounds 49, 80 and 86, as well as KU135 (a C-terminal Hsp90 inhibitor) and 17-AAG (a known AR degradation inducer), were tested at 2.5, 5, and 10 µM as well as control (DMSO vehicle). Compound 80 showed inhibition at 10 µM (data not shown). LAPC-4 cells (a human prostate cancer cell line with wt AR) were tested against Compounds 80, 86, KU-32 (another C-terminal Hsp90 inhibitor) and 17-AAG. Compound 86 showed AR down regulation at 2.5 and 5.0 µM (data not shown).

22Rv1 cells were also tested after treatment for 6 hours. 22Rv1 cells were treated with 1, 2.5, 5, and 10 µM of Compound 86, as well as control (DMSO vehicle), for 6 hours, and then AR protein level was measured using western blot. Compound 86 induced complete degradation of both the full-length mutant AR and the ligand binding domain-deleted AR (data not shown).

Example 37

This example discloses methods for measurement of the degradation of other nuclear receptors, specifically, progesterone receptor (PR) and estrogen receptor (ER), using western blots.

MCF-7 human breast cancer cells were treated with 1, 2.5, 5, and 10 µM Compound 86 as well as control (DMSO vehicle) for 24 hours, and then PR protein level was measured using western blot with anti-PR (Santa Cruz Biotechnology). Compound 86 induced the degradation of PR with dose-dependent manner (data not shown).

MCF-7 human breast cancer cells were treated with 1, 2.5, 5, and 10 µM Compound 86 as well as control (DMSO vehicle) for 24 hours, and then ER protein level was measured using western blot with anti-ER (Santa Cruz Biotechnology). Compound 86 induced the degradation of ER with dose-dependent manner (data not shown).

Example 38

In this example, compounds of the present invention are biotinylated for use in a pull-down assay to determine which proteins bind to the compounds.

The general method for biotinylating the compounds of the present invention is shown below. In this particular example Compound 86 is shown being conjugated with an iodinated biotin reagent in the presence of $Cs_2CO_3$ and dimethylformamide. The reaction scheme is provided below.

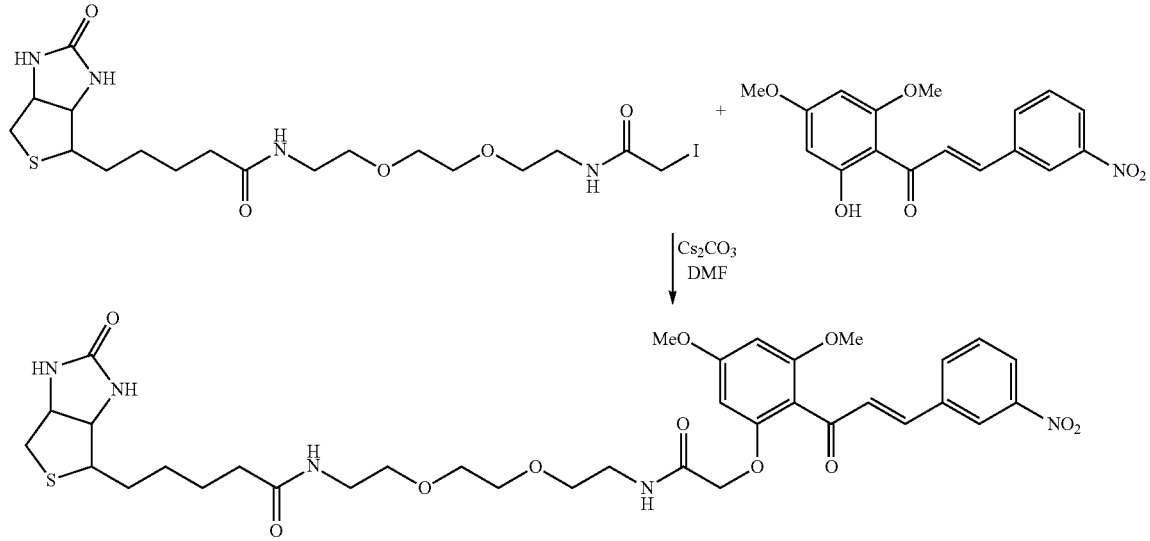

Example 39

This example describes the pull-down assay used in conjunction with the compounds of the present invention, and the use of this assay to determine that Compound 86 modulates heat shock protein 40 (Hsp40).

Figure 15:
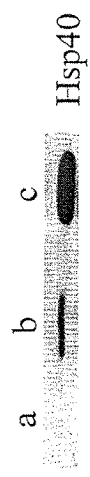

22Rv1 cell lysate was incubated with biotinylated dimethoxyphenol (negative control) or biotinylated-Compound 86 overnight, followed by incubation with NeutrAvidin agarose beads (Pierce, Rockford, Ill.) for 2 hours at 4° C. with gentle rotation. After spin down, beads were washed, boiled with SDS sample buffer to release bound protein, and western blotting was performed with anti-Hsp40 antibody (Abcam, Cambridge, Mass.). As shown in FIG. 15, while the biotinylated dimethoxyphenol did not associate with Hsp40 (lane (a)), the biotinylated Compound 86 associated with Hsp40 (lane (b)).

Figure 16:
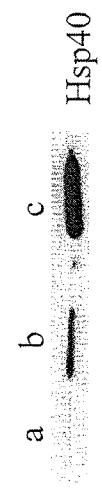
FIG. 16 is a western blot showing the association of Compound 86 with Hsp40 protein in A549 cell lysates, using the same protocol as in FIG. 15. Lane (a) is biotinylated dimethoxyphenol (negative control), lane (b) is biotinylated Compound 86, and lane (c) is A549 cell lysate (positive control).

A549 cell lysate was also incubated with biotinylated dimethoxyphenol (negative control) or biotinylated Compound 86 overnight, followed by incubation with NeutrAvidin agarose beads for 2 hours at 4° C. with gentle rotation. After spin down, beads were washed, boiled with SDS sample buffer to release bound protein, and western blot was performed with anti-Hsp40 antibody (Abcam). Again, as shown in FIG. 16, while the biotinylated dimethoxyphenol did not associate with Hsp40 (lane (a)), the biotinylated Compound 86 was associated with Hsp40 (lane(b)).

Figure 17:
FIG. 17 is a western blot showing the association of Compound 86 with recombinant Hsp40 protein, using the same protocol as in FIG. 15. Lane (a) is biotinylated dimethoxyphenol (negative control), lane (b) is biotinylated Compound 86, and lane (c) is recombinant Hsp40 protein (positive control).

Recombinant Hsp40 protein (Abcam) was incubated with biotinylated dimethoxyphenol (negative control) or biotinylated Compound 86 overnight, followed by incubation with NeutrAvidin agarose beads (Pierce, Rockford, Ill.) for 2 hours at 4° C. with gentle rotation. After spin down, beads were washed, boiled with SDS sample buffer to release bound protein, and western blot was performed with anti-Hsp40 antibody (Abcam). Biotinylated Compound 86 associated with recombinant Hsp40 protein. As shown in FIG. 17, while the biotinylated dimethoxyphenol did not associate with the recombinant Hsp40 (lane (a)), the biotinylated Compound 86 did associate with the recombinant Hsp40 protein (lane(b)).

Example 40

Figure 18:
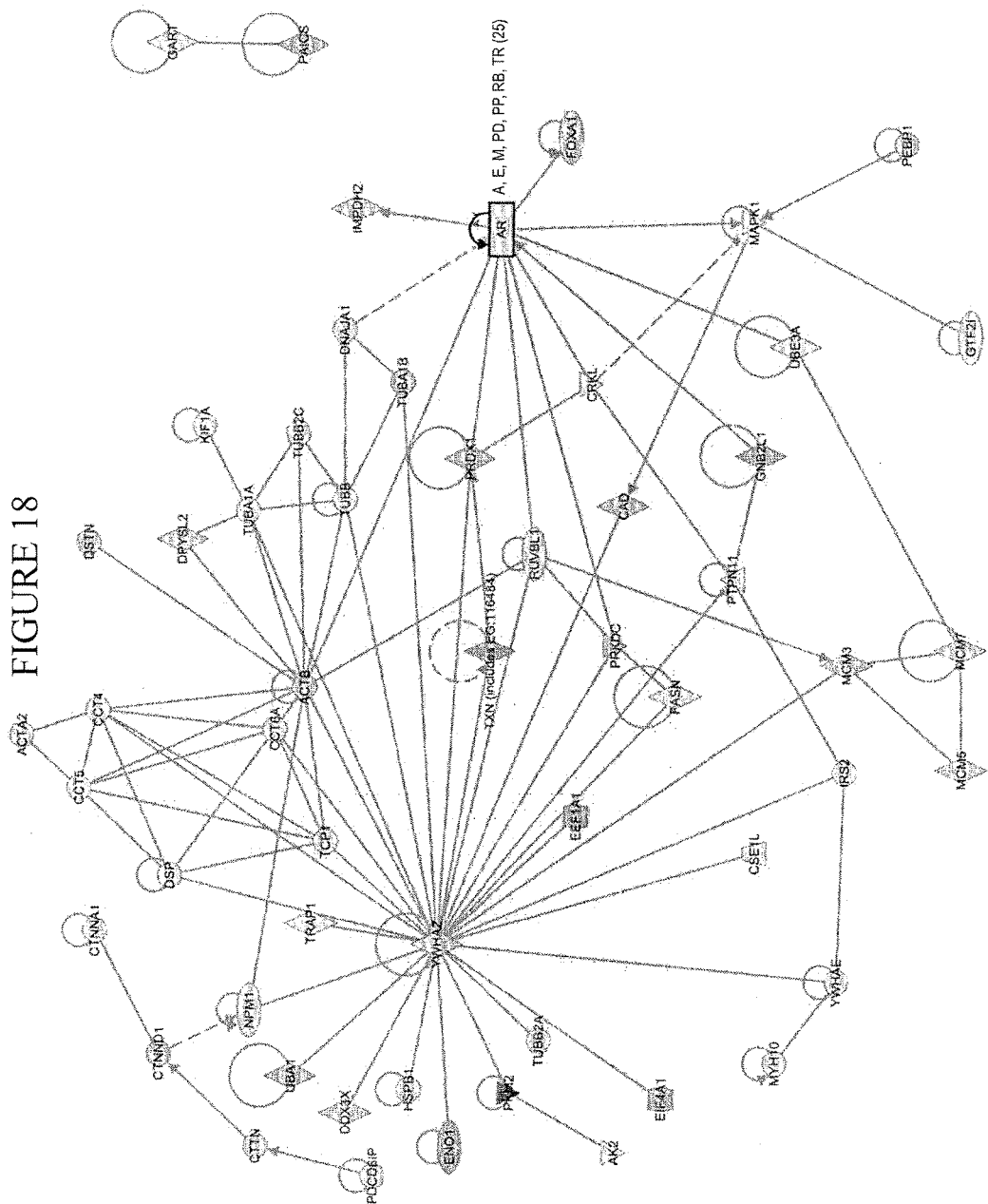
FIG. 18 depicts the cancer network associated with Compound 86, as determined by Ingenuity Pathway Analysis of mass spectrometric data obtained on proteins associated with the compound.

This example further illustrates that Compound 86 associates with Hsp40 protein. A biotinylated version of Compound 86 and a biotinylated version of an inactive analogue of Compound 86 were prepared and used in conjunction with NeutrAvidin beads to pull down Compound 86-associated proteins from prostate cancer cell lysates, and assess the specificity of that association by comparison of proteins pulled down with the inactive analogue of Compound 86. Mass spectrometry was used to identify the proteins associated with the compound. A bioinformatics analysis was carried out on the associated proteins using the Ingenuity Pathway Analysis (IPA) software (http://www.ingenuity.com) to investigate the cancer network associated with the pulled down proteins. FIG. 18 depicts the cancer network associated with Compound 86. As can be seen from FIG. 18, DNAJ1, also known as Hsp40, was identified as one of the proteins associated with Compound 86. As the chaperone protein is inhibited, the AR becomes down-regulated.

Example 41

This example illustrates that Compound 86 has an impact on AR-driven gene expression (PSA) and androgen-independent AR-driven gene expression (e.g., UBE2C). A microarray analysis was performed on the genome-wide transcriptional response to Compound 86 compared with the antiandrogens bicalutamide and MDV3100, and solvent DMSO. Each compound was tested at two concentrations: 1 and 5 μM. The data were subjected to bioinformatics analysis using the Partek Genomics Software. The principal component analysis (PCA) results are shown in FIG. 19. The PCA in FIG. 19A shows that Compound 86 has a distinctive transcriptional response when compared to DMSO, bicalutamide or MDV3100. FIG. 19B depicts a different view in 3-dimensional space again reinforcing the differences between Compound 86 versus DMSO, bicalutamide and MDV3100. This visual assessment is consistent with the data showing that Compound 86 and not DMSO, bicalutamide, or MDV3100, can inhibit the androgen-independent, androgen receptor-dependent transcriptional program of castrate-resistant prostate cancer.

FIG. 20 depicts the hierarchical clustering of genes that showed a greater than 2-fold difference between Compound 86 and DMSO control.

FIG. 21 depicts an Ingenuity Pathway Analysis of the prostate pathway of genes significantly regulated by Compound 86 in LNCaP human prostate carcinoma cells.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of inhibiting androgen-independent AR activation in a human subject that has prostate cancer, comprising administering to the subject an effective amount of a compound of Formula I:

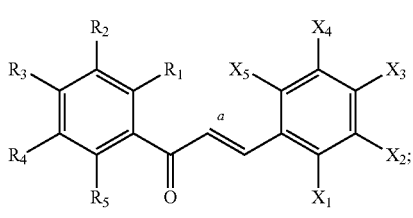

wherein $R_1$ to $R_5$ are the same or different and are each selected from H and $C_1$-$C_6$ alkoxy;
wherein $X_1$ to $X_5$ are the same or different and are each selected from H and the electron withdrawing groups of $NO_2$, CN, and $CF_3$; and
wherein bond "a" can be in either the E or Z form;
with the proviso that $R_1$ to $R_5$ and $X_1$ to $X_5$ cannot all be H simultaneously;
or a pharmaceutically acceptable salt, solvate, or stereoisomer thereof.

2. A method of inhibiting progesterone receptor (PR) and/or estrogen receptor (ER) activation in a human subject comprising administering to the subject an effective amount of a compound of Formula I:

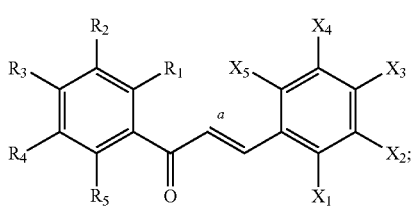

wherein $R_1$ to $R_5$ are the same or different and are each selected from H and $C_1$-$C_6$ alkoxy;
wherein $X_1$ to $X_5$ are the same or different and are each selected from H and the electron withdrawing groups of $NO_2$, CN, and $CF_3$; and
wherein bond "a" can be in either the E or Z form;
with the proviso that $R_1$ to $R_5$ and $X_1$ to $X_5$ cannot all be H simultaneously;
or a pharmaceutically acceptable salt, solvate, or stereoisomer thereof.

3. A method of modulating Hsp40 in a human subject comprising administering to the subject an effective amount of a compound of Formula I:

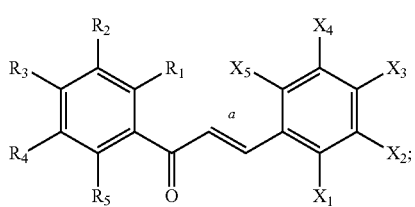

wherein $R_1$ to $R_5$ are the same or different and are each selected from H and $C_1$-$C_6$ alkoxy;
wherein $X_1$ to $X_5$ are the same or different and are each selected from H and the electron withdrawing groups of $NO_2$, CN, and $CF_3$; and
wherein bond "a" can be in either the E or Z form;
with the proviso that $R_1$ to $R_5$ and $X_1$ to $X_5$ cannot all be H simultaneously;
or a pharmaceutically acceptable salt, solvate, or stereoisomer thereof.

4. The method of claim 1, wherein the compound is one of the following:

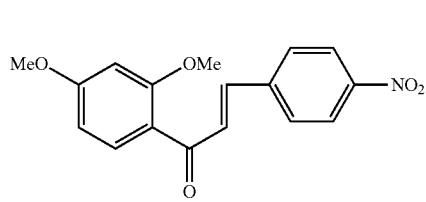

Compound 2

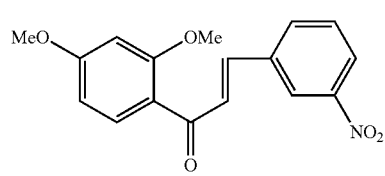

Compound 3

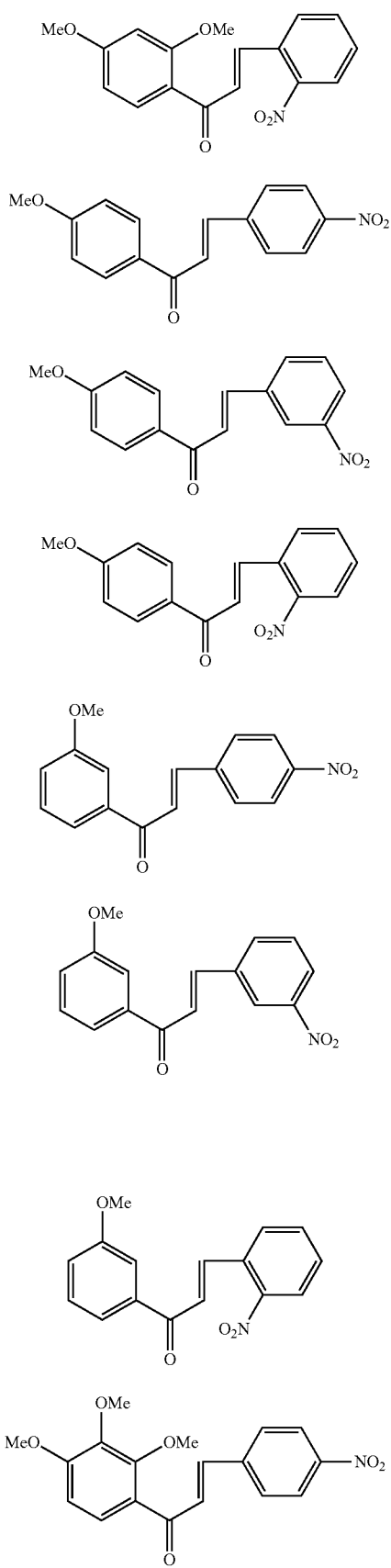
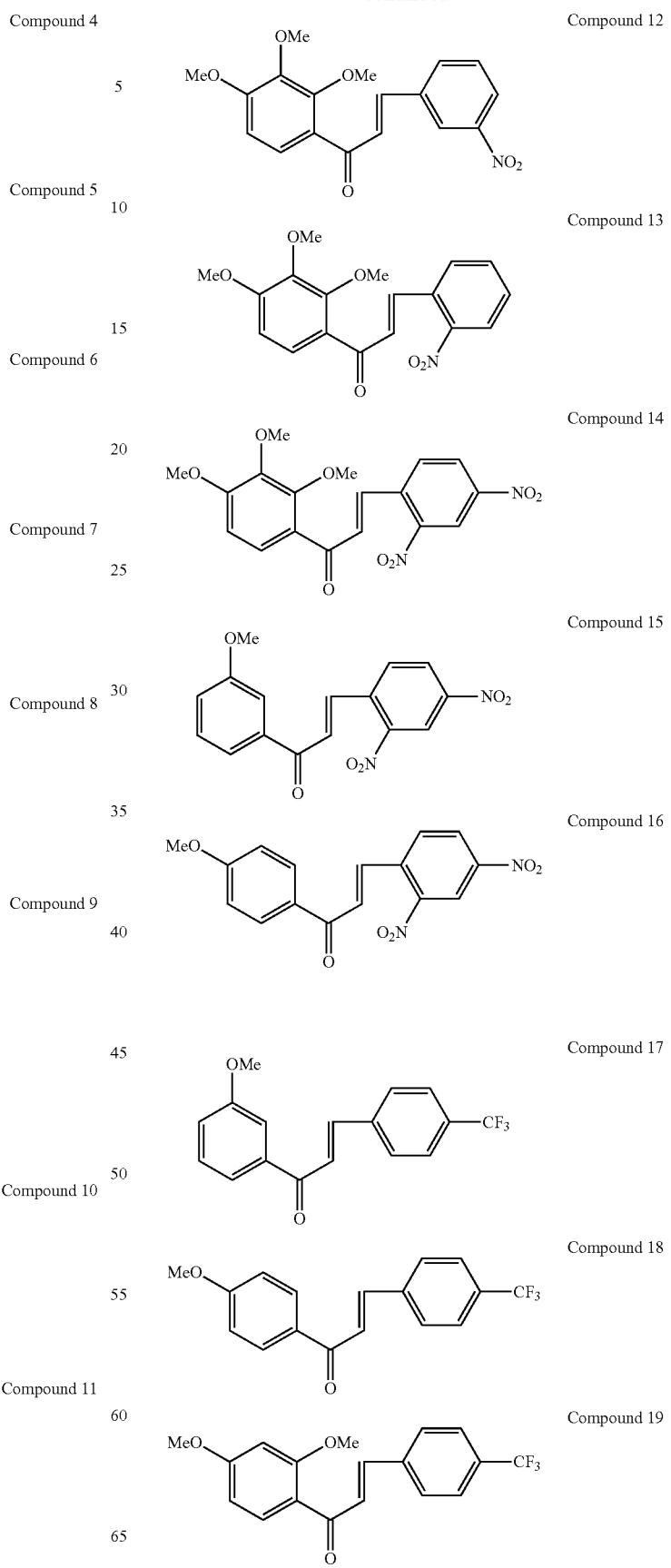

-continued
Compound 20
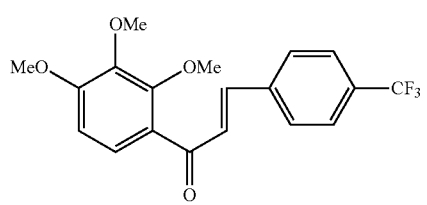
Compound 21
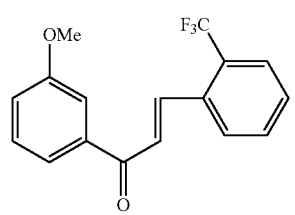
Compound 22
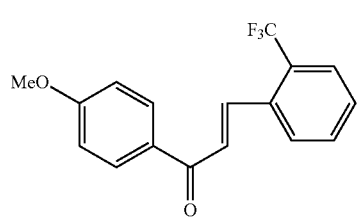
Compound 23
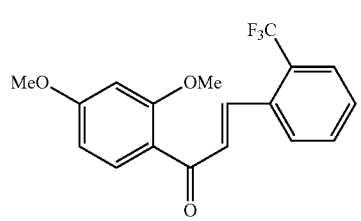
Compound 24
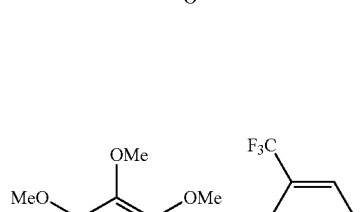
Compound 25
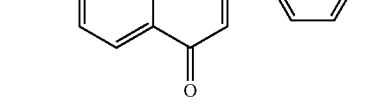
Compound 26
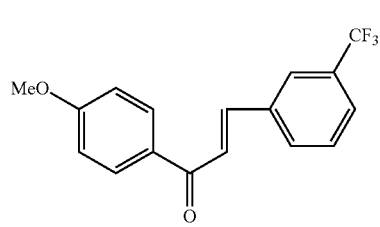
-continued
Compound 27
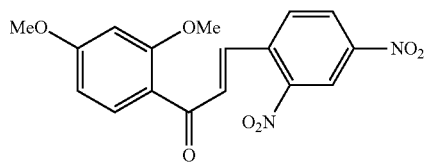
Compound 28
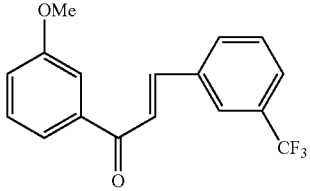
Compound 29
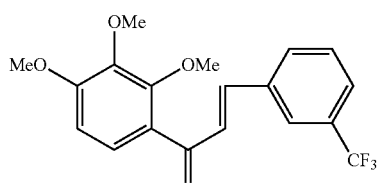
Compound 30
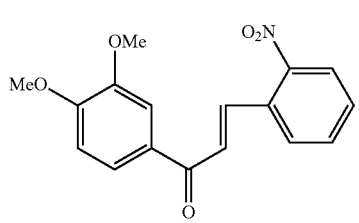
Compound 31
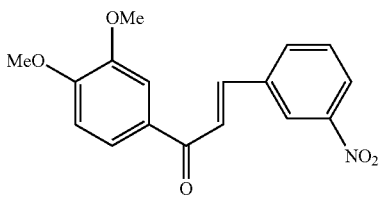
Compound 32
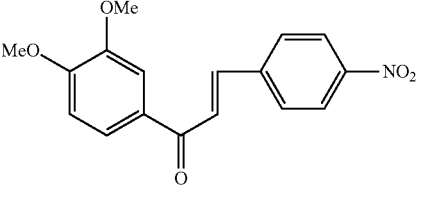
Compound 33
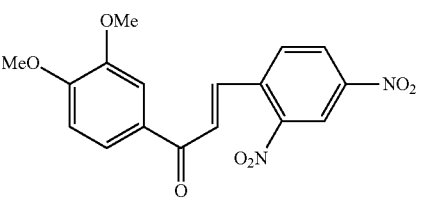
Compound 34
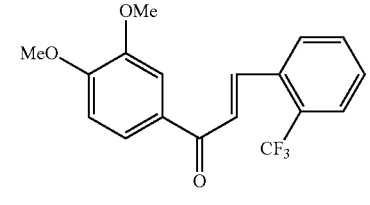

Compound 35
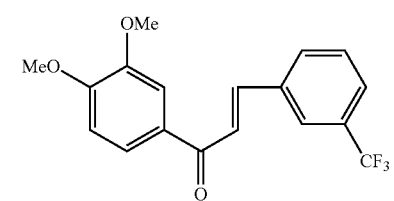
Compound 36
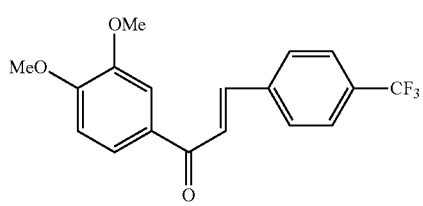
Compound 37
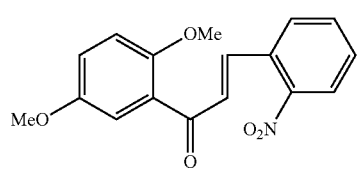
Compound 38
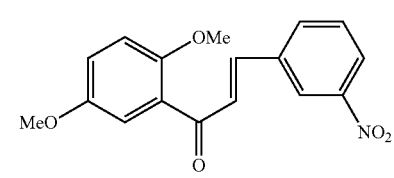
Compound 39
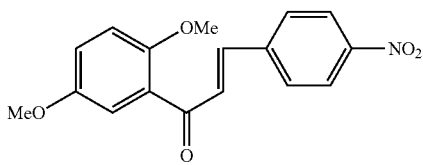
Compound 40
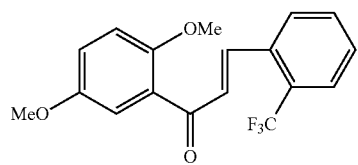
Compound 41
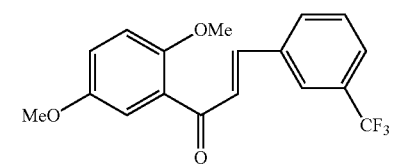
Compound 42
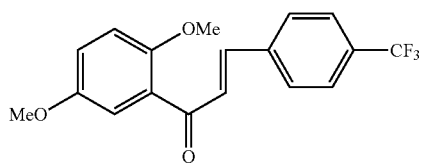
Compound 43
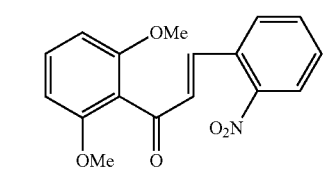
Compound 44
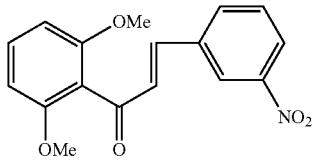
Compound 45
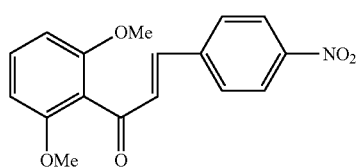
Compound 46
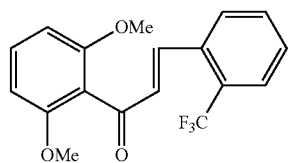
Compound 47
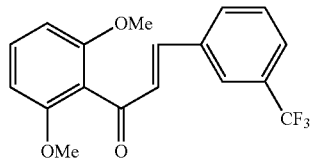
Compound 48
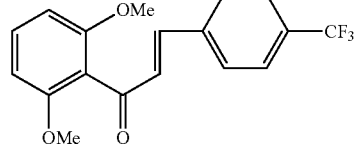
Compound 49
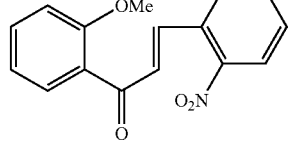
Compound 50
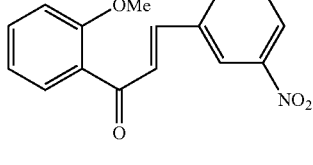
Compound 51
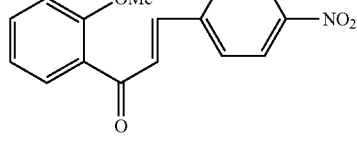
Compound 52
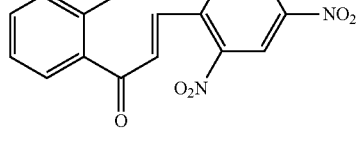

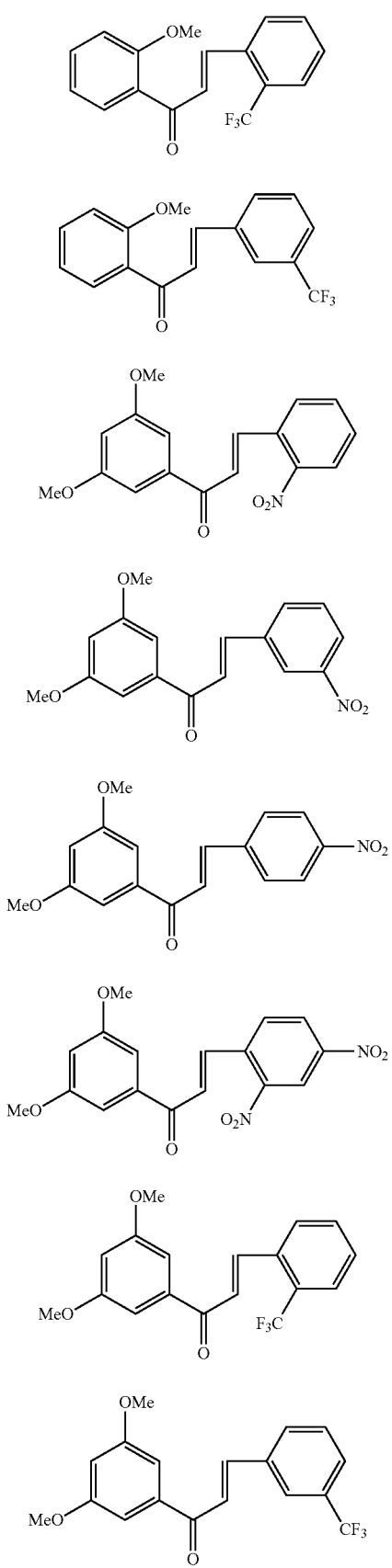
Compound 53
Compound 54
Compound 55
Compound 56
Compound 57
Compound 58
Compound 59
Compound 60
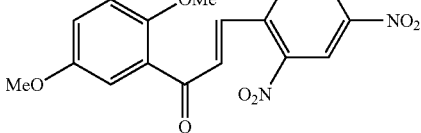
Compound 61
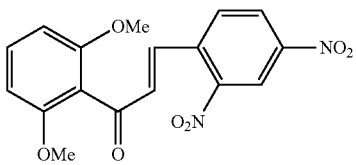
Compound 62
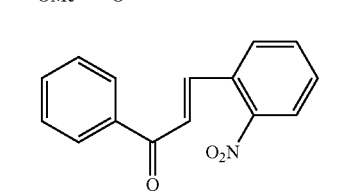
Compound 63
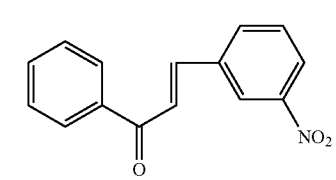
Compound 64
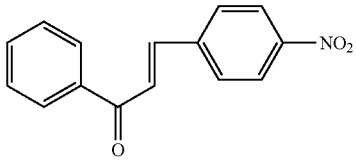
Compound 65
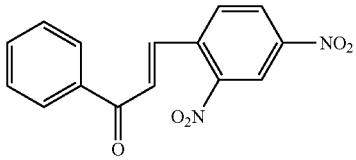
Compound 66
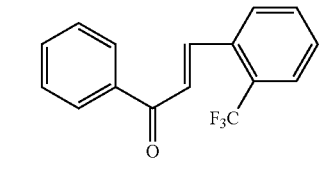
Compound 67
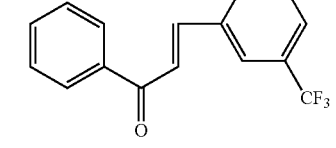
Compound 68
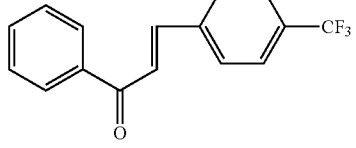
Compound 69

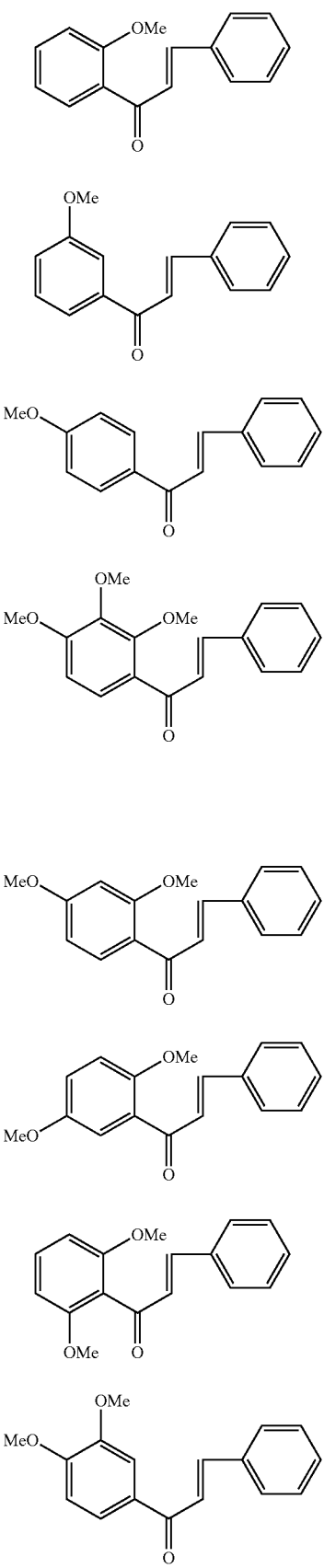
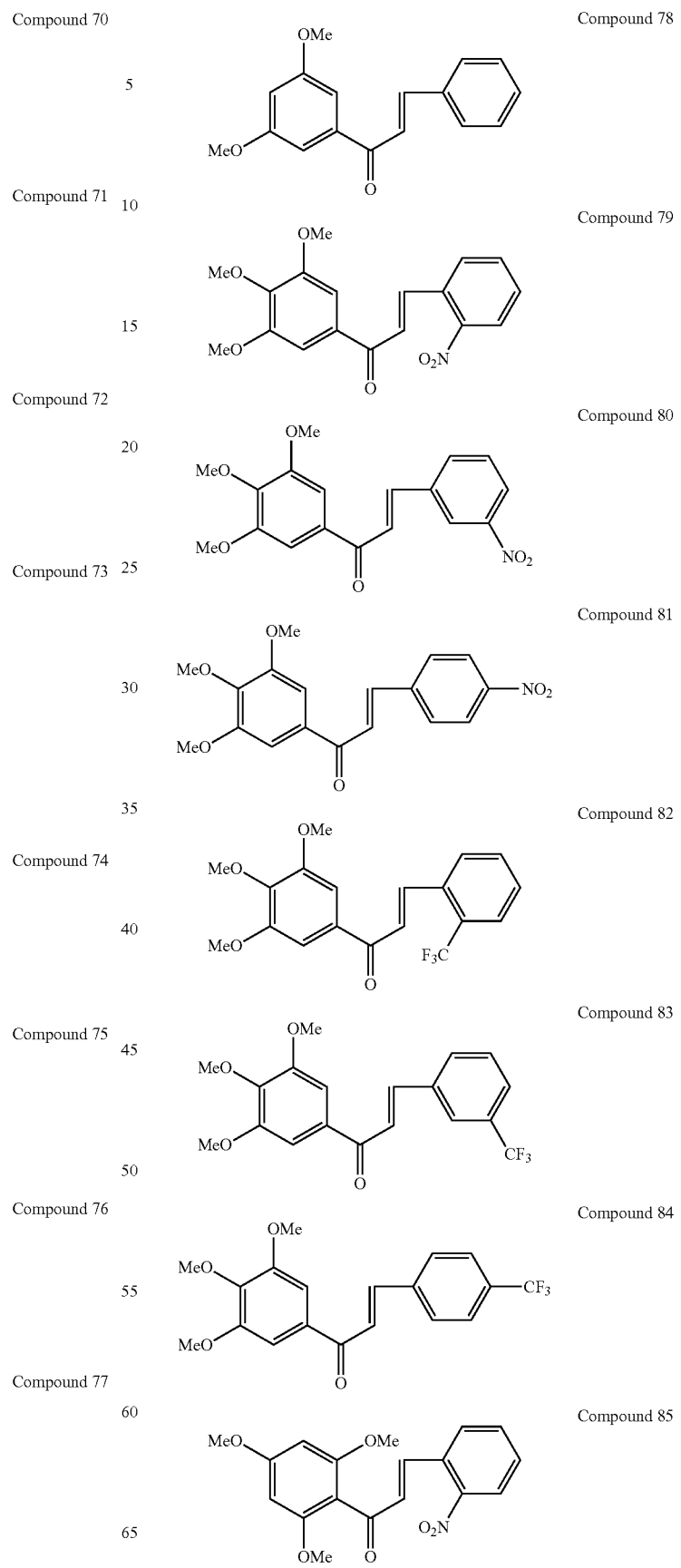

Compound 86
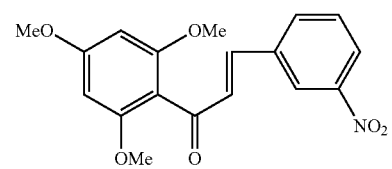
Compound 87
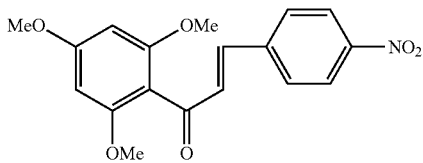
Compound 88
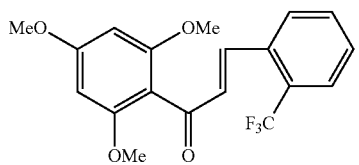
Compound 89
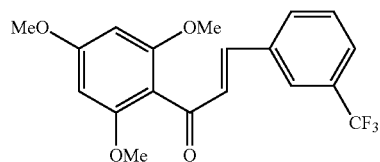
Compound 90
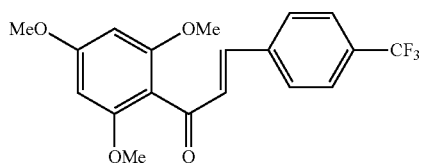
Compound 91
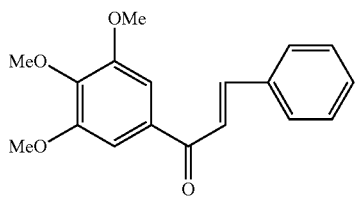
Compound 92
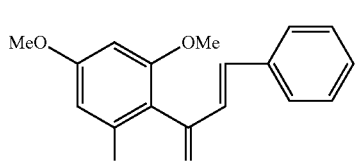
Compound 93
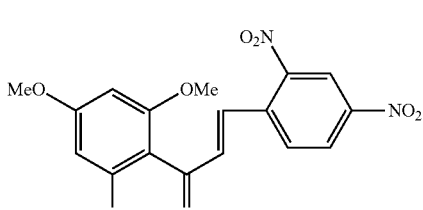
Compound 94
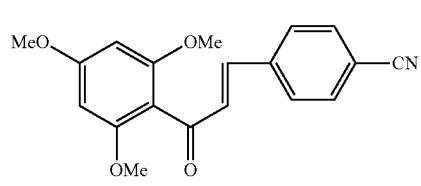
Compound 95
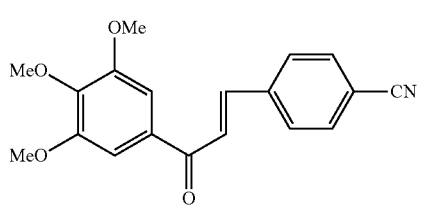
Compound 96
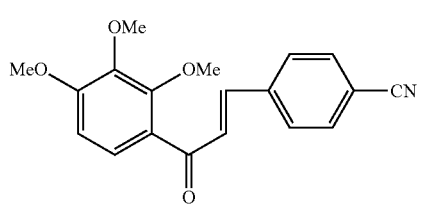
Compound 97
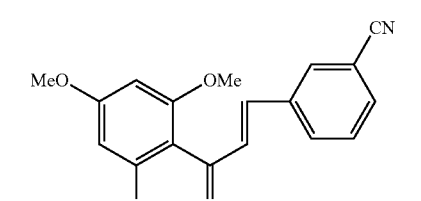
Compound 98
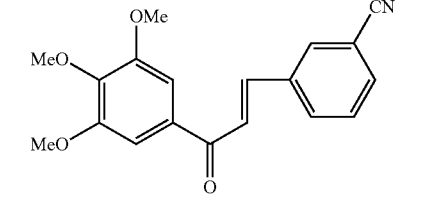
Compound 99
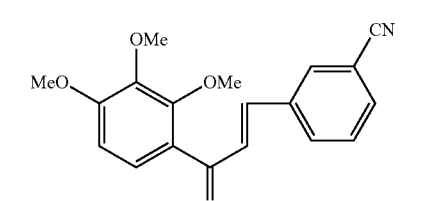
Compound 100
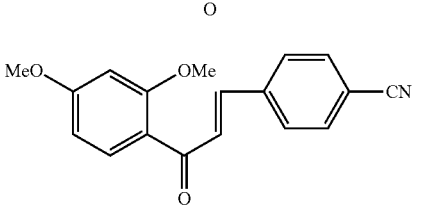
Compound 101
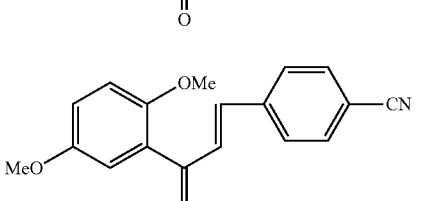
Compound 102
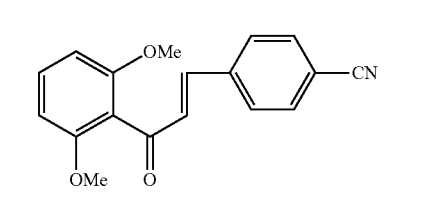

Compound 103
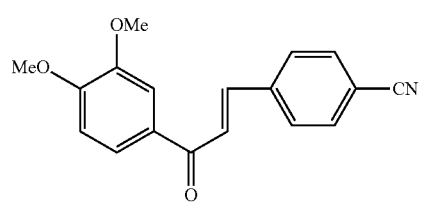
Compound 104
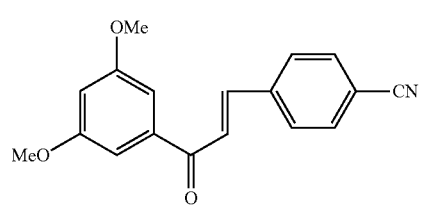
Compound 105
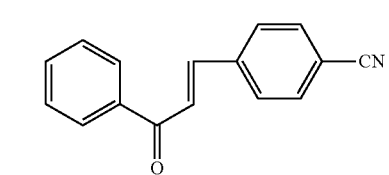
Compound 106
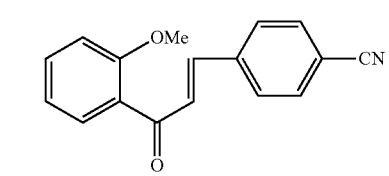
Compound 107
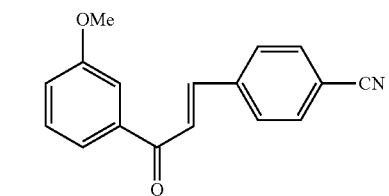
Compound 108
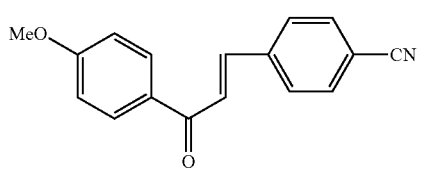
Compound 109
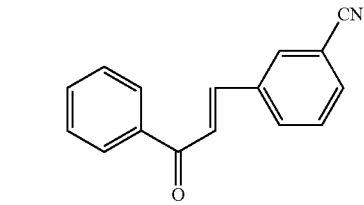
Compound 110
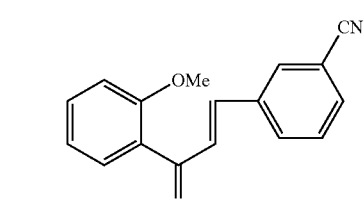
Compound 111
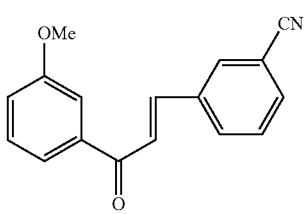
Compound 112
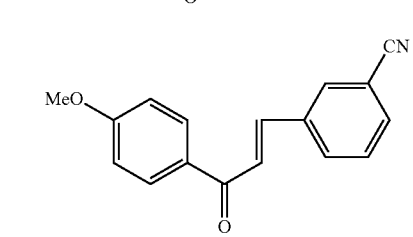
Compound 113
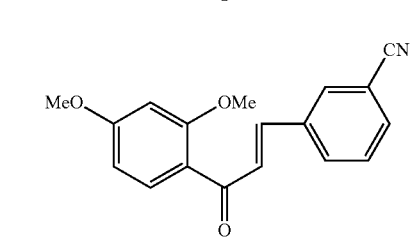
Compound 114
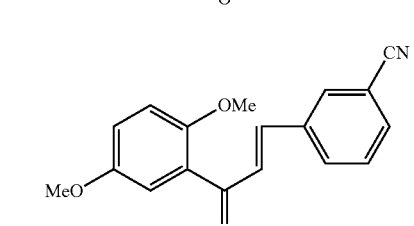
Compound 115
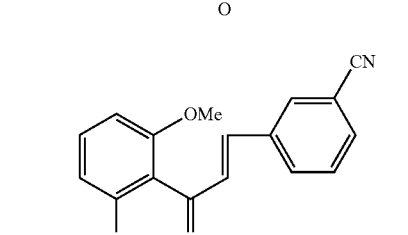
Compound 116
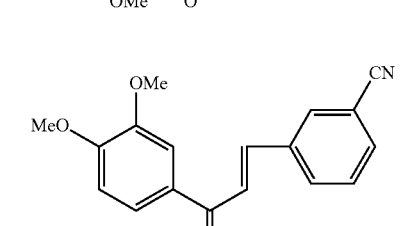
or
Compound 117
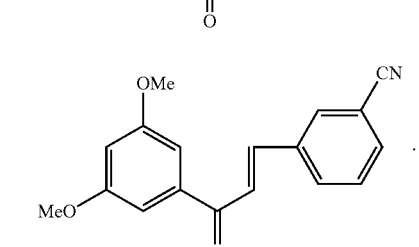
.
5. The method of claim 1, wherein the compound is one of the following:

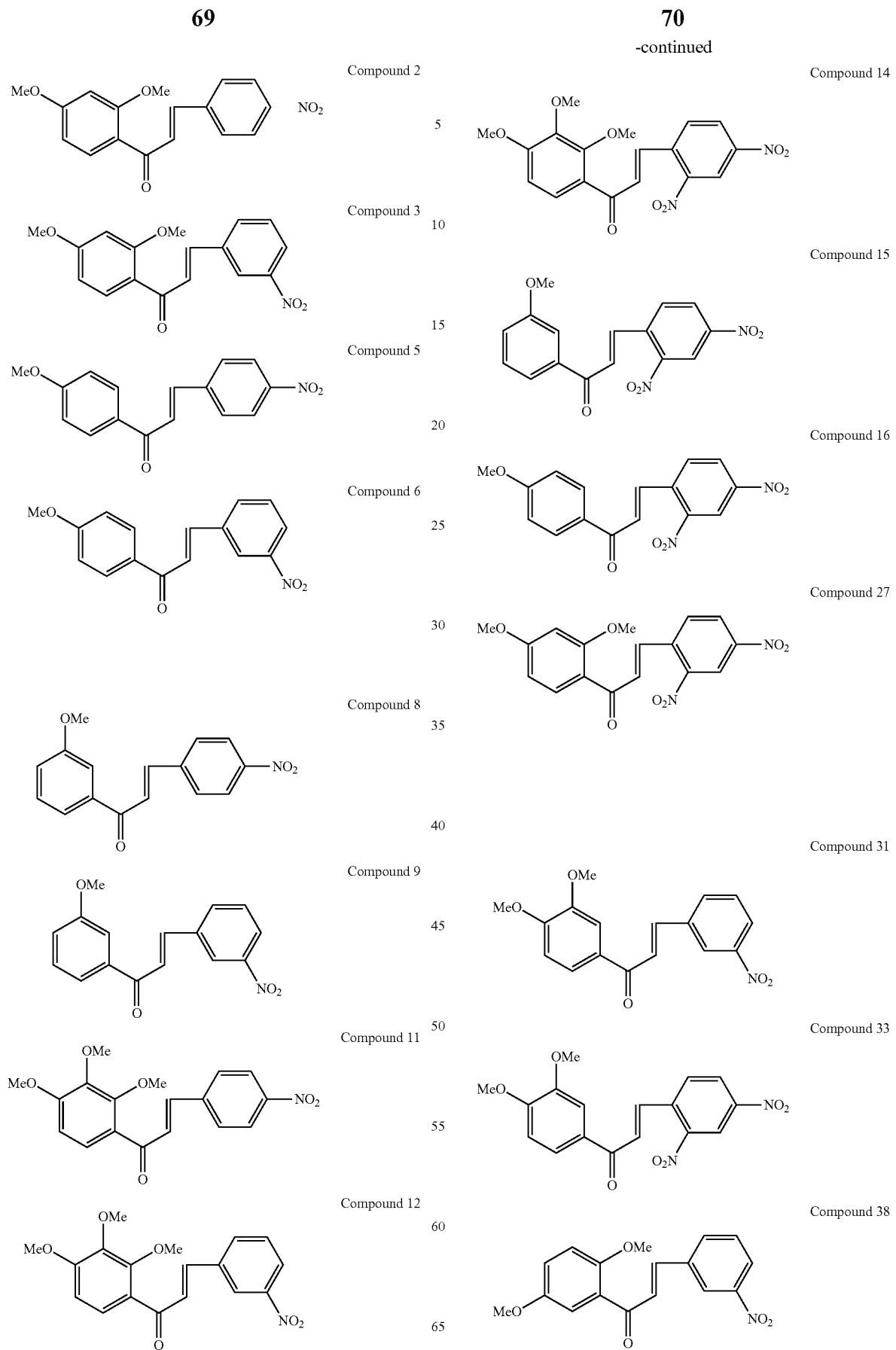

Compound 39
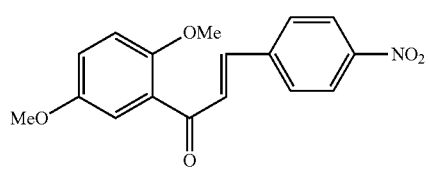
Compound 44
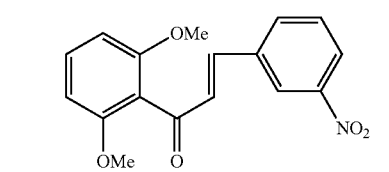
Compound 45
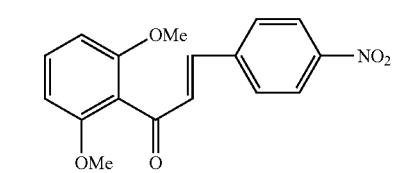
Compound 50
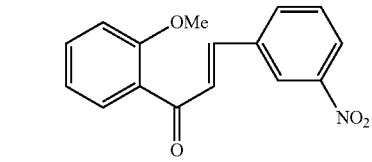
Compound 51
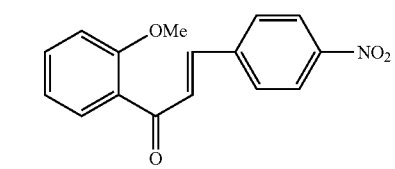
Compound 52
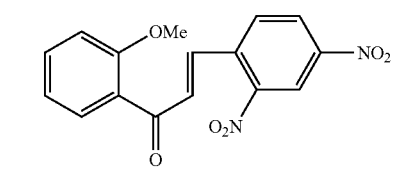
Compound 56
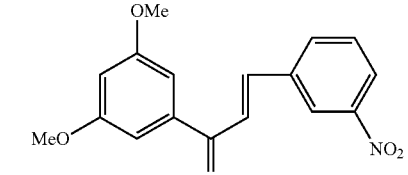
Compound 57
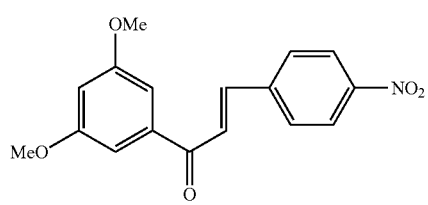
Compound 58
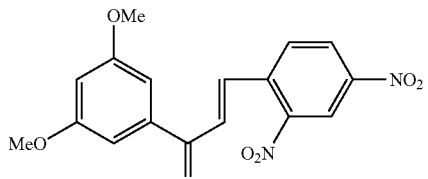
Compound 61
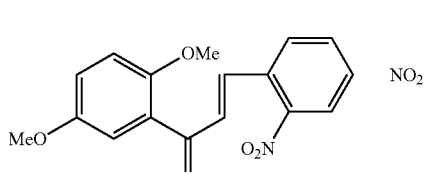
Compound 62
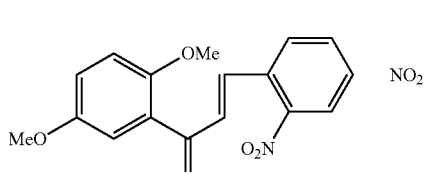
Compound 66
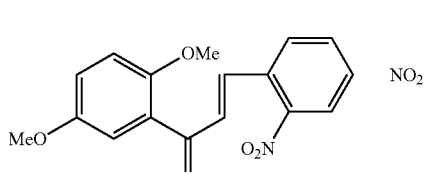
Compound 80
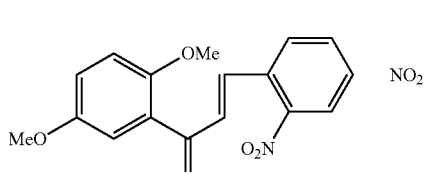
Compound 86
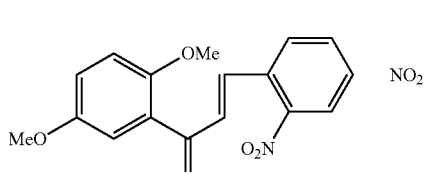
Compound 87
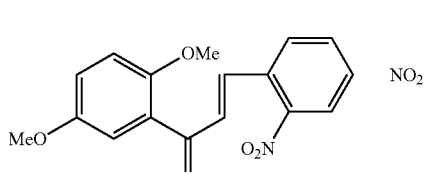
Compound 93
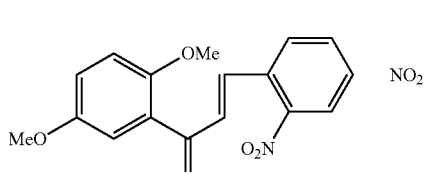

Compound 94
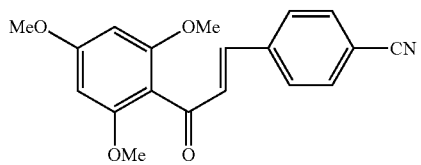
Compound 95
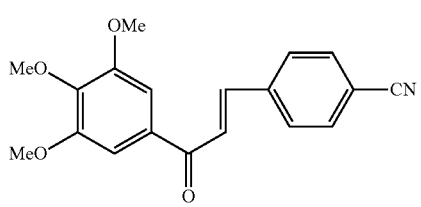
Compound 96
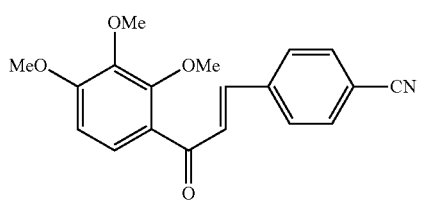
Compound 97
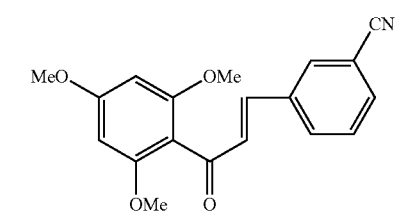
Compound 98
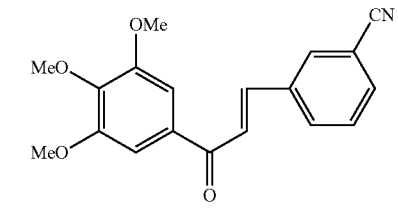
Compound 99
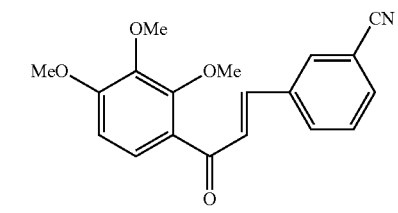
Compound 100
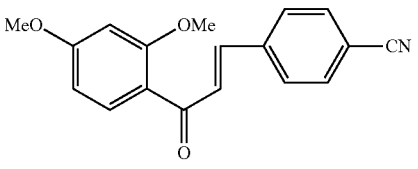
Compound 101
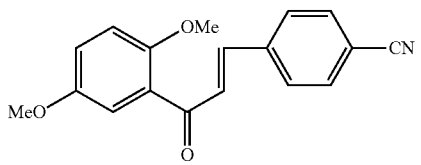
Compound 102
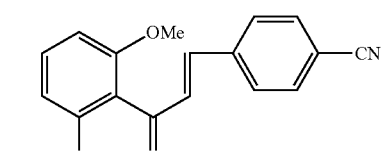
Compound 103
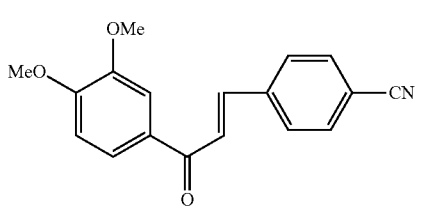
Compound 104
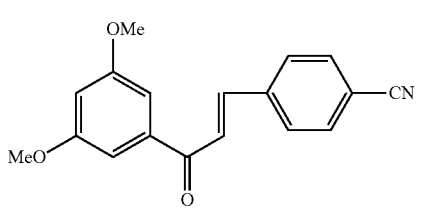
Compound 105
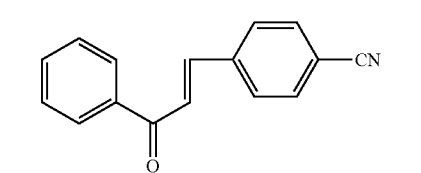
Compound 106
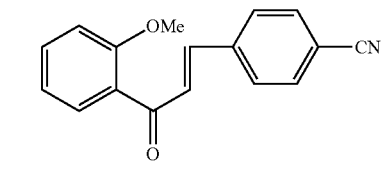
Compound 107
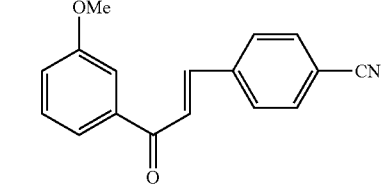
Compound 108
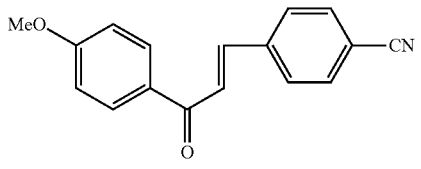

Compound 109
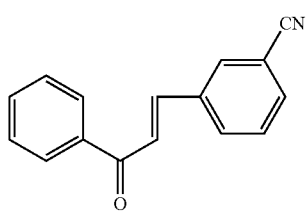
Compound 110
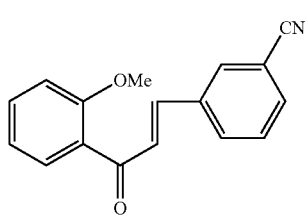
Compound 111
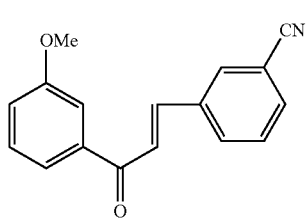
Compound 112
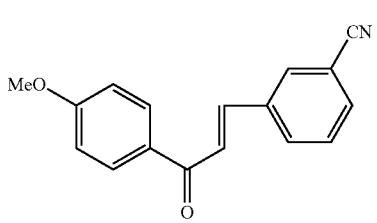
Compound 113
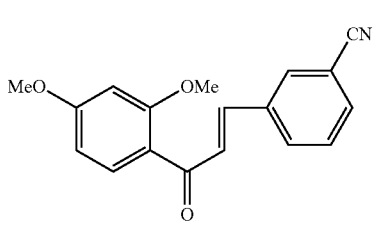
Compound 114
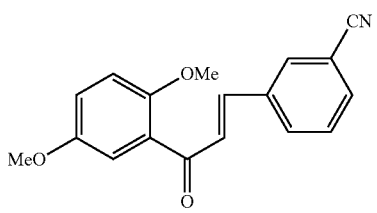
Compound 115
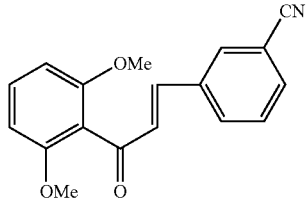
Compound 116
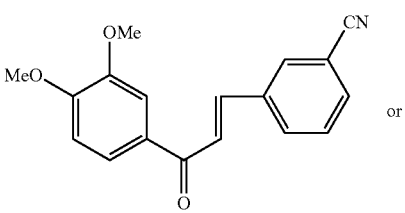
or
Compound 117
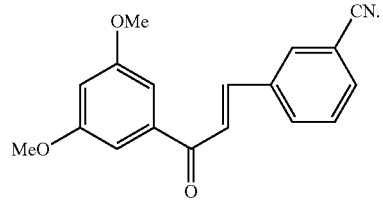
6. The method of claim 1, wherein the compound is
(compound 86)
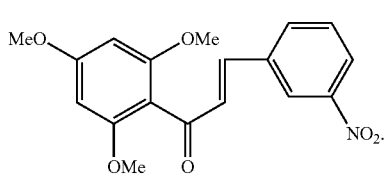
7. The method of claim 2, wherein the compound is one of the following:
Compound 2
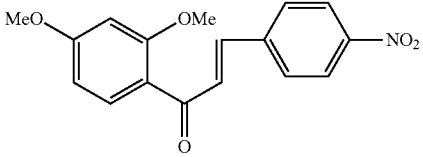
Compound 3
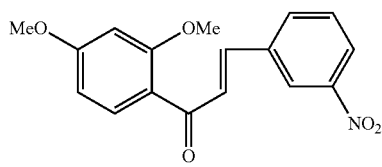
Compound 4
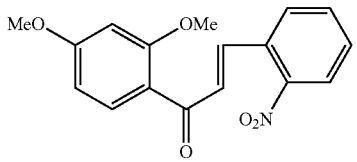
Compound 5
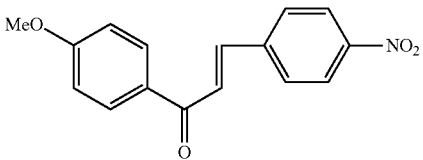

Compound 6
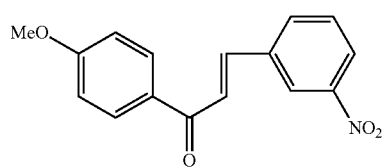
Compound 7
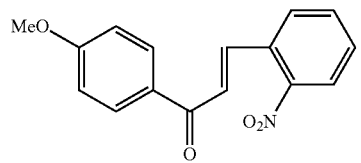
Compound 8
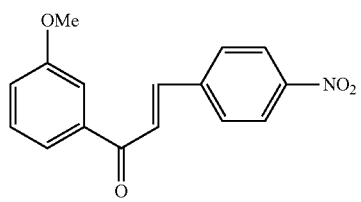
Compound 9
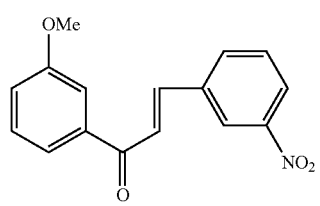
Compound 10
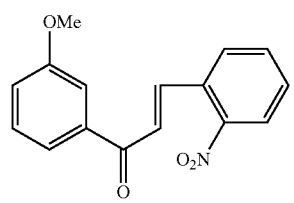
Compound 11
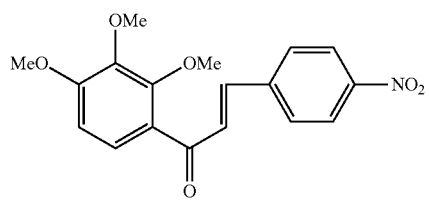
Compound 12
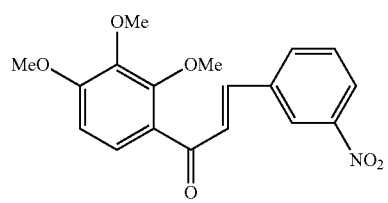
Compound 13
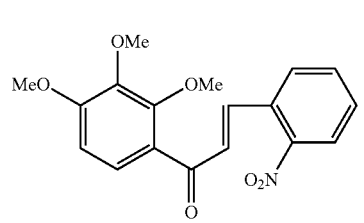
Compound 14
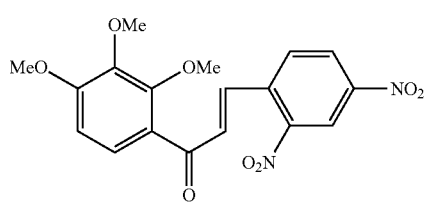
Compound 15
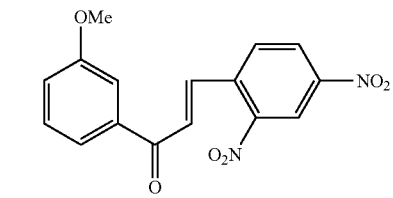
Compound 16
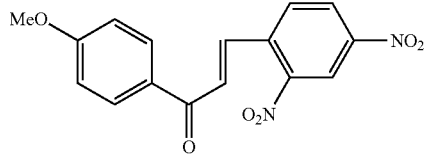
Compound 17
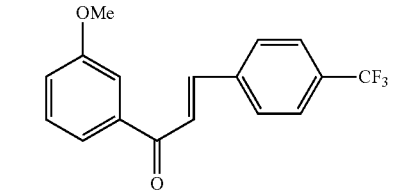
Compound 18
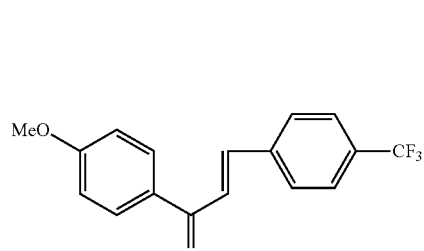
Compound 19
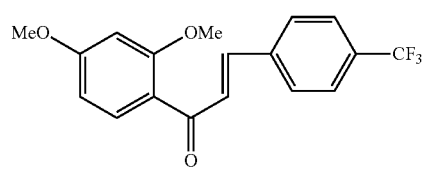
Compound 20
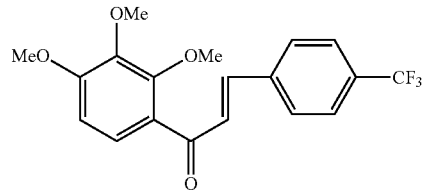

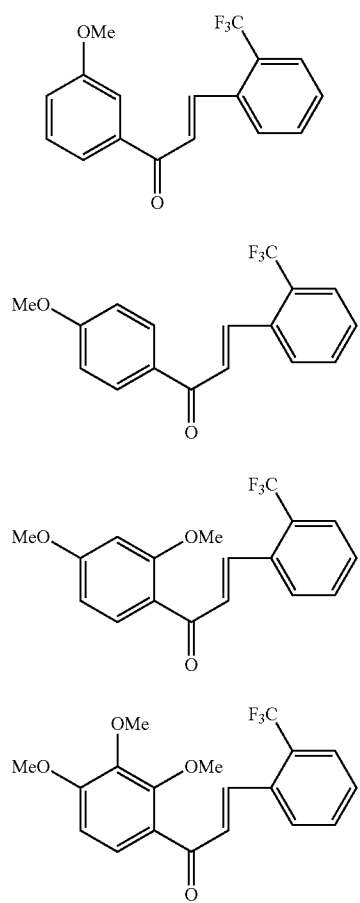
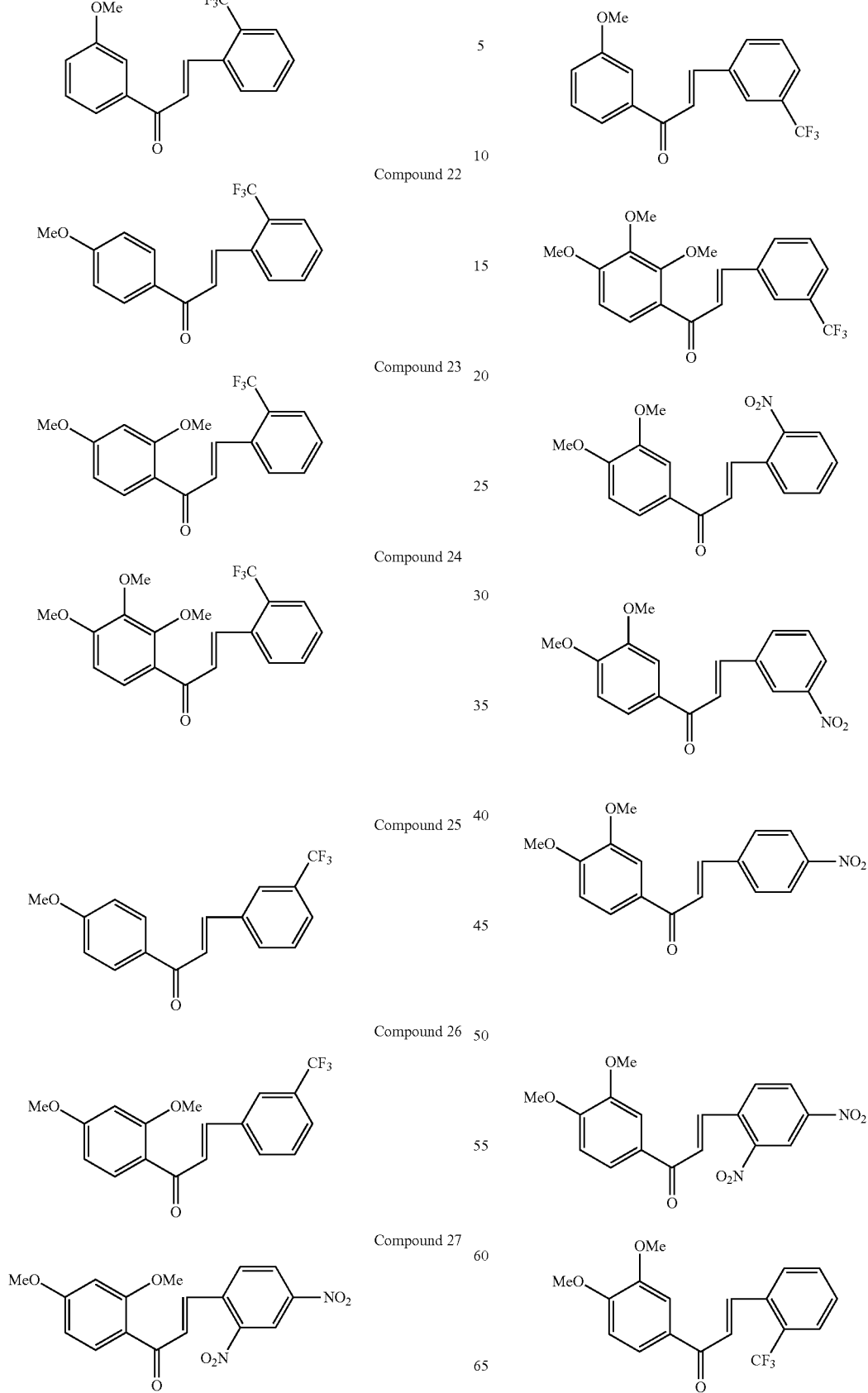

-continued
Compound 35
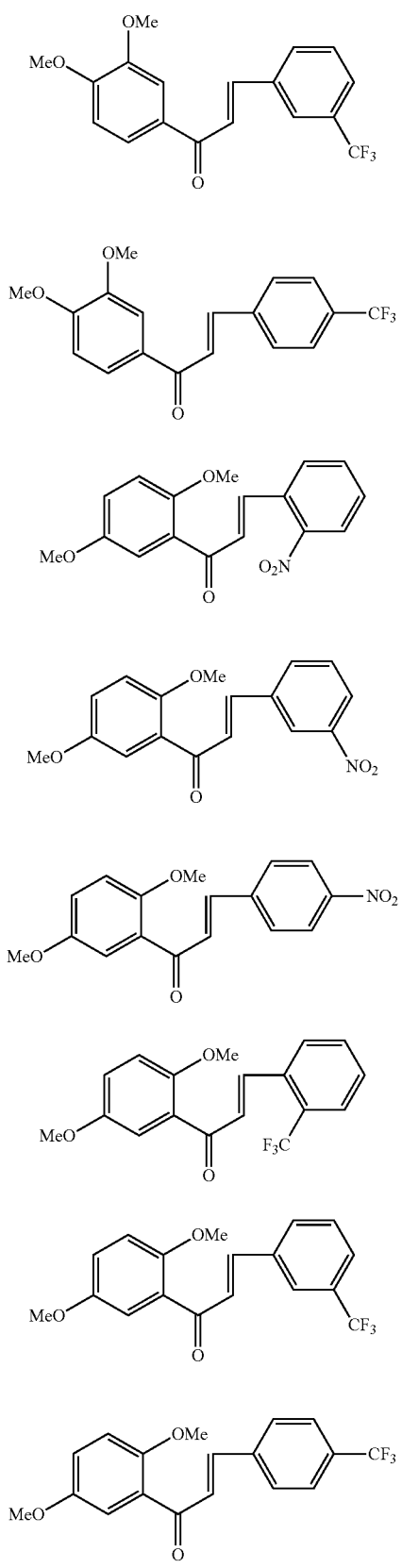
Compound 36
Compound 37
Compound 38
Compound 39
Compound 40
Compound 41
Compound 42
-continued
Compound 43
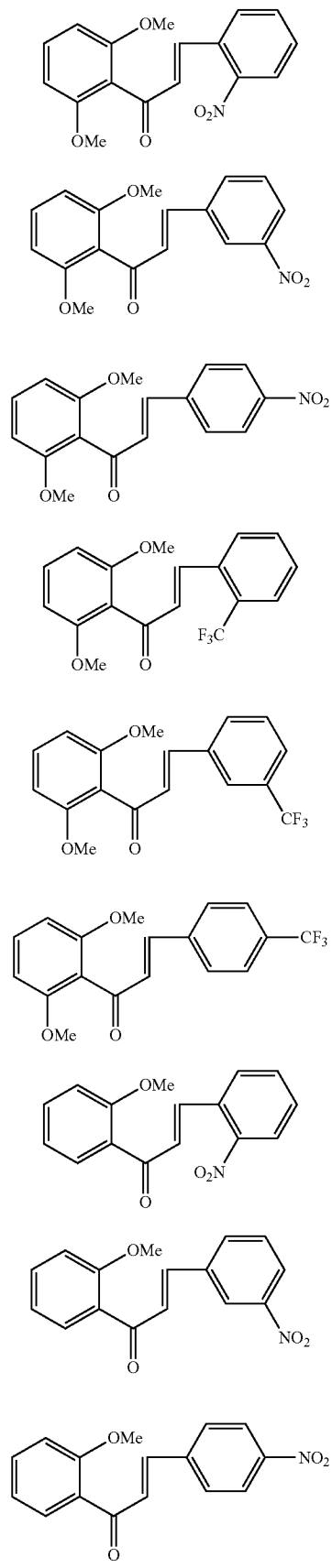
Compound 44
Compound 45
Compound 46
Compound 47
Compound 48
Compound 49
Compound 50
Compound 51

Compound 52
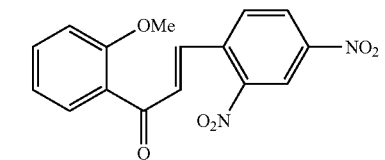
Compound 53
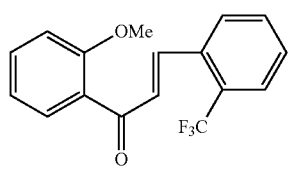
Compound 54
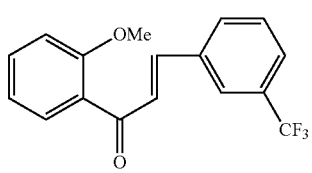
Compound 55
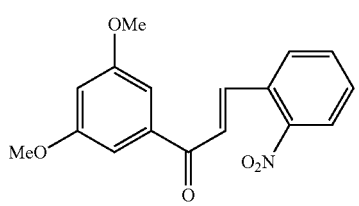
Compound 56
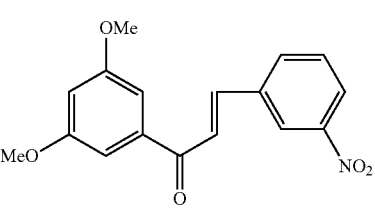
Compound 57
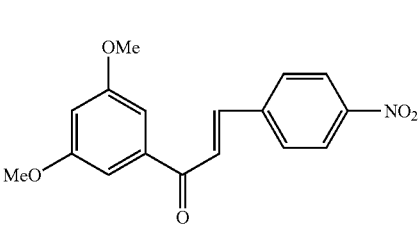
Compound 58
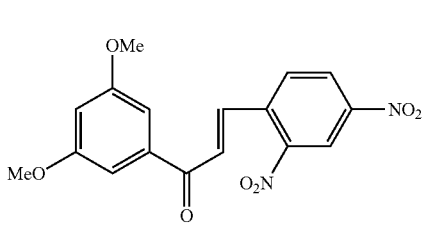
Compound 59
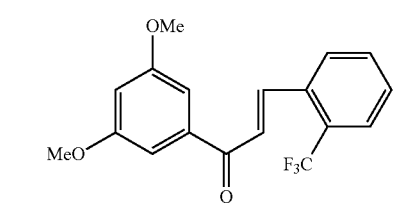
Compound 60
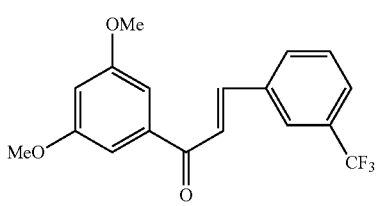
Compound 61
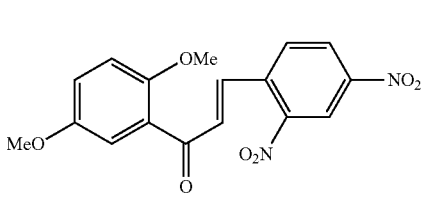
Compound 62
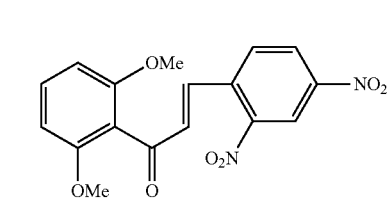
Compound 63
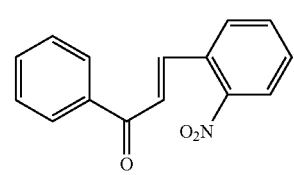
Compound 64
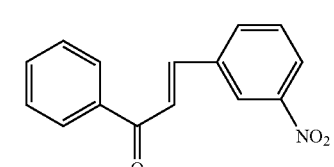
Compound 65
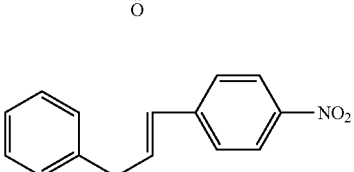
Compound 66
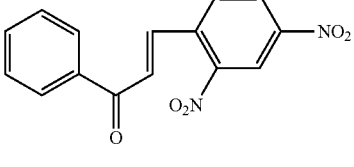
Compound 67
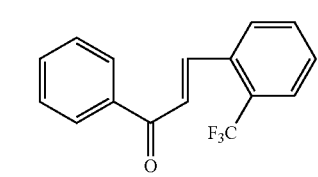

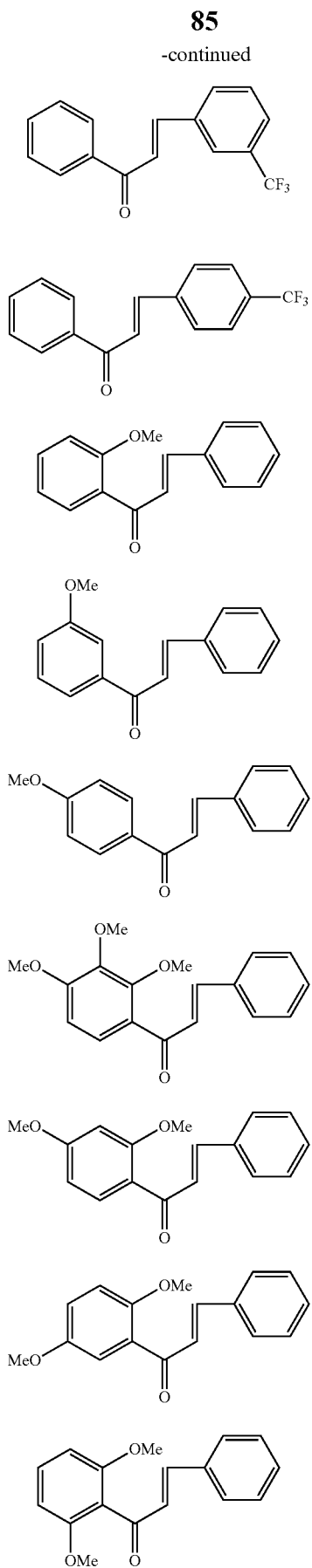
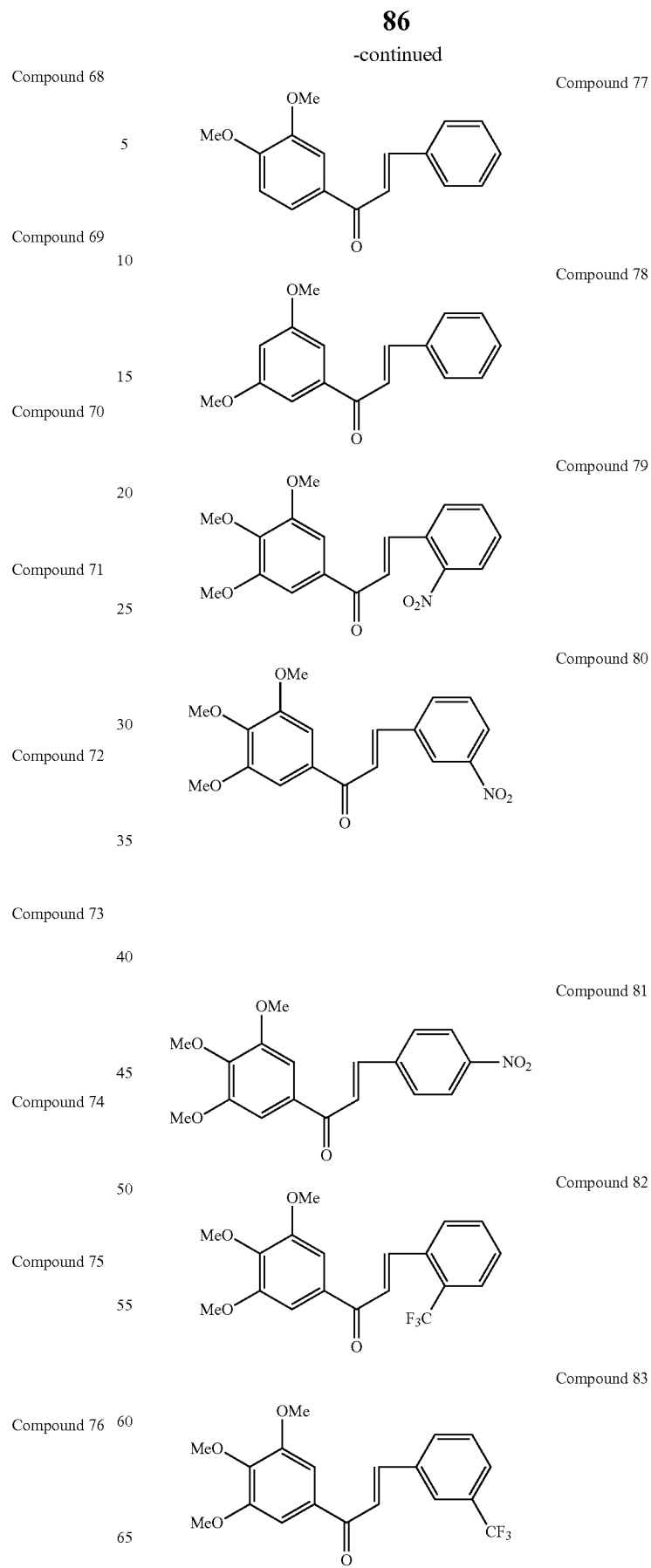

Compound 84
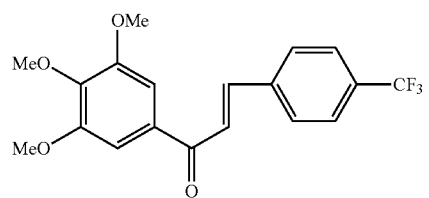
Compound 85
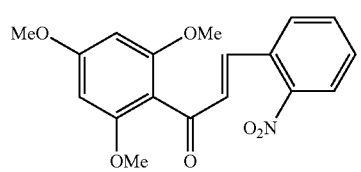
Compound 86
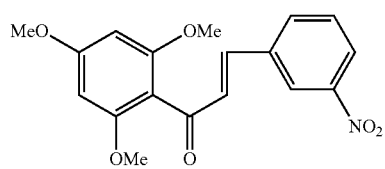
Compound 87
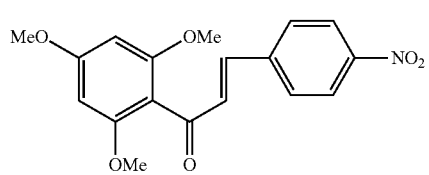
Compound 88
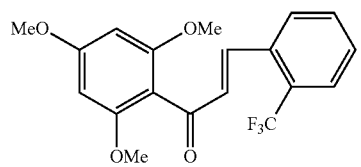
Compound 89
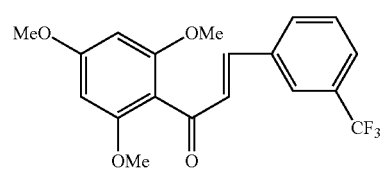
Compound 90
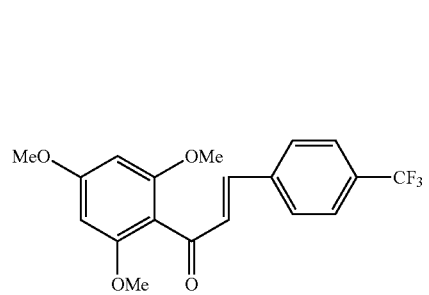
Compound 91
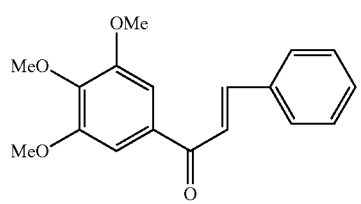
Compound 92
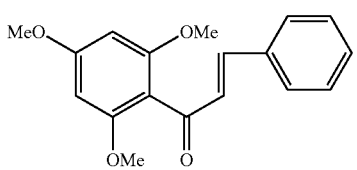
Compound 93
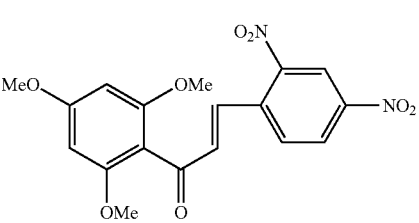
Compound 94
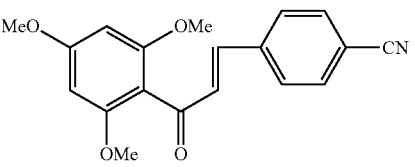
Compound 95
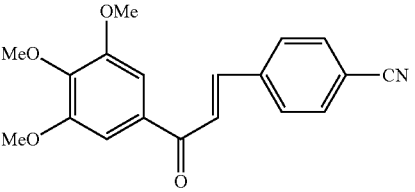
Compound 96
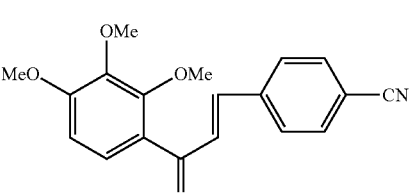
Compound 97
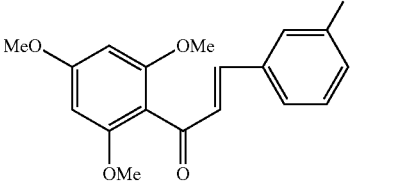
Compound 98
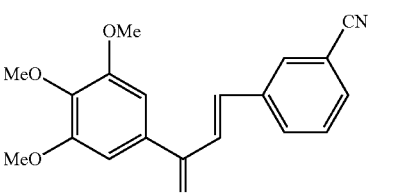

Compound 99
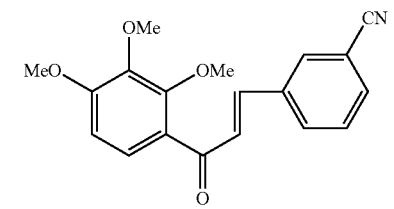
Compound 100
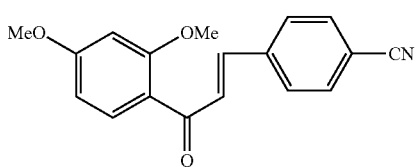
Compound 101
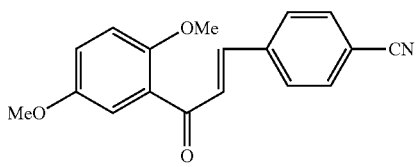
Compound 102
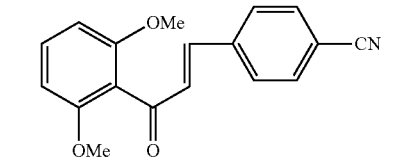
Compound 103
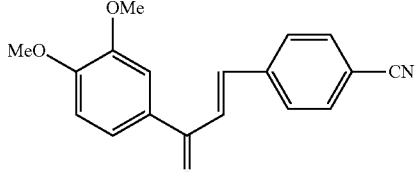
Compound 104
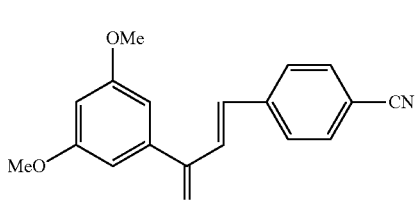
Compound 105
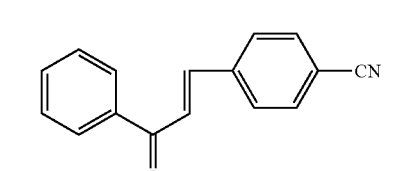
Compound 106
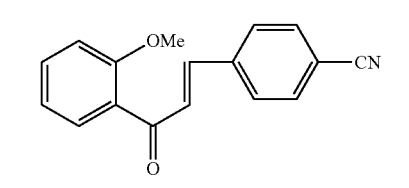
Compound 107
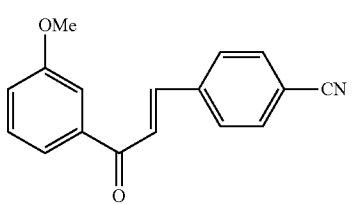
Compound 108
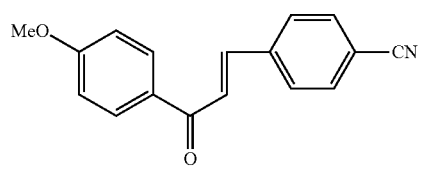
Compound 109
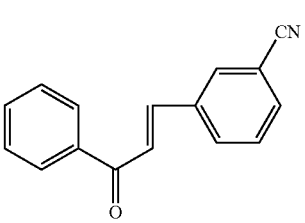
Compound 110
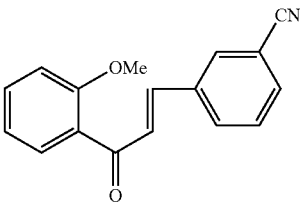
Compound 111
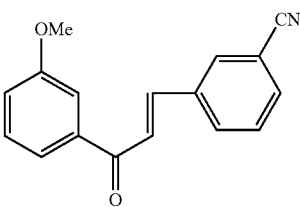
Compound 112
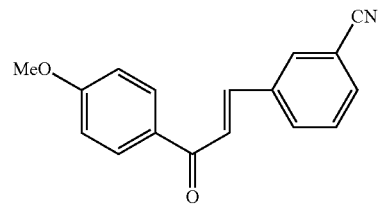
Compound 113
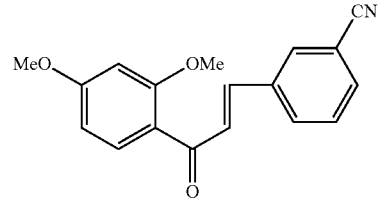

Compound 114
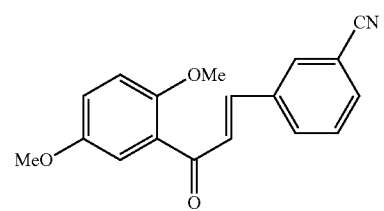
Compound 115
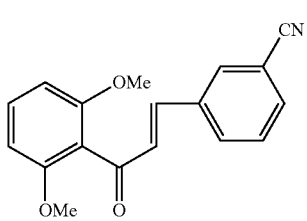
Compound 116
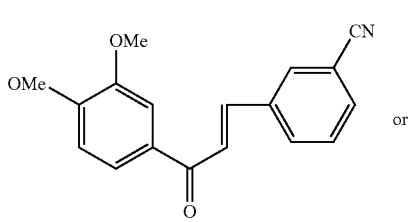
or
Compound 117
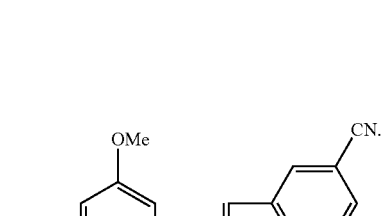
8. The method of claim 2, wherein the compound is one of the following:
Compound 2
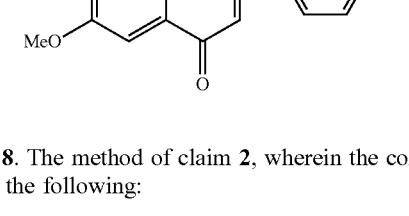
Compound 3
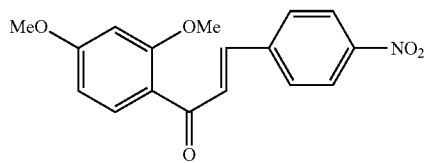
Compound 5
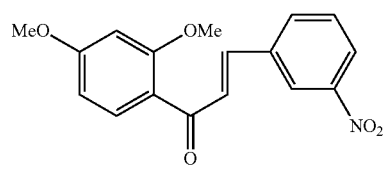
Compound 6
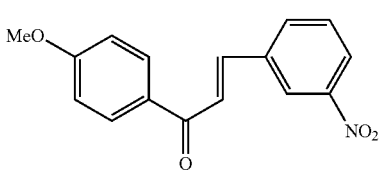
Compound 8
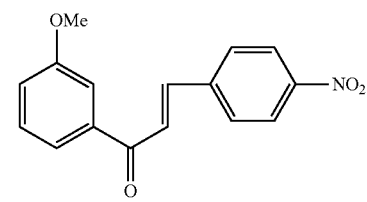
Compound 9
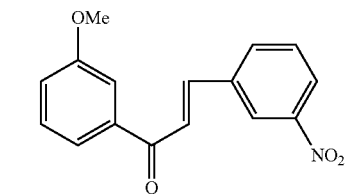
Compound 11
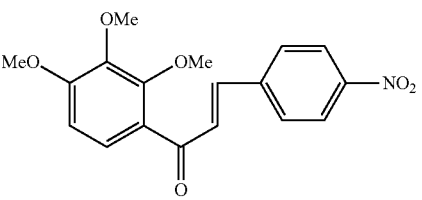
Compound 12
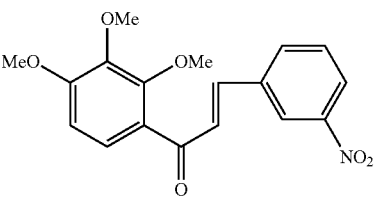
Compound 14
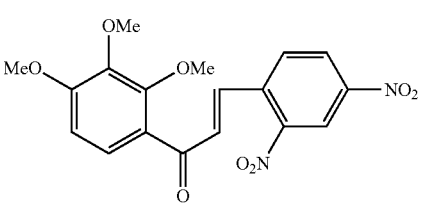
Compound 15
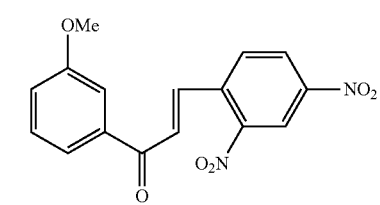
Compound 16
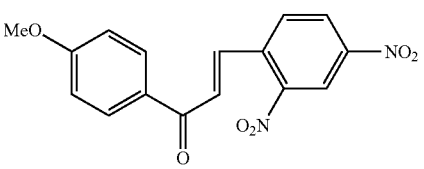

-continued
Compound 27
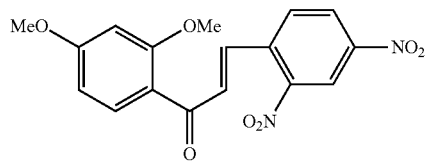
Compound 31
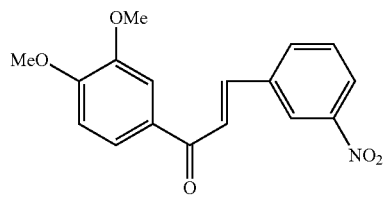
Compound 33
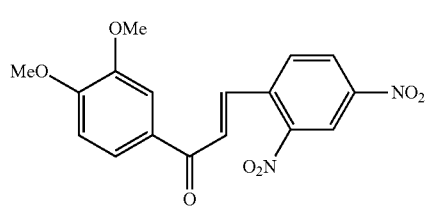
Compound 38
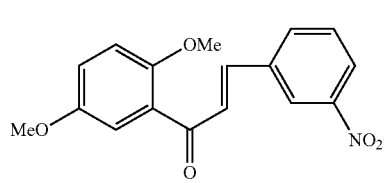
Compound 39
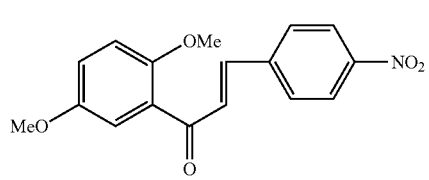
Compound 44
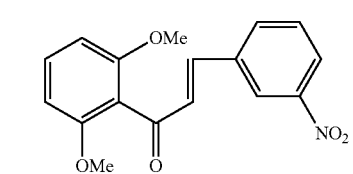
Compound 45
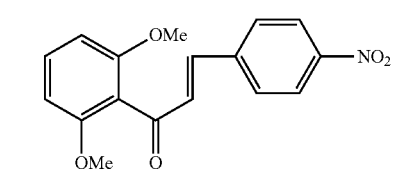
Compound 50
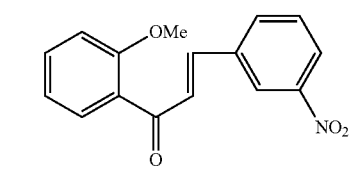
Compound 51
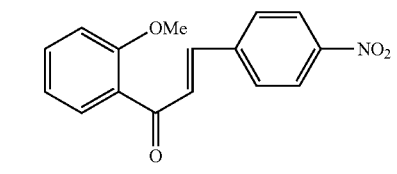
-continued
Compound 52
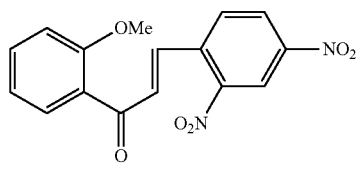
Compound 56
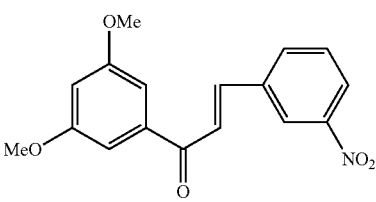
Compound 57
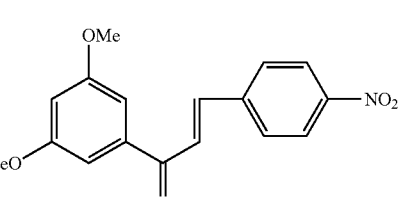
Compound 58
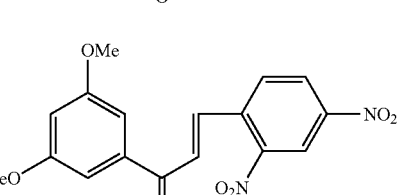
Compound 61
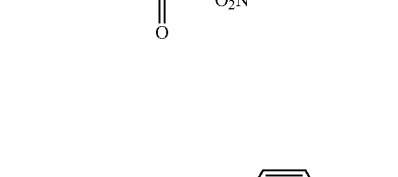
Compound 62
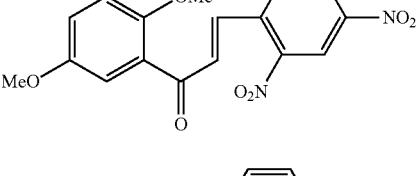
Compound 66
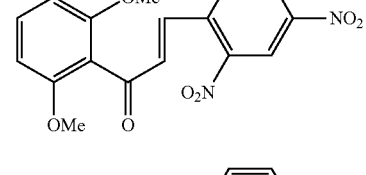
Compound 80
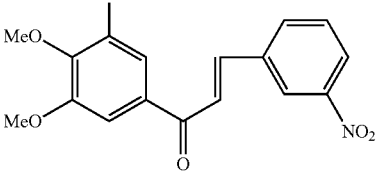

95

-continued

Compound 86: chalcone with 2,4,6-trimethoxyphenyl ketone and 3-nitrophenyl vinyl group Compound 87: chalcone with 2,4,6-trimethoxyphenyl ketone and 4-nitrophenyl vinyl group Compound 93: chalcone with 2,4,6-trimethoxyphenyl ketone and 2,4-dinitrophenyl vinyl group Compound 94: chalcone with 2,4,6-trimethoxyphenyl ketone and 4-cyanophenyl vinyl group Compound 95: chalcone with 3,4,5-trimethoxyphenyl ketone and 4-cyanophenyl vinyl group Compound 96: chalcone with 2,3,4-trimethoxyphenyl ketone and 4-cyanophenyl vinyl group Compound 97: chalcone with 2,4,6-trimethoxyphenyl ketone and 3-cyanophenyl vinyl group Compound 98: chalcone with 3,4,5-trimethoxyphenyl ketone and 3-cyanophenyl vinyl group

96

-continued

Compound 99: chalcone with 2,3,4-trimethoxyphenyl ketone and 3-cyanophenyl vinyl group Compound 100: chalcone with 2,4-dimethoxyphenyl ketone and 4-cyanophenyl vinyl group Compound 101: chalcone with 2,5-dimethoxyphenyl ketone and 4-cyanophenyl vinyl group Compound 102: chalcone with 2,6-dimethoxyphenyl ketone and 4-cyanophenyl vinyl group Compound 103: chalcone with 3,4-dimethoxyphenyl ketone and 4-cyanophenyl vinyl group Compound 104: chalcone with 3,5-dimethoxyphenyl ketone and 4-cyanophenyl vinyl group Compound 105: chalcone with phenyl ketone and 4-cyanophenyl vinyl group Compound 106: chalcone with 2-methoxyphenyl ketone and 4-cyanophenyl vinyl group

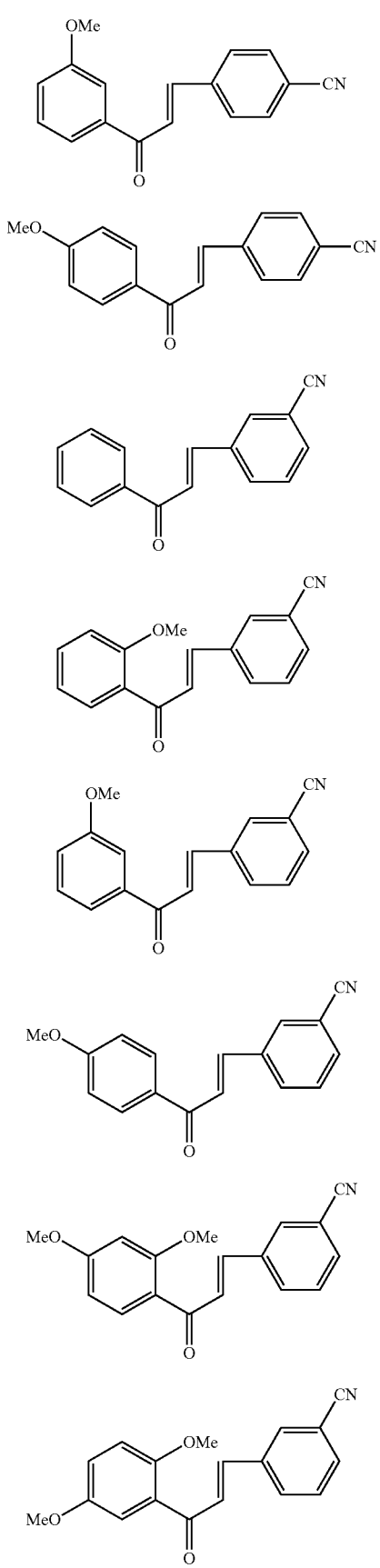
Compound 107
Compound 108
Compound 109
Compound 110
Compound 111
Compound 112
Compound 113
Compound 114
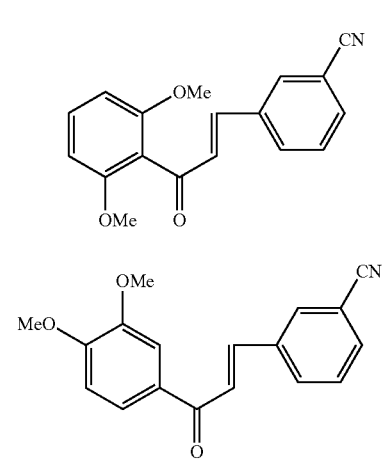
Compound 115
Compound 116
Compound 117
9. The method of claim 2, wherein the compound is
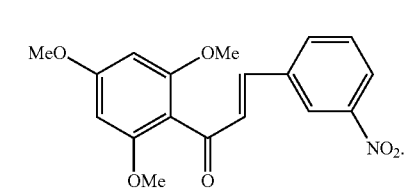
(compound 86)
10. The method of claim 3, wherein the compound is one of the following:
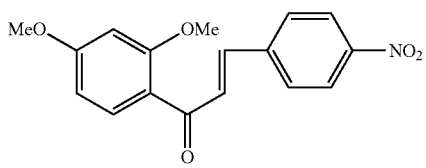
Compound 2
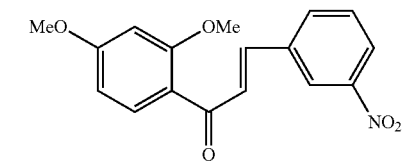
Compound 3
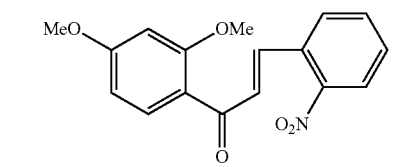
Compound 4

-continued
Compound 5
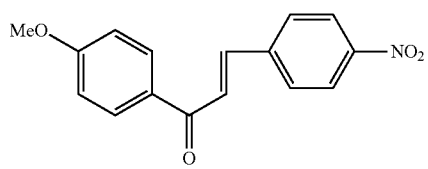
Compound 6
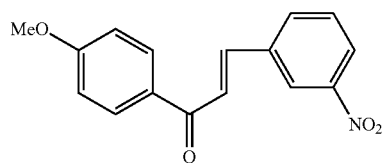
Compound 7
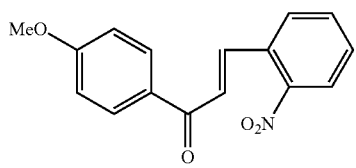
Compound 8
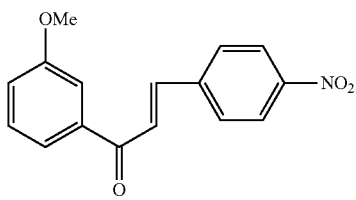
Compound 9
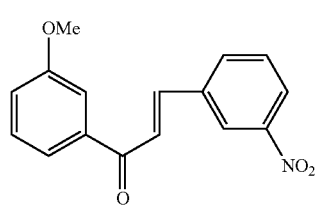
Compound 10
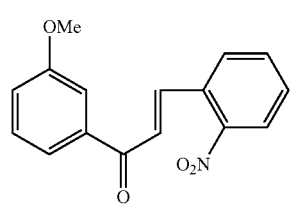
Compound 11
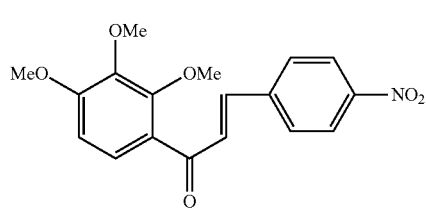
Compound 12
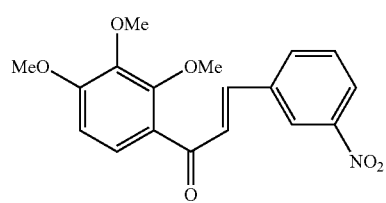
-continued
Compound 13
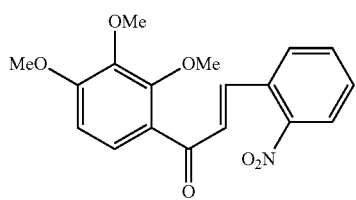
Compound 14
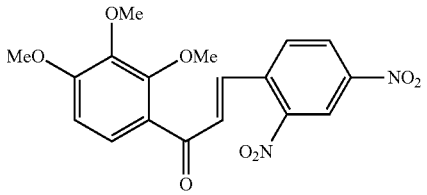
Compound 15
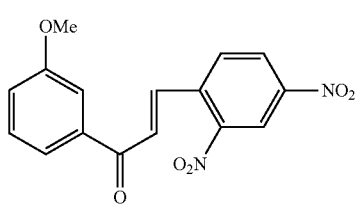
Compound 16
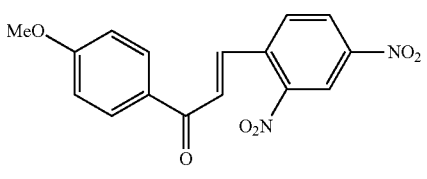
Compound 17
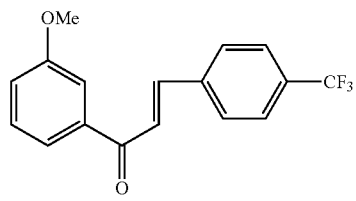
Compound 18
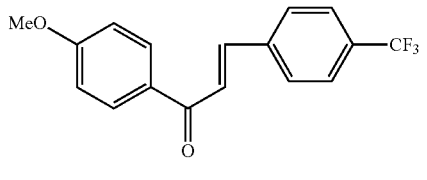
Compound 19
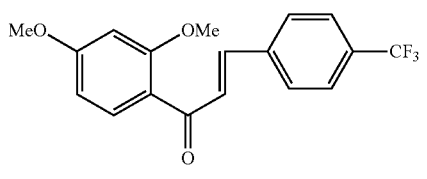
Compound 20
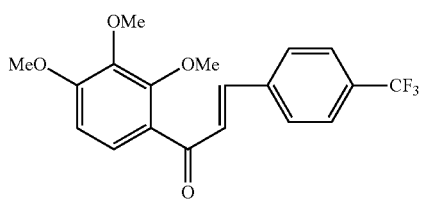

-continued
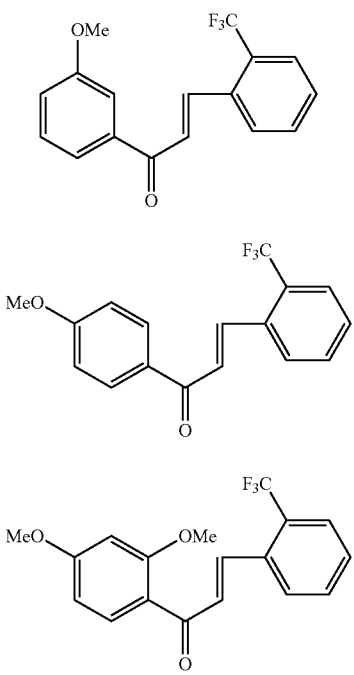
Compound 21
Compound 22
Compound 23
Compound 24
Compound 25
Compound 26
Compound 27
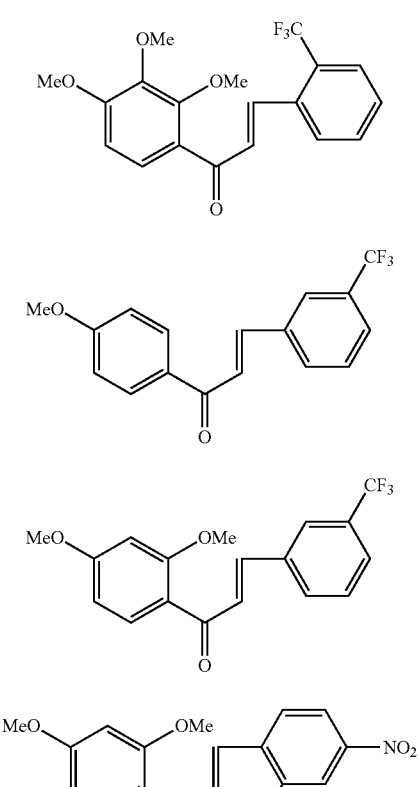
Compound 28
Compound 29
Compound 30
Compound 31
Compound 32
Compound 33
Compound 34
Compound 35

| | |
|---|---|
| Compound 36 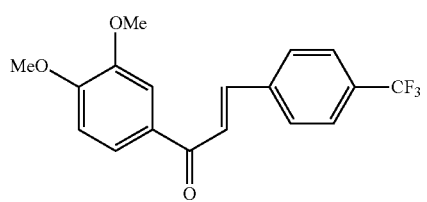 | Compound 45 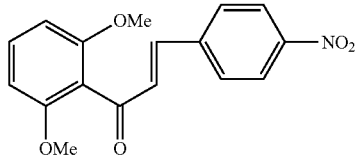 |
| Compound 37 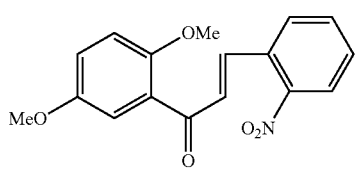 | Compound 46 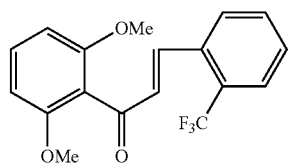 |
| Compound 38 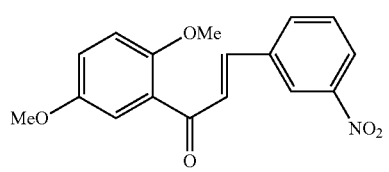 | Compound 47 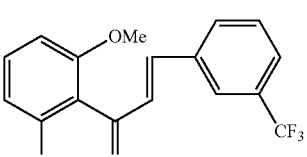 |
| Compound 39 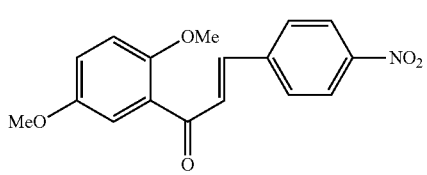 | Compound 48 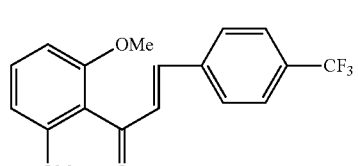 |
| Compound 40 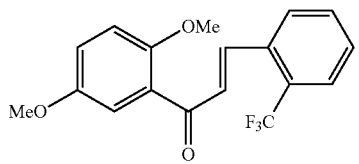 | Compound 49 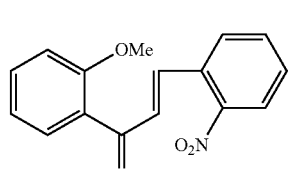 |
| Compound 41 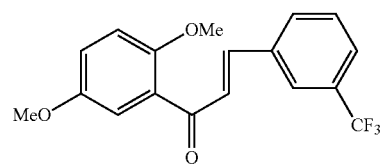 | Compound 50 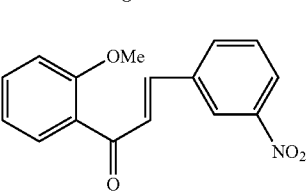 |
| Compound 42 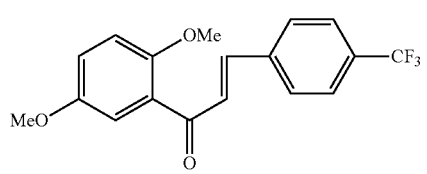 | Compound 51 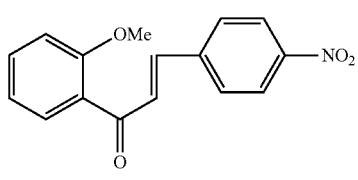 |
| Compound 43 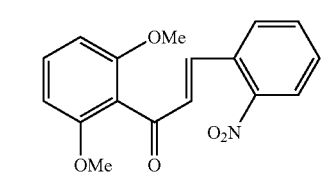 | Compound 52 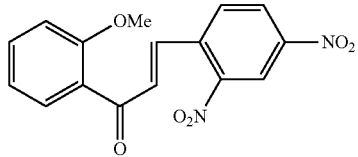 |
| Compound 44 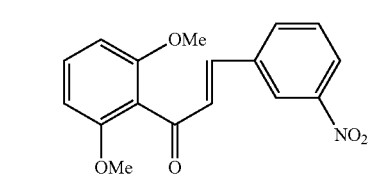 | Compound 53 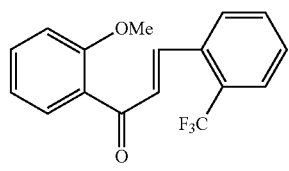 |

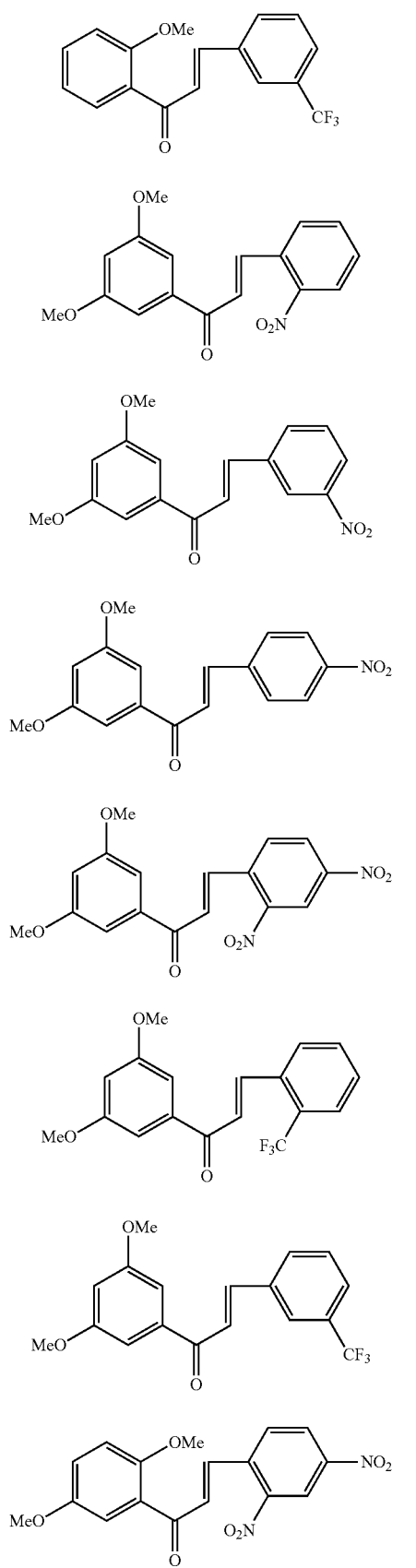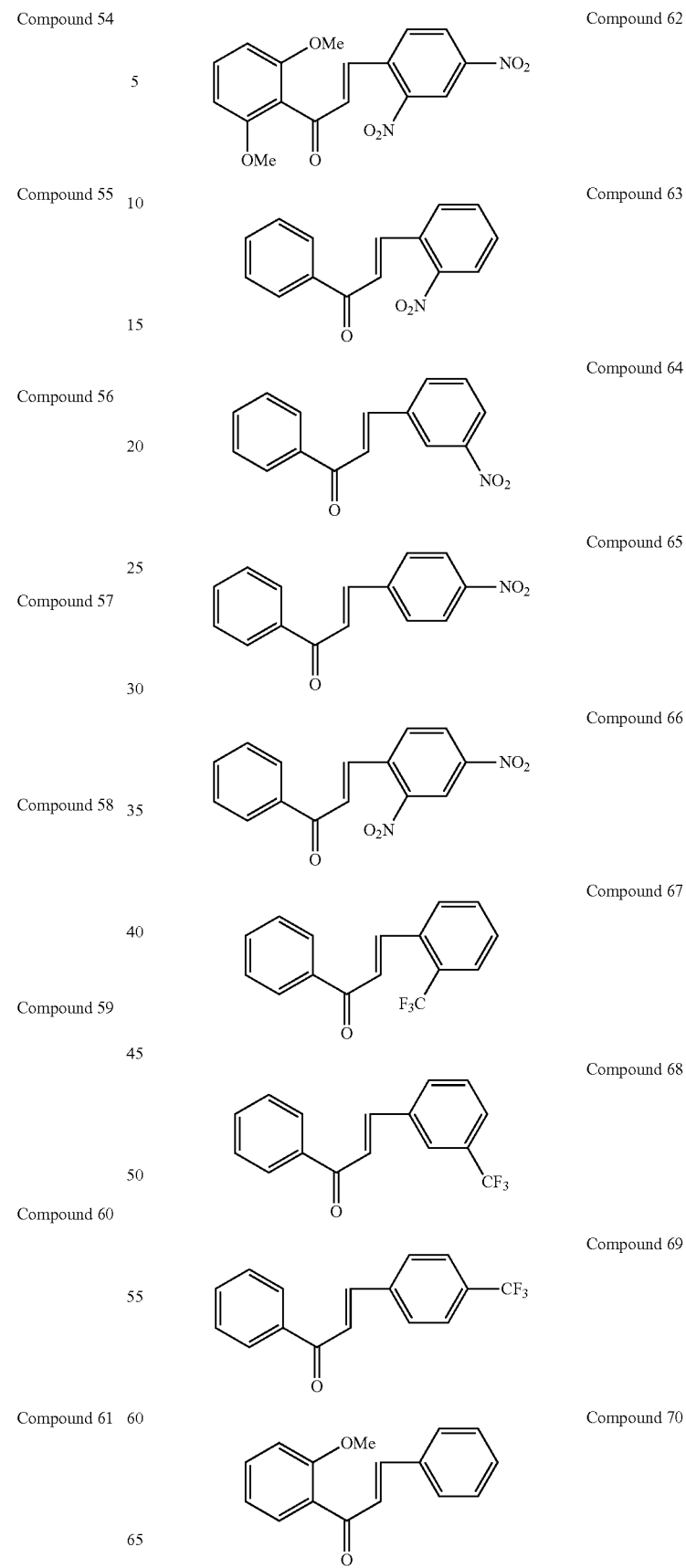

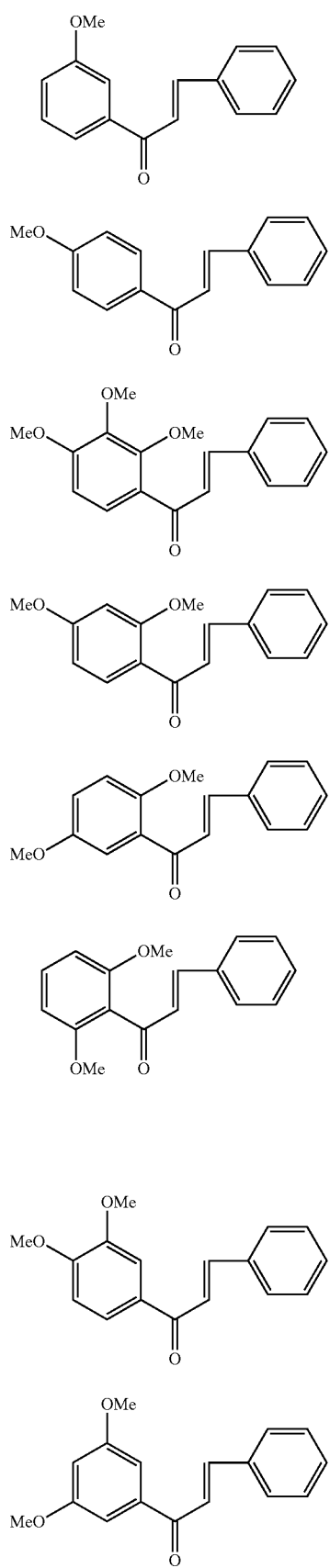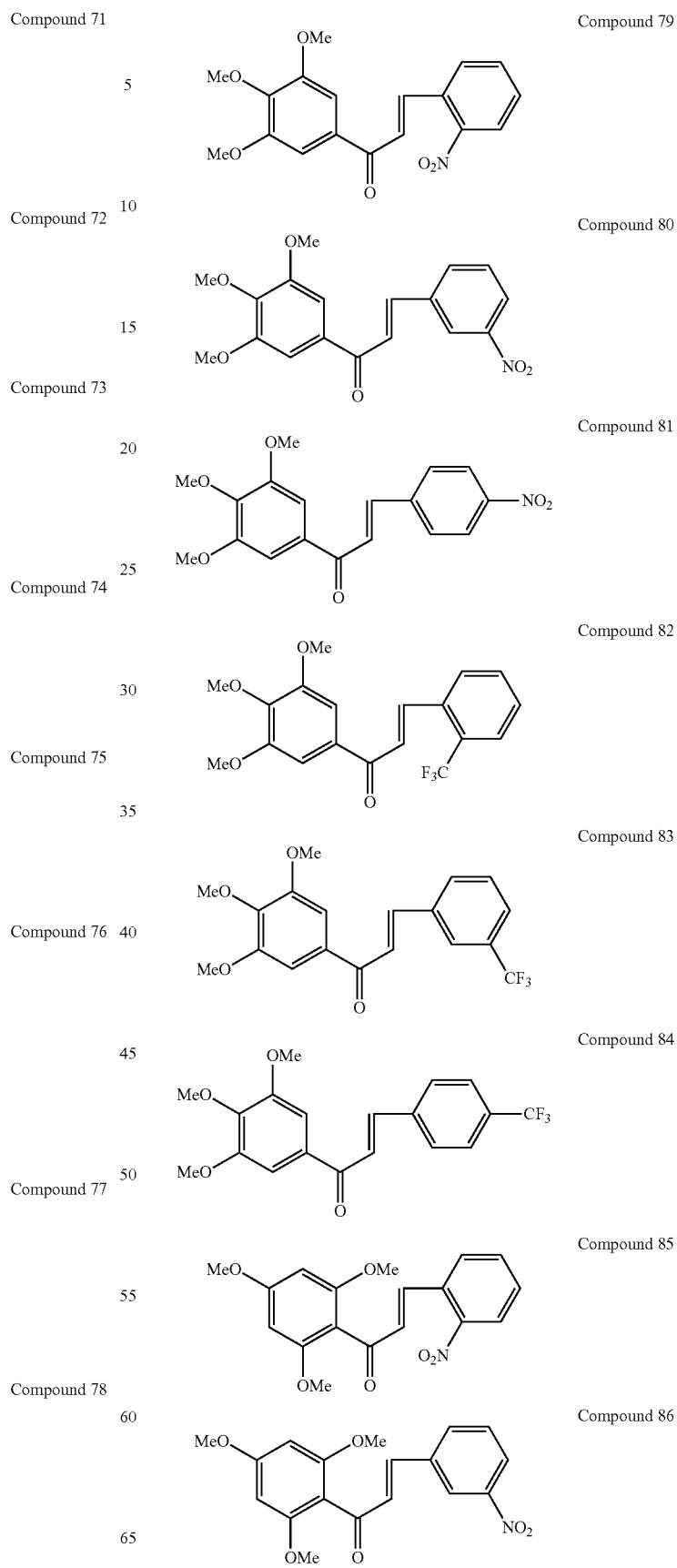

Compound 87
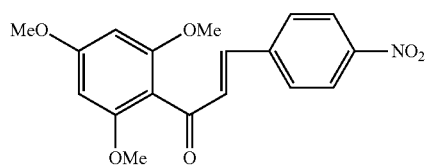
Compound 88
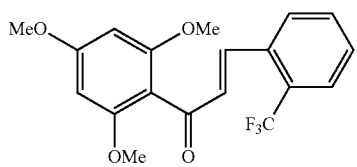
Compound 89
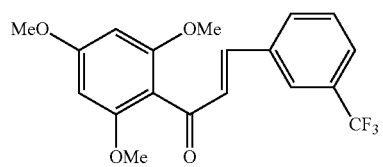
Compound 90
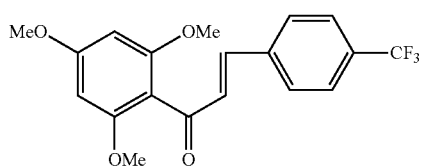
Compound 91
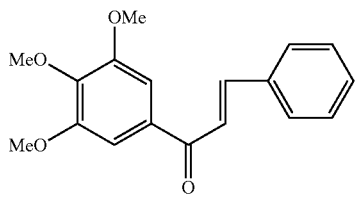
Compound 92
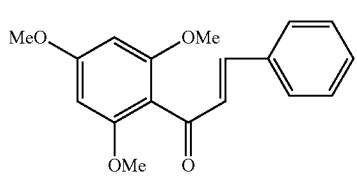
Compound 93
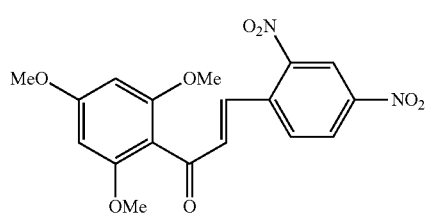
Compound 94
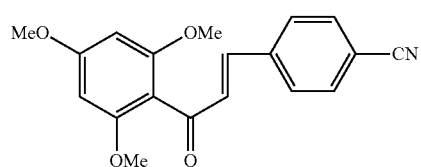
Compound 95
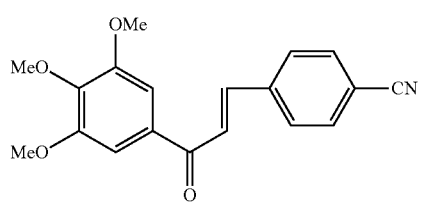
Compound 96
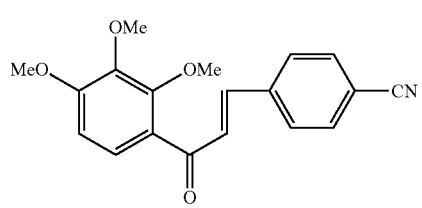
Compound 97
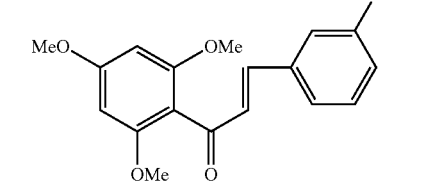
Compound 98
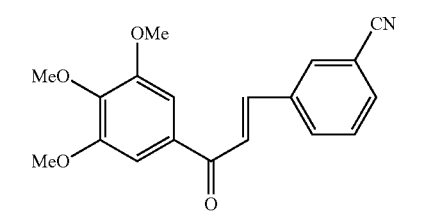
Compound 99
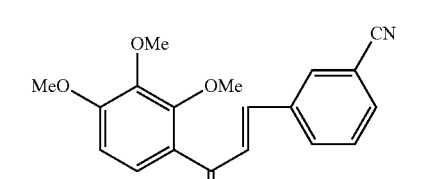
Compound 100
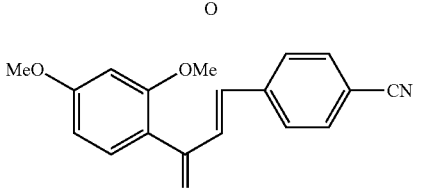
Compound 101
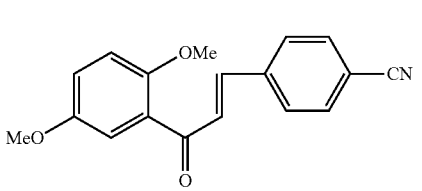
Compound 102
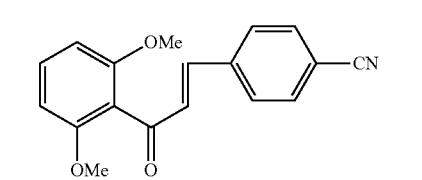

Compound 103
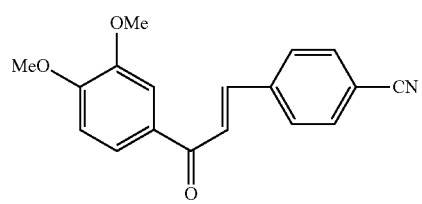
Compound 104
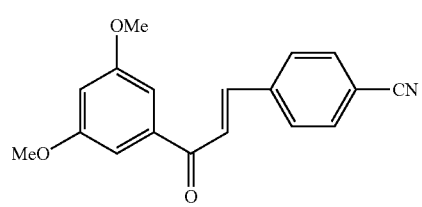
Compound 105
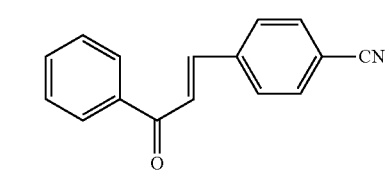
Compound 106
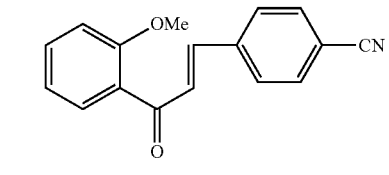
Compound 107
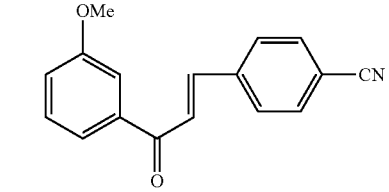
Compound 108
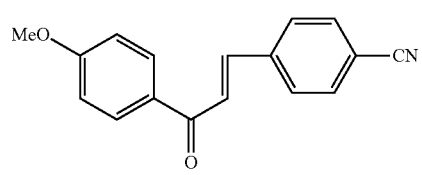
Compound 109
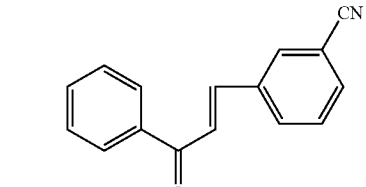
Compound 110
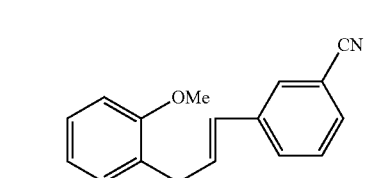
Compound 111
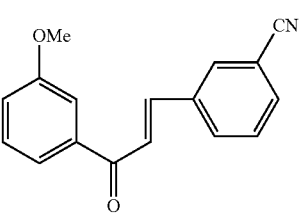
Compound 112
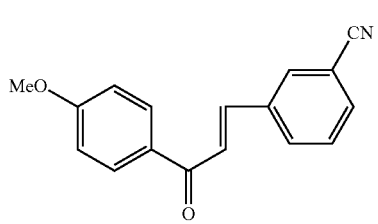
Compound 113
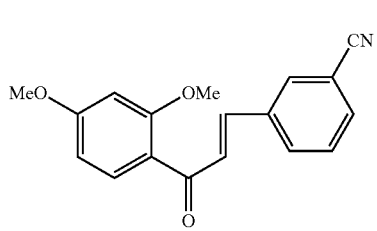
Compound 114
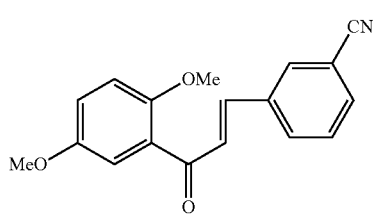
Compound 115
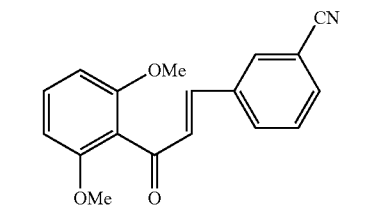
Compound 116
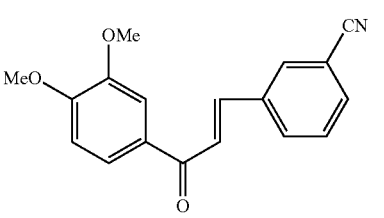 or
Compound 117
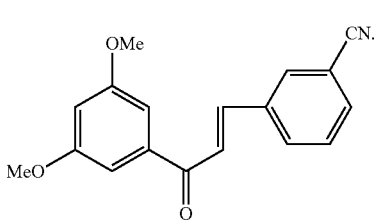
11. The method of claim 3, wherein the compound is of one of the following:

Compound 2
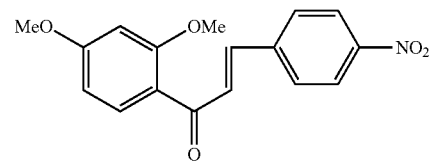
Compound 3
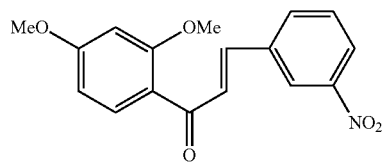
Compound 5
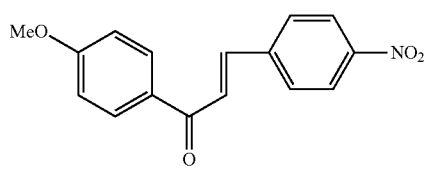
Compound 6
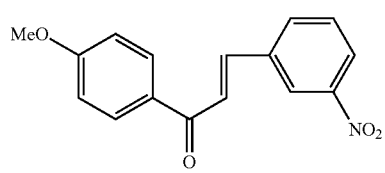
Compound 8
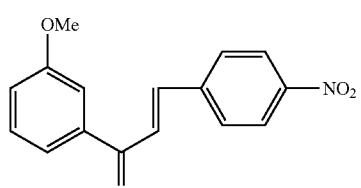
Compound 9
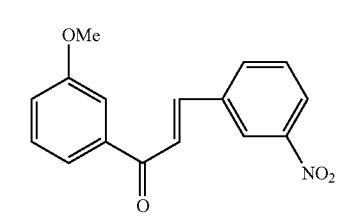
Compound 11
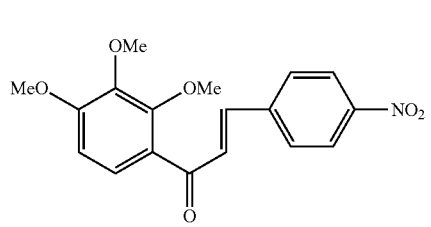
Compound 12
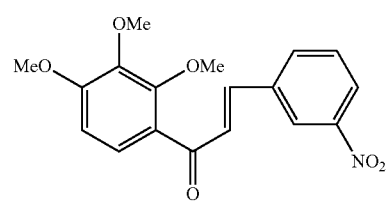
-continued
Compound 14
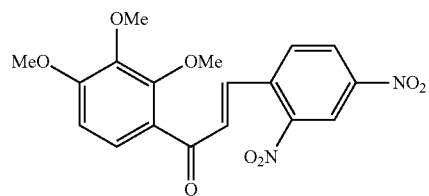
Compound 15
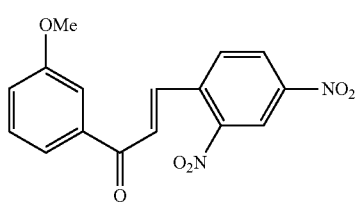
Compound 16
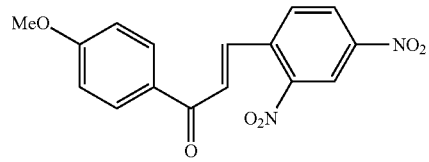
Compound 27
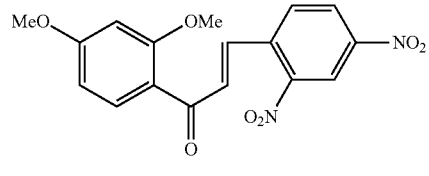
Compound 31
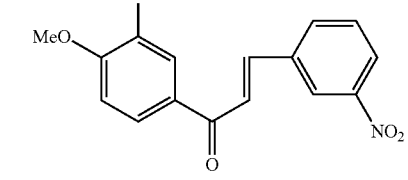
Compound 33
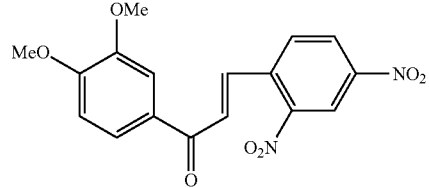
Compound 38
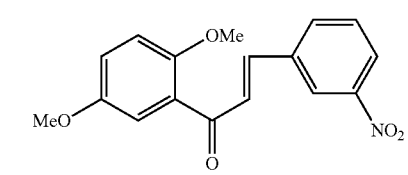
Compound 39
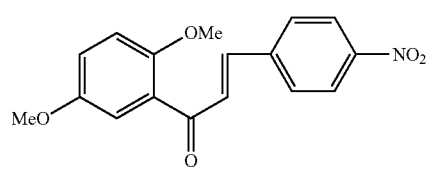

-continued
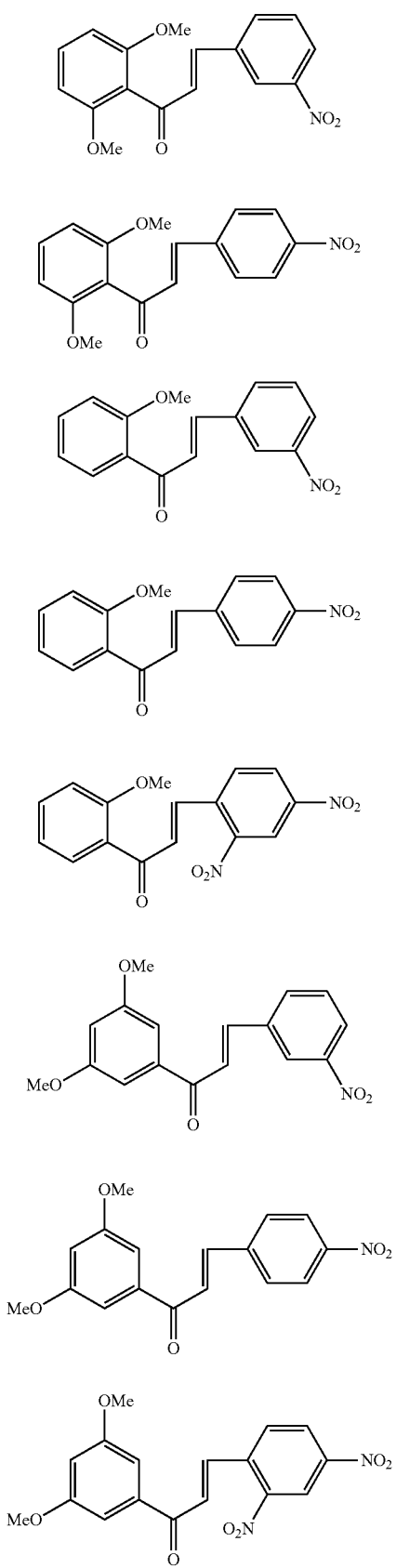
Compound 44
Compound 45
Compound 50
Compound 51
Compound 52
Compound 56
Compound 57
Compound 58
-continued
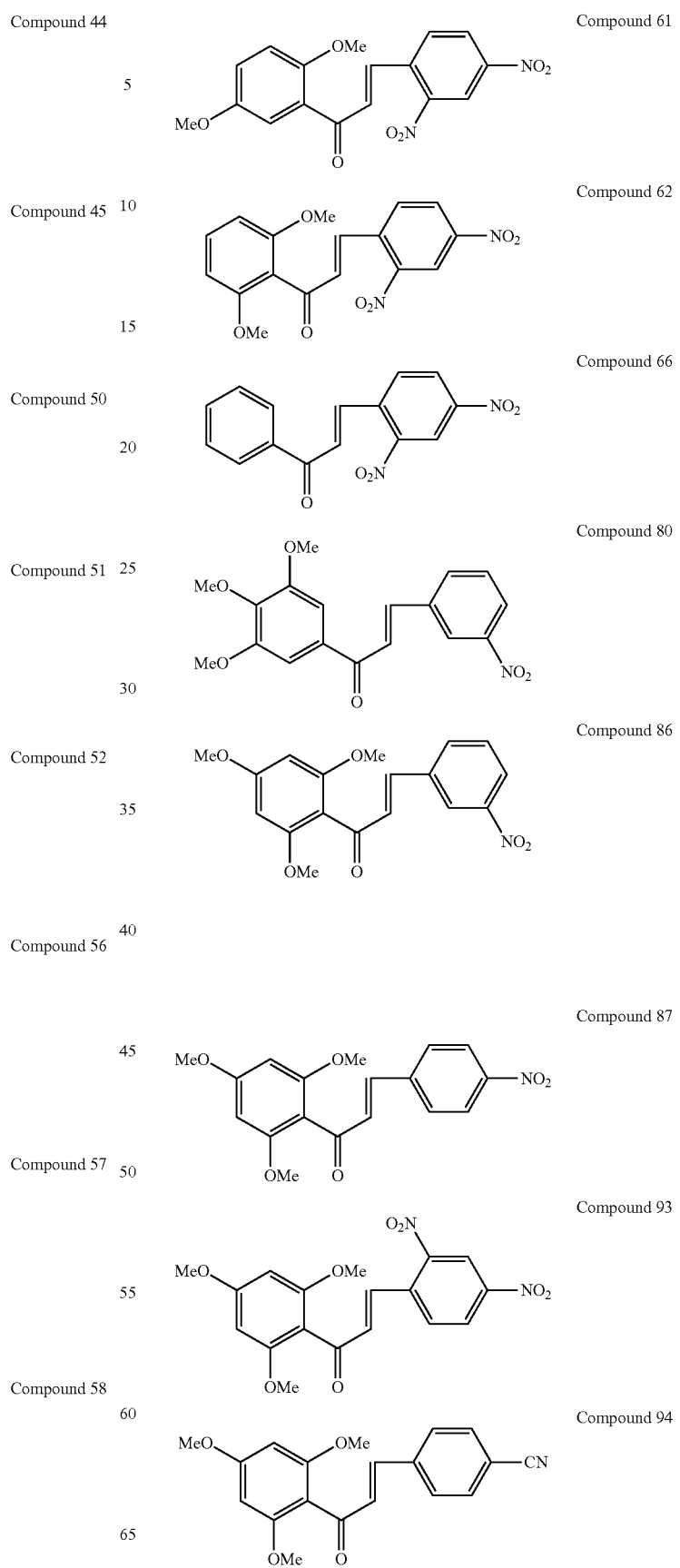
Compound 61
Compound 62
Compound 66
Compound 80
Compound 86
Compound 87
Compound 93
Compound 94

Compound 95
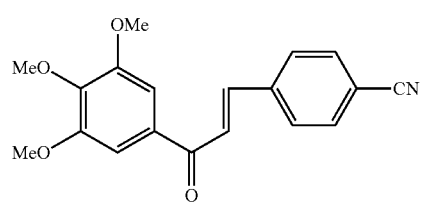
Compound 96
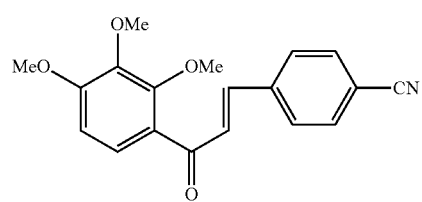
Compound 97
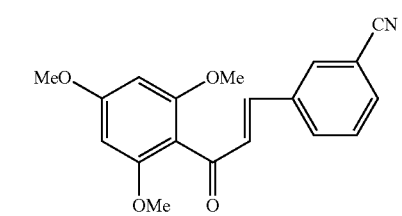
Compound 98
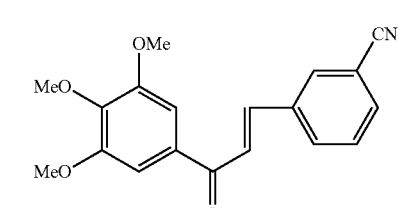
Compound 99
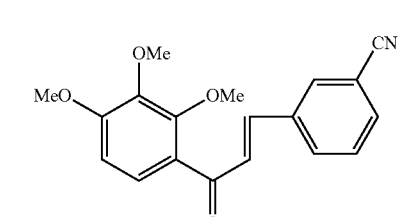
Compound 100
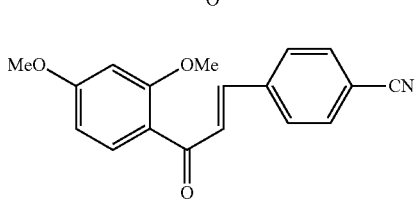
Compound 101
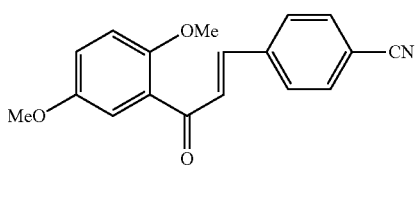
Compound 102
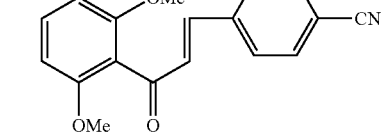
Compound 103
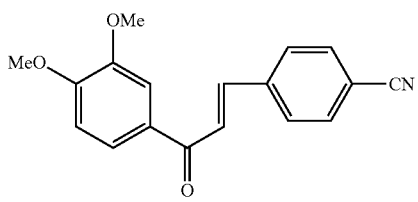
Compound 104
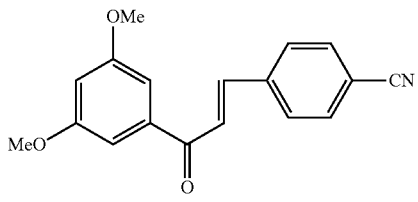
Compound 105
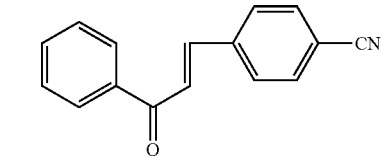
Compound 106
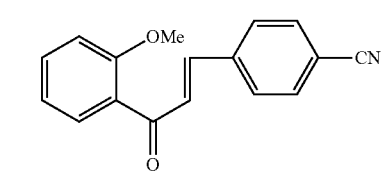
Compound 107
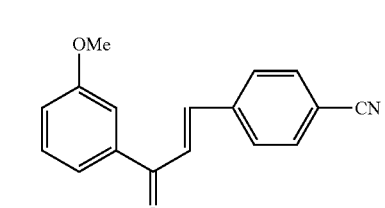
Compound 108
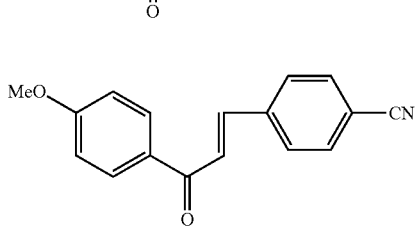
Compound 109
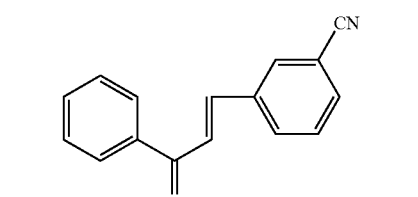
Compound 110
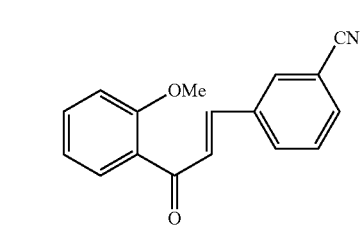

12. The method of claim 3, wherein the compound is (compound 86)

13. A method of treating prostate cancer in a human subject comprising administering to the subject an effective amount of a compound Formula I:

$$\text{(I)}$$

wherein $R_1$ to $R_5$ are the same or different and are each selected from H and $C_1$-$C_6$ alkoxy;
wherein $X_1$ to $X_5$ are the same or different and are each selected from H and the electron withdrawing groups of $NO_2$, CN, and $CF_3$; and
wherein bond "a" can be in either the E or Z form;
with the provsio that $R_1$ to $R_5$ and $X_1$ to $X_5$ cannot all be H simultaneously;
or a pharmaceutically acceptable salt, solvate, or stereoisomer thereof.

14. The method of claim 13, wherein the compound is of one of the following:

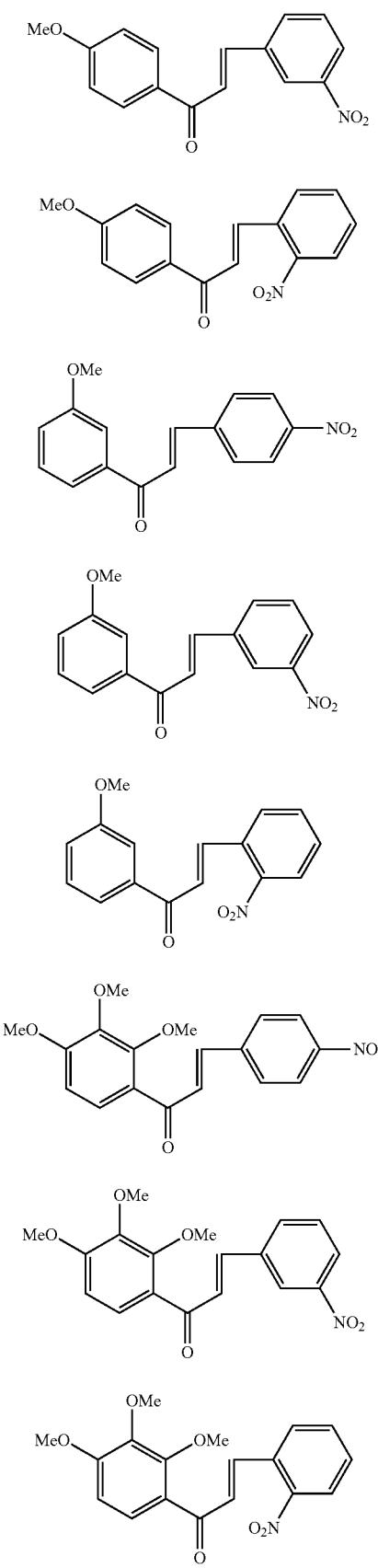
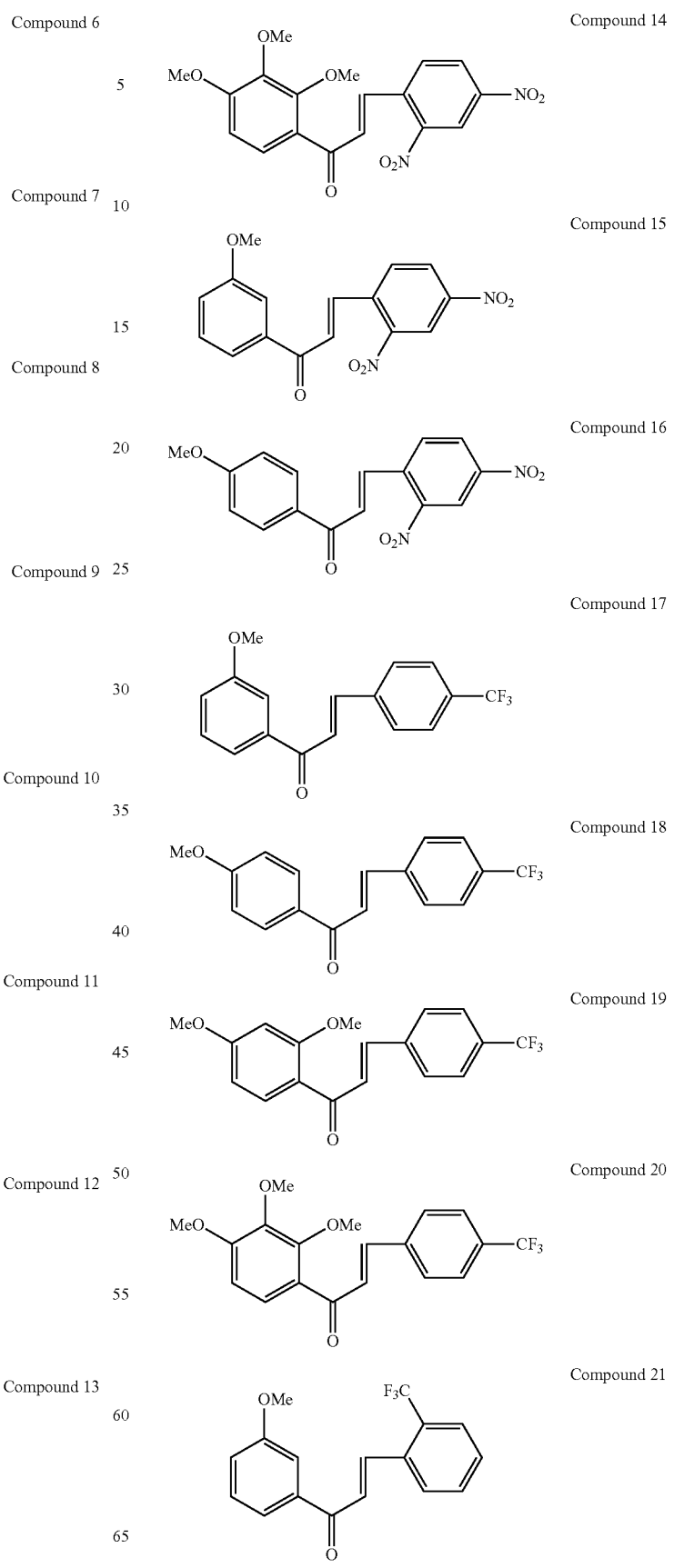

-continued
Compound 22
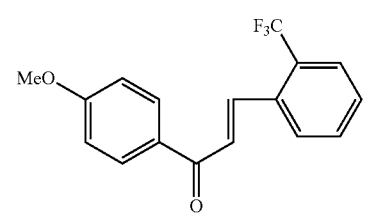
Compound 23
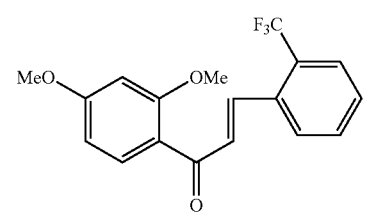
Compound 24
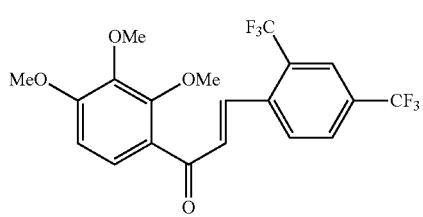
Compound 25
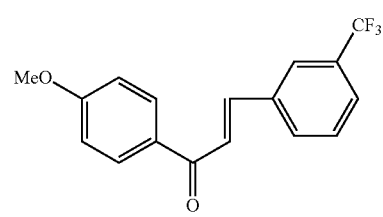
Compound 26
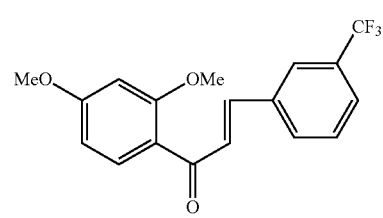
Compound 27
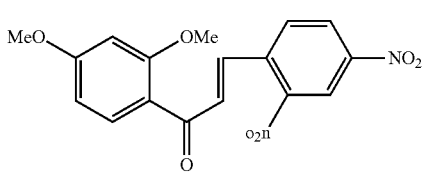
Compound 28
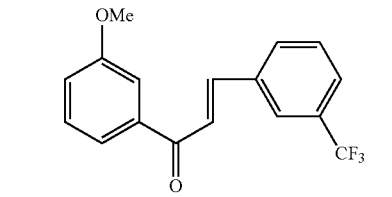
Compound 29
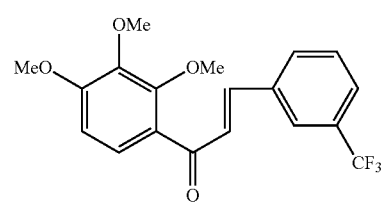
-continued
Compound 30
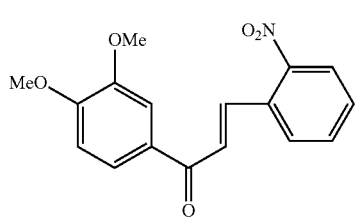
Compound 31
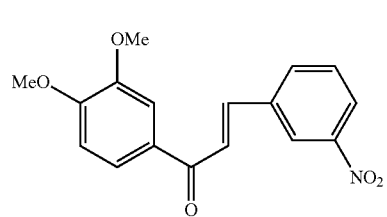
Compound 32
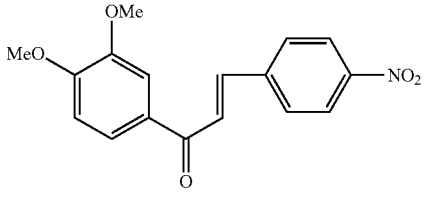
Compound 33
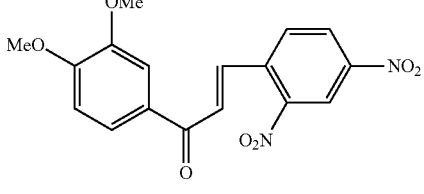
Compound 34
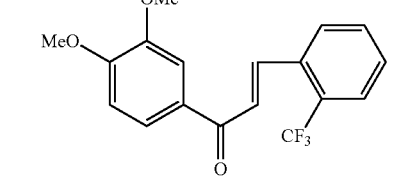
Compound 35
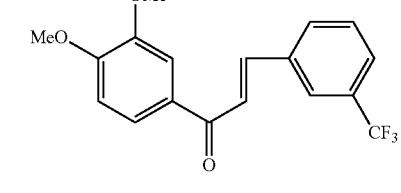
Compound 36
Compound 37
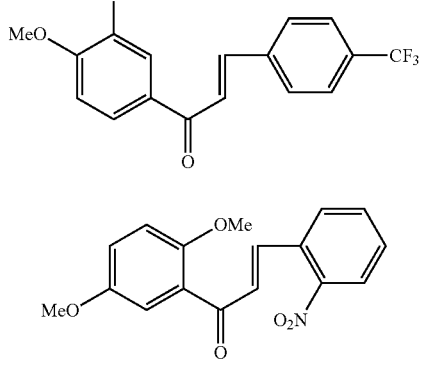

Compound 38
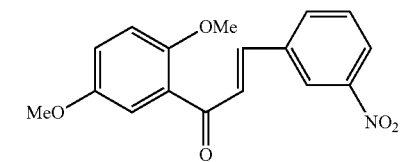
Compound 39
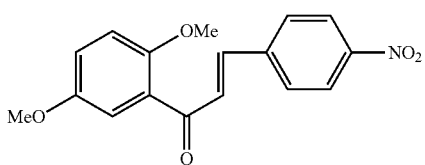
Compound 40
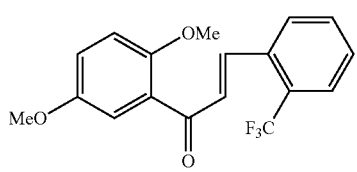
Compound 41
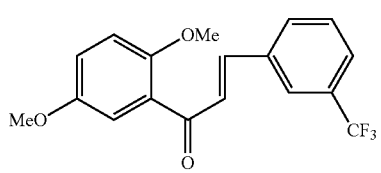
Compound 42
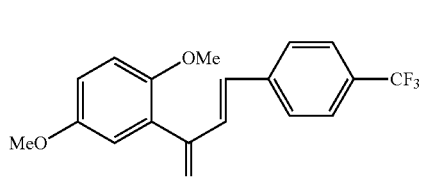
Compound 43
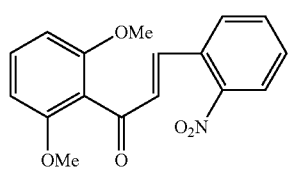
Compound 44
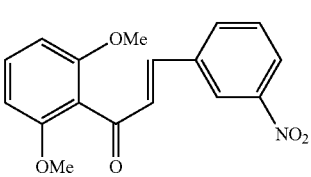
Compound 45
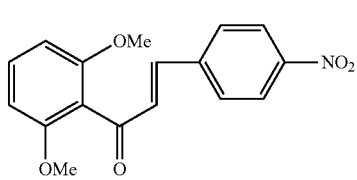
Compound 46
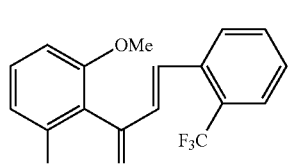
Compound 47
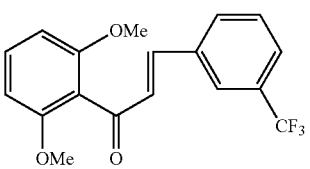
Compound 48
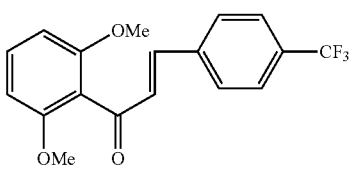
Compound 49
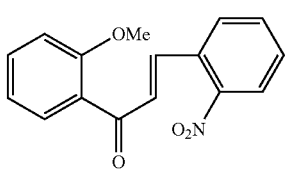
Compound 50
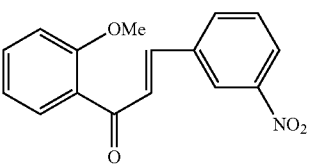
Compound 51
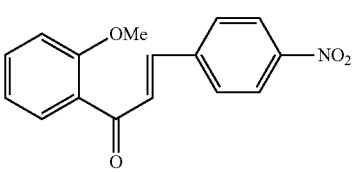
Compound 52
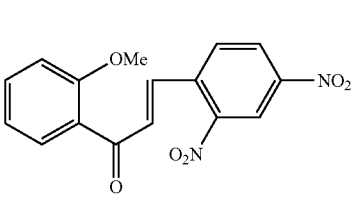
Compound 53
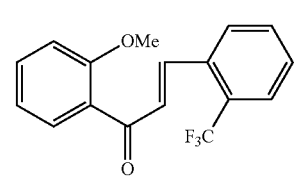
Compound 54
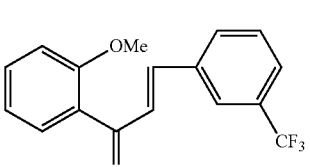
Compound 55
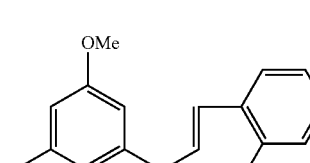
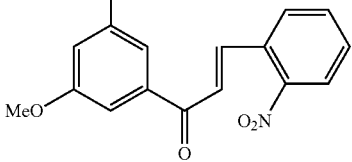

Compound 56
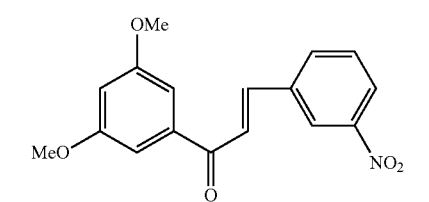
Compound 57
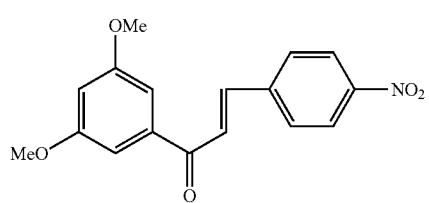
Compound 58
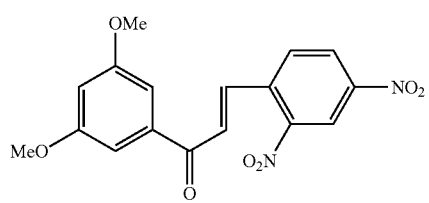
Compound 59
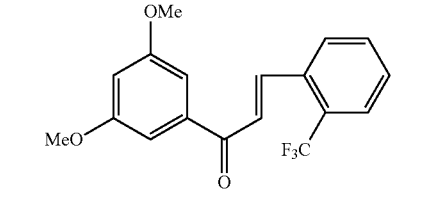
Compound 60
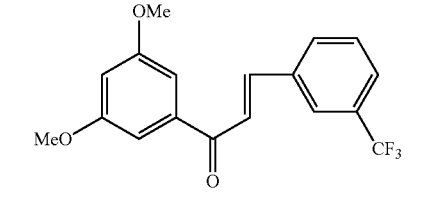
Compound 61
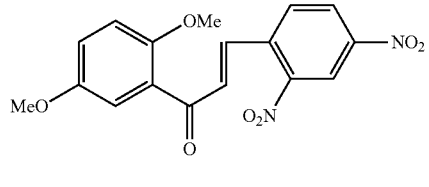
Compound 62
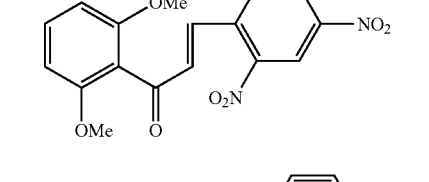
Compound 63
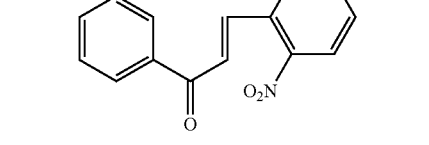
Compound 64
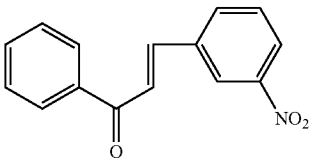
Compound 65
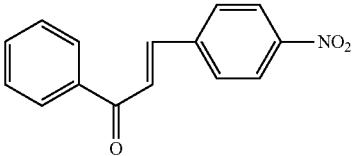
Compound 66
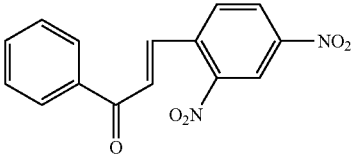
Compound 67
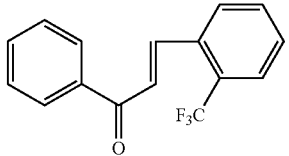
Compound 68
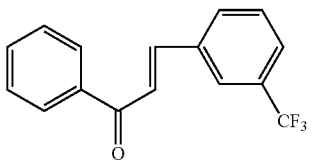
Compound 69
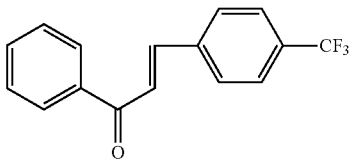
Compound 70
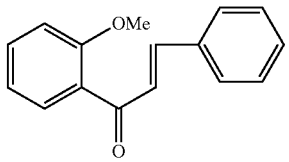
Compound 71
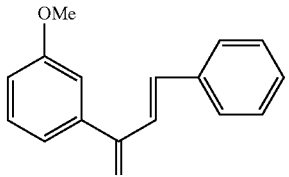
Compound 72
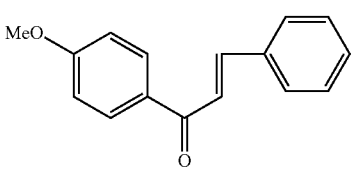

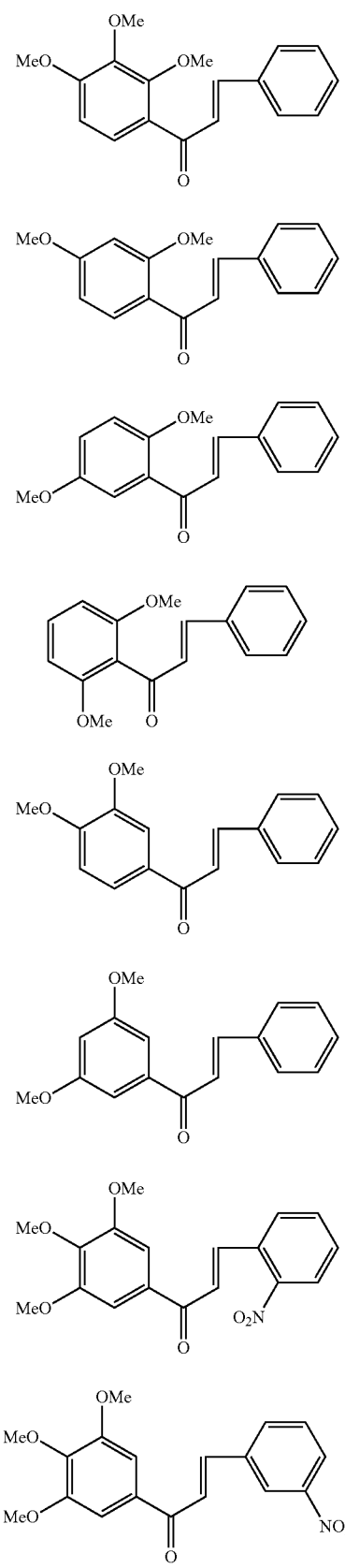
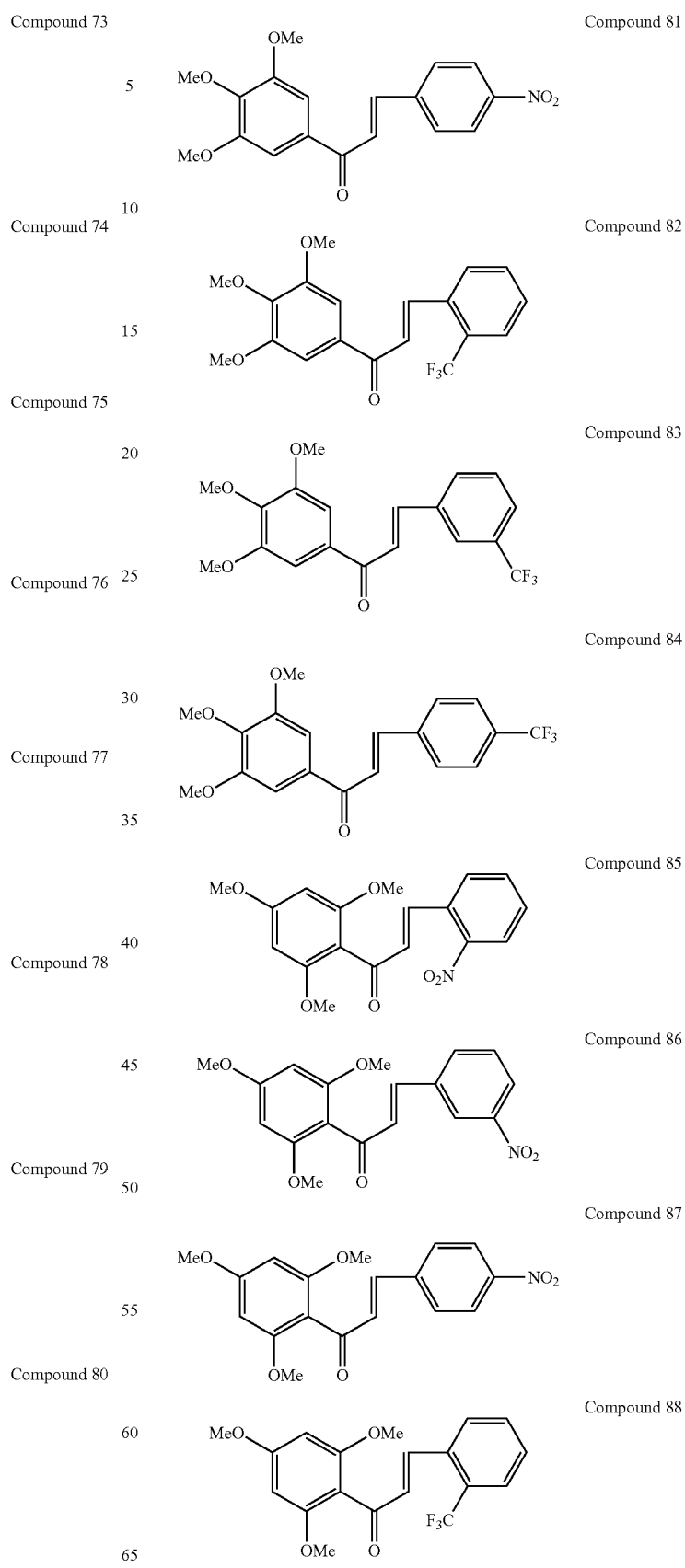

Compound 89
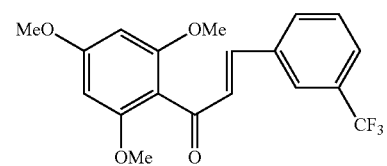
Compound 90
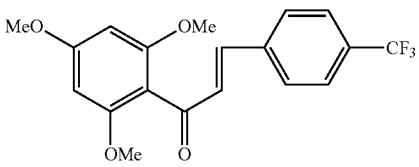
Compound 91
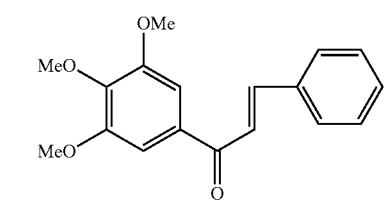
Compound 92
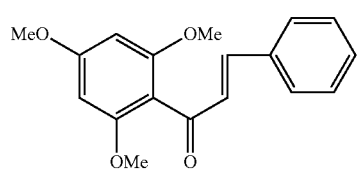
Compound 93
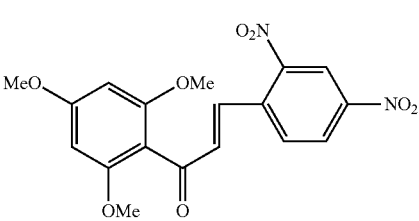
Compound 94
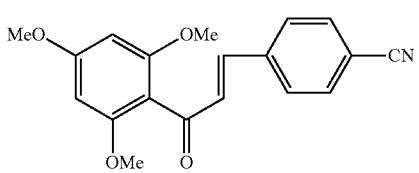
Compound 95
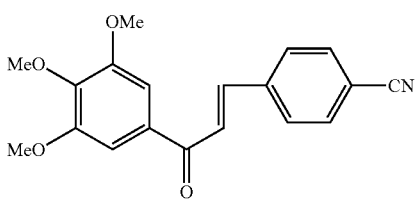
Compound 96
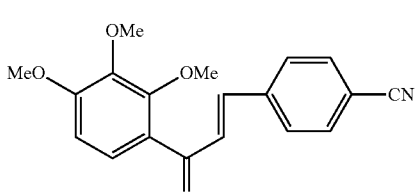
Compound 97
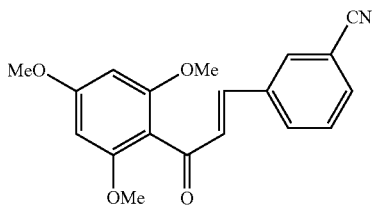
Compound 98
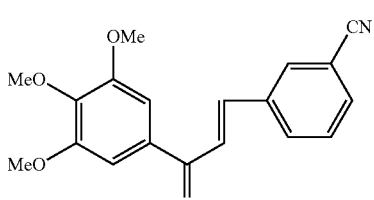
Compound 99
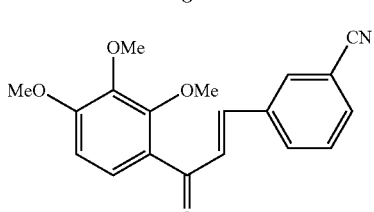
Compound 100
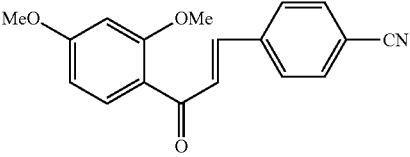
Compound 101
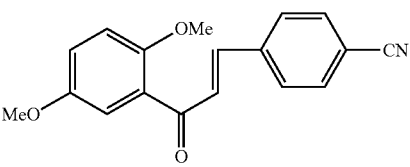
Compound 102
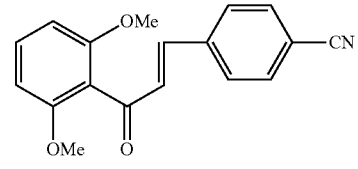
Compound 103
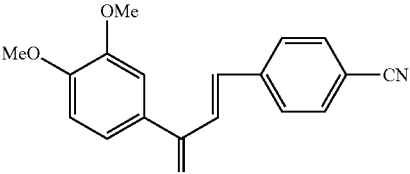
Compound 104
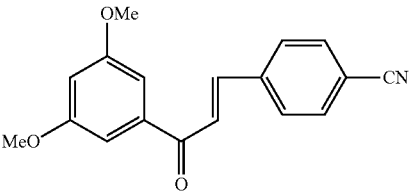

Compound 105
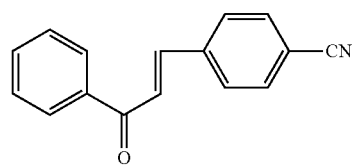
Compound 106
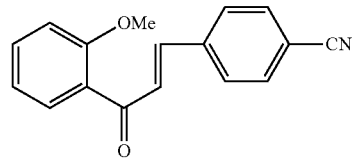
Compound 107
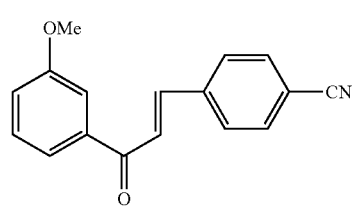
Compound 108
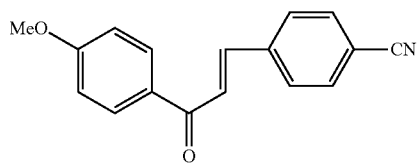
Compound 109
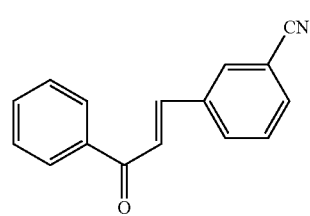
Compound 110
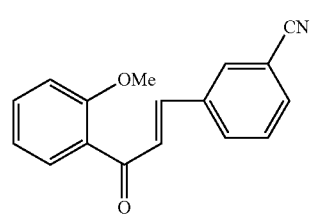
Compound 111
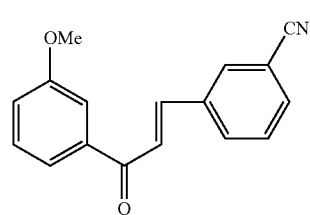
Compound 112
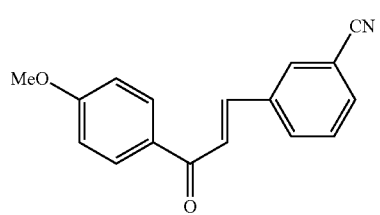
Compound 113
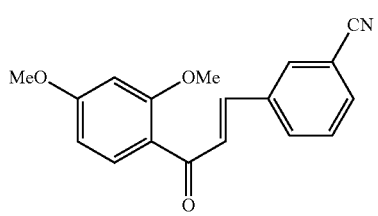
Compound 114
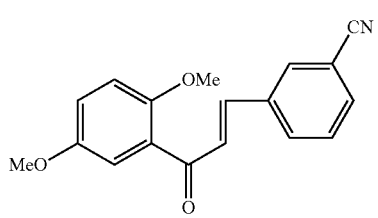
Compound 115
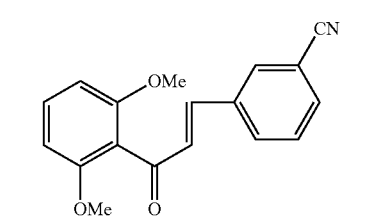
Compound 116 or
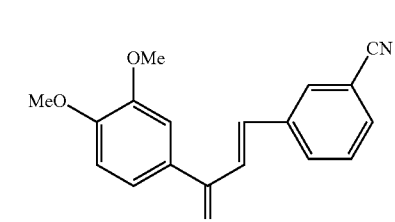
Compound 117
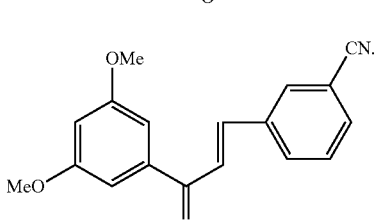
15. The method of claim 13, wherein the compound is of one of the following:
Compound 2
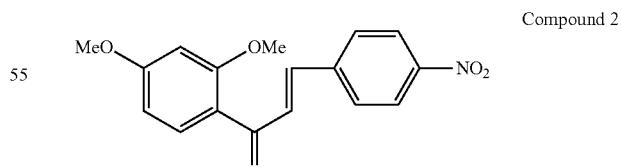
Compound 3
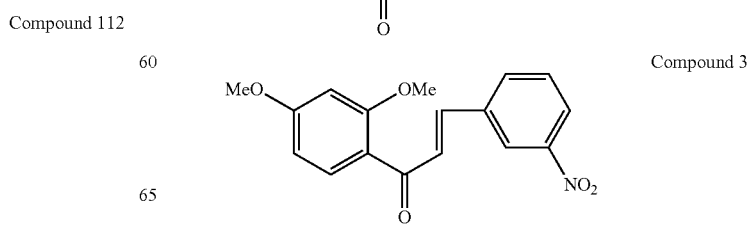

-continued
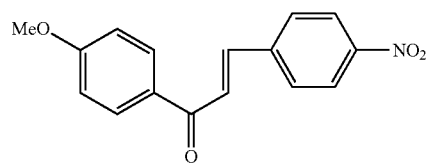
Compound 5
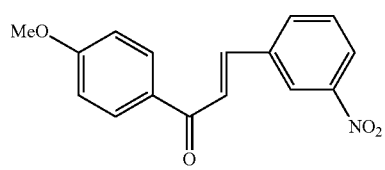
Compound 6
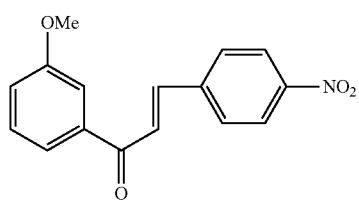
Compound 8
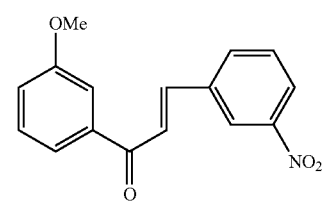
Compound 9
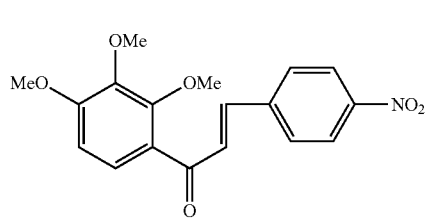
Compound 11
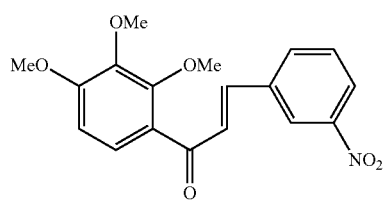
Compound 12
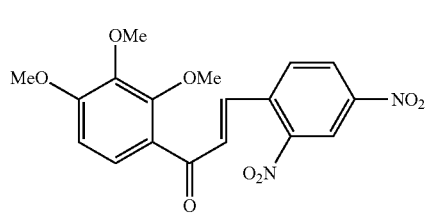
Compound 14
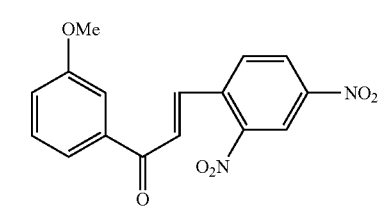
Compound 15
-continued
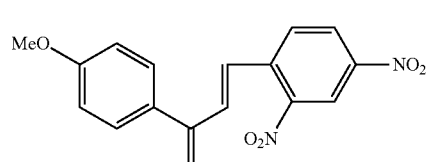
Compound 16
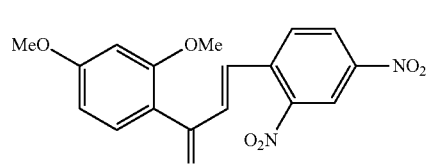
Compound 27
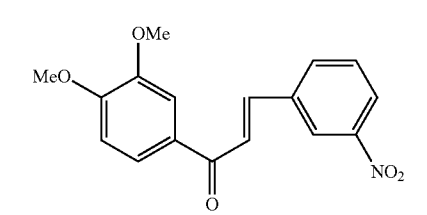
Compound 31
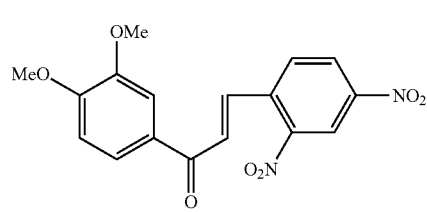
Compound 33
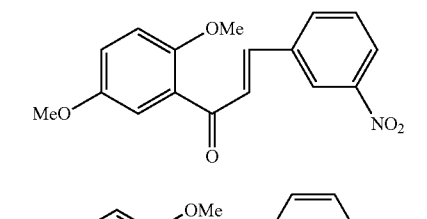
Compound 38
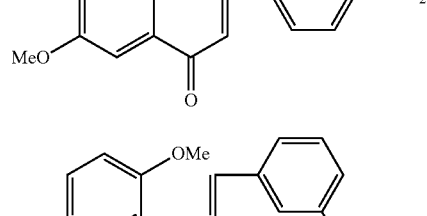
Compound 39
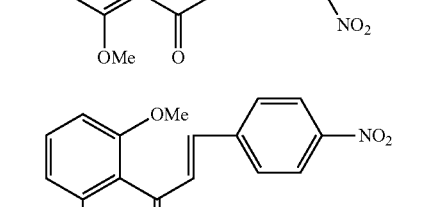
Compound 44
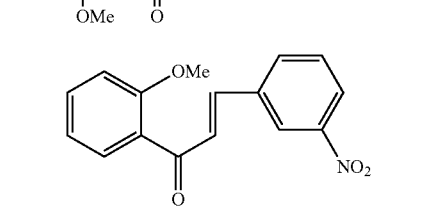
Compound 45
Compound 50

Compound 51
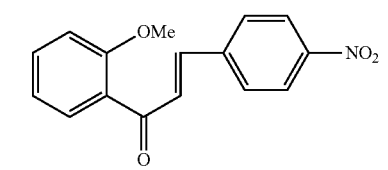
Compound 52
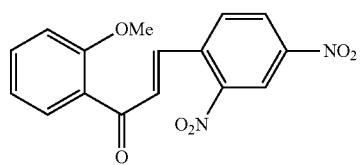
Compound 56
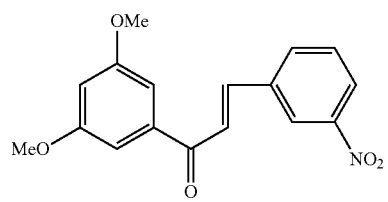
Compound 57
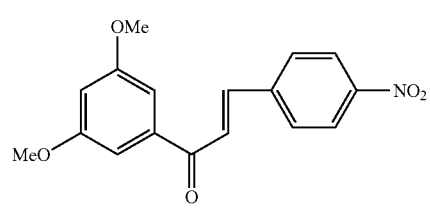
Compound 58
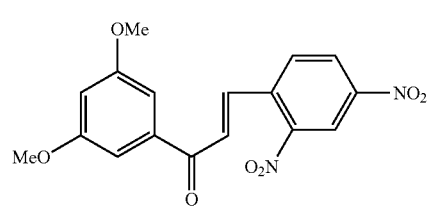
Compound 61
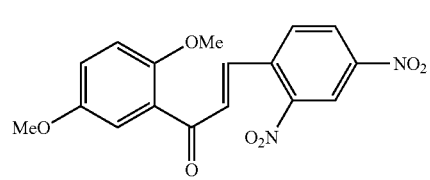
Compound 62
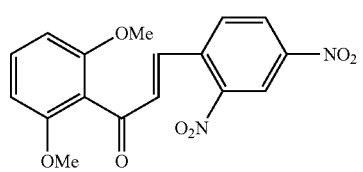
Compound 66
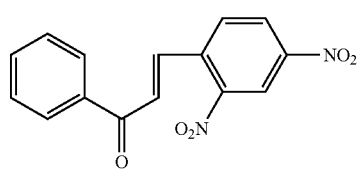
Compound 80
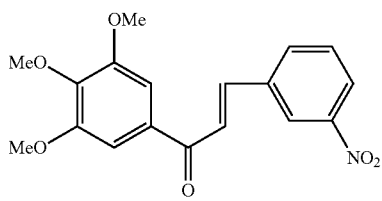
Compound 86
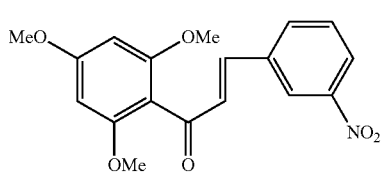
Compound 87
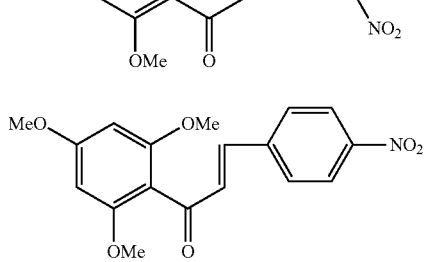
Compound 93
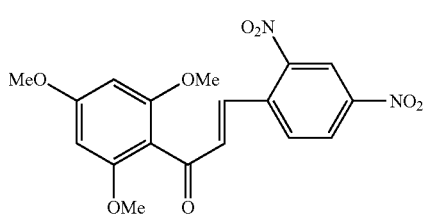
Compound 94
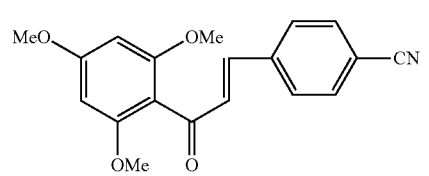
Compound 95
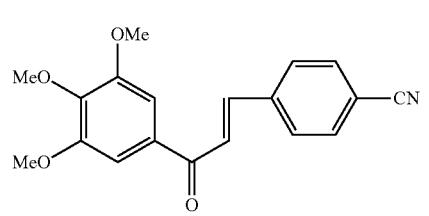
Compound 96
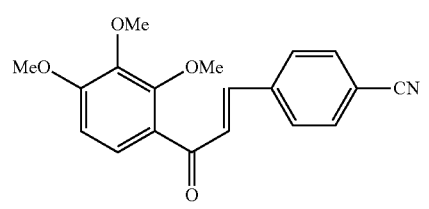
Compound 97
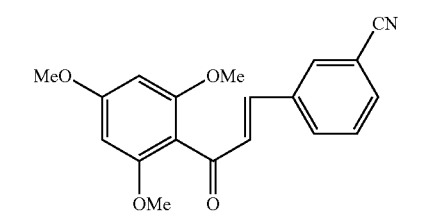

Compound 98
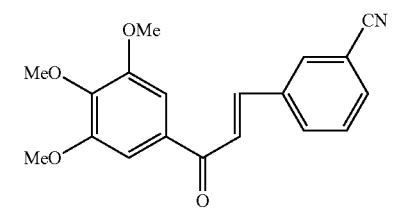
Compound 99
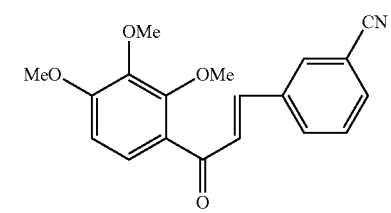
Compound 100
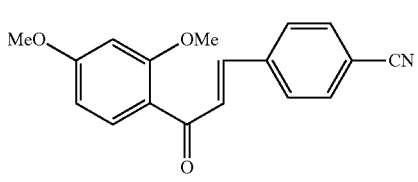
Compound 101
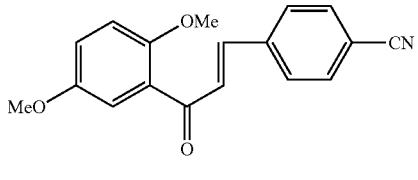
Compound 102
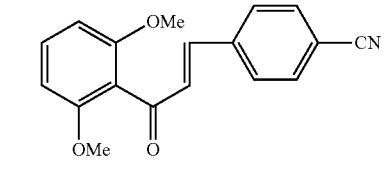
Compound 103
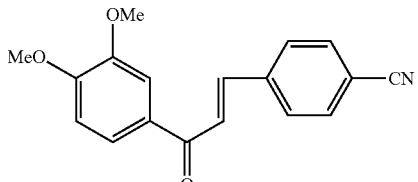
Compound 104
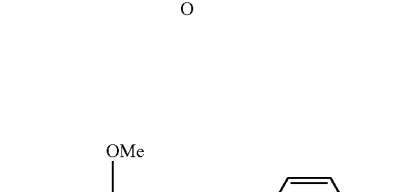
Compound 105
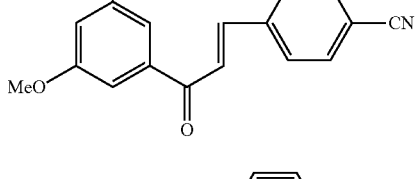
Compound 106
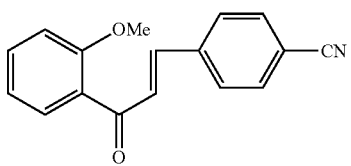
Compound 107
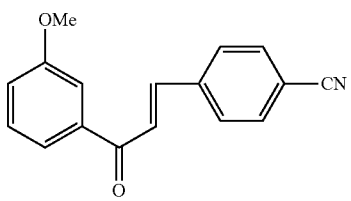
Compound 108
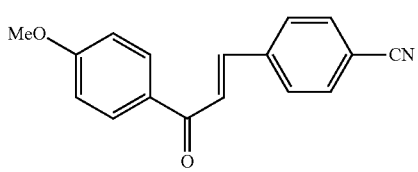
Compound 109
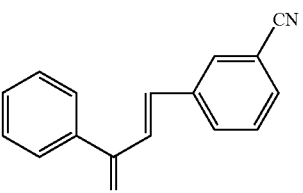
Compound 110
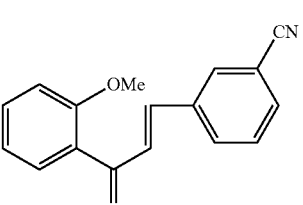
Compound 111
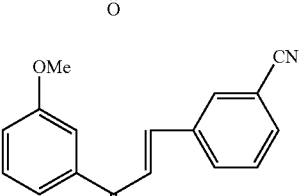
Compound 112
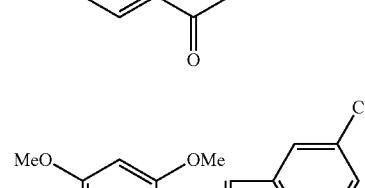
Compound 113
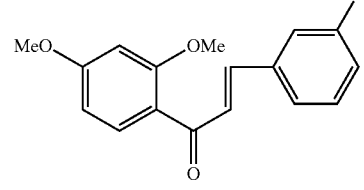

-continued
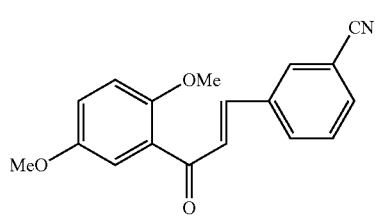
Compound 114
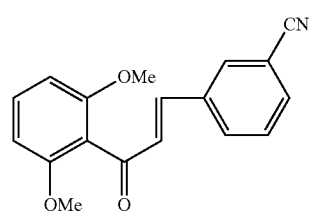
Compound 115
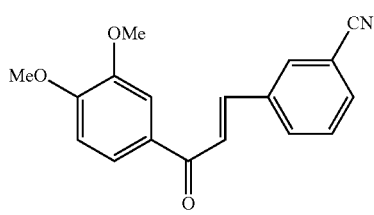
Compound 116
or
-continued
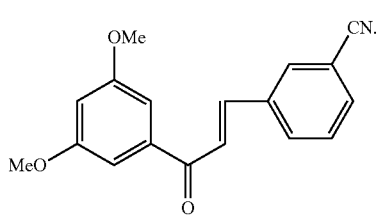
Compound 117
16. The method of claim 13, wherein the compound is
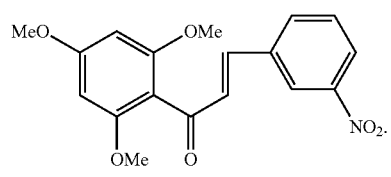
(compound 86)
17. The method of claim 13, wherein the prostate cancer is castrate resistant.
* * * * *